United States Patent
Zwiers et al.

(10) Patent No.: US 10,123,427 B2
(45) Date of Patent: Nov. 6, 2018

(54) INKJET SYSTEM FOR PRINTING A PRINTED CIRCUIT BOARD

(71) Applicant: MUTRACX INTERNATIONAL B.V., Nuenen (NL)

(72) Inventors: Henk Jan Zwiers, Venlo (NL); Jacobus Hendricus Johannes Janssen, Haps (NL); Joost Anne Veerman, Grubbenvorst (NL)

(73) Assignee: MUTRACX INTERNATIONAL B.V., Nuenen (NL)

( * ) Notice: Subject to any disclaimer, the term of this patent is extended or adjusted under 35 U.S.C. 154(b) by 0 days.

(21) Appl. No.: 15/677,926

(22) Filed: Aug. 15, 2017

(65) Prior Publication Data

US 2017/0347461 A1   Nov. 30, 2017

Related U.S. Application Data

(63) Continuation of application No. 15/148,780, filed on May 6, 2016, now Pat. No. 9,769,932, which is a (Continued)

(30) Foreign Application Priority Data

Jan. 2, 2012  (NL) ...................... 2008063
Jan. 2, 2012  (NL) ...................... 2008064
(Continued)

(51) Int. Cl.
  *B41J 25/00*  (2006.01)
  *B05B 13/02*  (2006.01)
(Continued)

(52) U.S. Cl.
  CPC ............... *H05K 3/125* (2013.01); *B05B 1/08* (2013.01); *B05B 12/16* (2018.02);
(Continued)

(58) Field of Classification Search
  CPC ....... B41J 25/001; H05K 3/008; H05K 3/125; H05K 3/22; B05B 13/0221
  See application file for complete search history.

(56) References Cited

U.S. PATENT DOCUMENTS

| 4,623,256 A | 11/1986 | Ikenaga et al. |
| 5,644,347 A | 7/1997 | Schwiebert et al. |

(Continued)

FOREIGN PATENT DOCUMENTS

| CN | 1221974 A | 7/1999 |
| CN | 1462065 A | 12/2003 |

(Continued)

OTHER PUBLICATIONS

Chinese Office Action and Search Report for Chinese Application No. 201710213793.9, dated Jan. 2, 2018, with an English translation.

(Continued)

*Primary Examiner* — Jason Uhlenhake
(74) *Attorney, Agent, or Firm* — Birch, Stewart, Kolasch & Birch, LLP

(57) ABSTRACT

A printing process for printing an ink pattern on a substrate is provided. The ink pattern to be printed is based on an available pattern layout. The pattern layout defines a desired layout of the ink pattern to be printed. Based on the pattern layout an input image for allocating dot positions of the ink pattern is generated. The printing process includes a step of comparing a scan image with the input image to carry out a quality inspection to detect any print defects in the printed ink pattern. The printing process includes a step of providing a decision on an approval or a rejection of the printed ink pattern. In case of an approval, the substrate can be supplied (Continued)

to a subsequent processing station to finalise the substrate. In case of a rejection, the substrate including print defects can be recycled.

20 Claims, 25 Drawing Sheets

Related U.S. Application Data continuation of application No. 14/370,195, filed as application No. PCT/NL2012/050934 on Dec. 28, 2012, now Pat. No. 9,363,899.

(30) Foreign Application Priority Data

| Jan. 2, 2012 | (NL) | ..................................... | 2008065 |
|---|---|---|---|
| Jan. 2, 2012 | (NL) | ..................................... | 2008066 |
| Jan. 2, 2012 | (NL) | ..................................... | 2008067 |
| Jan. 2, 2012 | (NL) | ..................................... | 2008068 |

(51) Int. Cl.
```
H05K 3/00       (2006.01)
H05K 3/12       (2006.01)
H05K 3/22       (2006.01)
H01L 21/288     (2006.01)
H01L 23/544     (2006.01)
G01N 21/956     (2006.01)
B05B 1/08       (2006.01)
H01L 21/66      (2006.01)
H05K 1/09       (2006.01)
B41J 2/165      (2006.01)
B41J 2/21       (2006.01)
B05B 12/16      (2018.01)
H05K 3/06       (2006.01)
```

(52) U.S. Cl.
CPC ....... *B05B 13/0221* (2013.01); *B41J 2/16538* (2013.01); *B41J 2/16544* (2013.01); *B41J 2/2132* (2013.01); *B41J 25/001* (2013.01); *G01N 21/95607* (2013.01); *H01L 21/288* (2013.01); *H01L 22/12* (2013.01); *H01L 23/544* (2013.01); *H05K 1/092* (2013.01); *H05K 3/0079* (2013.01); *H05K 3/22* (2013.01); *G01N 2021/95615* (2013.01); *H01L 2924/0002* (2013.01); *H05K 3/061* (2013.01); *H05K 2203/013* (2013.01); *H05K 2203/1461* (2013.01); *H05K 2203/1563* (2013.01); *H05K 2203/1572* (2013.01); *H05K 2203/16* (2013.01); *H05K 2203/162* (2013.01); *H05K 2203/163* (2013.01)

(56) References Cited

U.S. PATENT DOCUMENTS

| 6,007,193 A | 12/1999 | Kashimura et al. |
|---|---|---|
| 6,033,065 A | 3/2000 | Ikezaki |
| 6,081,613 A | 6/2000 | Ikurumi et al. |
| 6,849,308 B1 | 2/2005 | Speakman et al. |
| 7,993,466 B2 | 8/2011 | Aude |
| 2003/0177639 A1 | 9/2003 | Berg |
| 2004/0036731 A1 | 2/2004 | Ready et al. |
| 2004/0061736 A1 | 4/2004 | Yun et al. |
| 2006/0066664 A1 | 3/2006 | Kachi et al. |
| 2006/0086773 A1 | 4/2006 | Sanftleben et al. |
| 2006/0154035 A1* | 7/2006 | Iwata ..................... B41M 7/00 428/209 |
| 2006/0169672 A1 | 8/2006 | Toyoda |
| 2007/0154081 A1 | 7/2007 | Levi et al. |
| 2008/0018701 A1 | 1/2008 | Lee |
| 2009/0051894 A1 | 2/2009 | Shibazaki et al. |
| 2009/0079777 A1 | 3/2009 | Nagamura et al. |
| 2009/0229118 A1 | 9/2009 | Haugen |
| 2010/0020144 A1 | 1/2010 | McCracken et al. |
| 2010/0242754 A1* | 9/2010 | Nishi ................... B41F 15/0818 101/123 |
| 2010/0259587 A1 | 10/2010 | Uptergrove |
| 2010/0266961 A1 | 10/2010 | Kawamura et al. |
| 2011/0032293 A1 | 2/2011 | Yamamoto et al. |
| 2011/0106287 A1 | 5/2011 | Akagawa et al. |
| 2011/0205296 A1 | 8/2011 | Colombat et al. |
| 2012/0154499 A1 | 6/2012 | Mori et al. |
| 2012/0229535 A1* | 9/2012 | Akiyama ............... B41J 2/2114 347/5 |
| 2015/0116399 A1* | 4/2015 | Sai ....................... B41J 2/16511 347/9 |

FOREIGN PATENT DOCUMENTS

| CN | 201833657 U | 5/2011 |
|---|---|---|
| CN | 102196916 A | 9/2011 |
| EP | 1 392 091 A2 | 2/2004 |
| EP | 1 367 871 B1 | 10/2011 |
| JP | 2008-33284 A | 2/2008 |
| JP | 2010-259976 A | 11/2010 |
| JP | 2010-264696 A | 11/2010 |
| WO | WO 03/045697 A1 | 6/2003 |
| WO | WO 2008/065657 A2 | 6/2008 |

OTHER PUBLICATIONS

Chinese Office Action and Search Report for Chinese Application No. 201710213913.5, dated Jan. 2, 2018, with an English translation.
Chinese Office Action and Search Report for Chinese Application No. 201710214554.5, dated Jan. 2, 2018, with an English translation.
Extended European Search Report for European Application No. 17175965.7, dated Nov. 23, 2017.

\* cited by examiner

INKJET SYSTEM FOR PRINTING A PRINTED CIRCUIT BOARD

This application is a Continuation of U.S. application Ser. No. 15/148,780, filed on May 6, 2016, which is a Continuation of U.S. application Ser. No. 14/370,195, filed on Jul. 1, 2014 (now U.S. Pat. No. 9,363,899 issued on Jun. 7, 2016), which is the National Phase of International Application No. PCT/NL2012/050934, filed on Dec. 28, 2012, which claims the benefit under 35 U.S.C. § 119(a) to Dutch Patent Application Nos. 2008068, 2008067, 2008066, 2008065, 2008064, 2008063 filed on Jan. 2, 2012, all of which are hereby expressly incorporated by reference into the present application.

In general, the present invention relates to devices, methods and uses, for manufacturing a substrate comprising an ink pattern. In particular, the present invention relates to several aspects of a method and an inkjet system for manufacturing a printed circuit board by printing an ink pattern onto a substrate.

A first aspect of the invention relates to a printing process for printing an ink pattern on a substrate based on an available pattern layout. The substrate is an electronic substrate, in particular a printed circuit board, a PCB. The electronic substrate has a non-conductive base panel and a conductive layer on top of the base panel. The printing process is carried out to provide a conductive pattern on top of the electronic substrate. The pattern layout defines a desired layout of the ink pattern to be printed on a top surface of the substrate. Further, the first aspect of the invention relates to an inkjet system. In the printing process, the ink pattern is printed by an inkjet system onto the substrate to finally create the conductive pattern. After printing the ink pattern onto the substrate, the substrate is further processed and finalised by process stations, like etching and stripping stations. Before marketing the substrates, the substrates are each individually subjected to a final quality inspection in which the substrates are inspected on quality. The quality inspection means that the substrates are inspected on any defects. A defect may be a deficiency in the printed ink pattern, an etching failure, a scratch etc.

US2007/0154081 discloses a system for an inspection and verification of an electrical circuit. The system has a chassis which comprises a first station with an automatic optical inspection (AOI) device which performs AOI of an electrical circuit to identify candidate defects on the electrical circuit. Further, the chassis comprises a second station with a verification device which performs verification of the candidate defects identified by the AOI device. The system comprises a first and a second transportable table for supporting and transporting respectively a first and second electrical circuit between the first and second station. After manufacturing the electrical circuits, the substrates are collected in a batch and forwarded to the system for inspection and verification. Each substrate in a batch of substrates is provided serially to an integrated inspection, verification and correction system. Integrated inspection means that the verification and correction of suspected defects on an inspected substrate is performed generally simultaneously with the inspection of a new substrate. After carrying out the inspection, verification and correction, additional printed circuit board processing steps, such as an application of a solder mask may be performed to finalise a printed circuit board.

The inspection, verification and correction are carried out simultaneously to increase a production rate. A drawback of the disclosed system is that despite of this simultaneously work out, the complete production time per substrate still requires a too long time interval. The processing and inspection of the batch of substrates is time-consuming and upholds the production of printed circuit boards.

The general object of the present first aspect of the invention is to at least partially eliminate the above mentioned drawbacks and/or to provide a useable alternative. More specific, it is an object of the first aspect of the invention to provide a printing process of electrical circuits and a quality inspection which is less time-consuming and which provides an increase in production rate.

According to the first aspect of the invention, this object is achieved by a printing process according to claim 1.

According to the first aspect of the invention a printing process for printing an ink pattern on a substrate is provided. In particular, the substrate is an electronic substrate for electrically connecting electronics, more in particular a printed circuit board. The ink pattern to be printed is based on an available pattern layout. The pattern layout defines a desired layout of the ink pattern to be printed.

The printing process according to the first aspect of the invention comprises a step of providing an inkjet system. The inkjet system comprises a framework for holding components of the inkjet system. The inkjet system comprises a print head assembly for ejecting droplets of ink on a substrate. The print head assembly is mounted to the framework. The print head assembly is positioned in a printing area of the inkjet system. In the printing process, the print head assembly is used to print the ink pattern onto a substrate. The inkjet system comprises control electronics for controlling the inkjet system. The inkjet system further comprises a scanning unit for scanning a printed ink pattern on a substrate. The scanning unit is mounted to the framework of the inkjet system. Preferably, the scanning unit is positioned adjacent the print head assembly for immediately scanning a printed ink pattern.

The printing process according to the first aspect of the invention comprises a step of generating an input image for allocating dot positions of the ink pattern to be printed by the printhead assembly. The input image is based on the pattern layout. Preferably, the generating of the input image means a rasterizing of the pattern layout to a raster input image. The raster input image provides an allocation of dot positions of the ink pattern to be printed. The print head assembly is configured to operate and eject ink droplets based on an inputted input image.

The printing process according to the first aspect of the invention comprises a step of providing the substrate to be printed. The substrate may be conveyed to the printing area of the inkjet system by a substrate conveyor for printing an ink pattern on a top surface of the substrate. The top surface of the substrate may be a front- or bottomside of the substrate.

The printing process according to the first aspect of the invention comprises a step of printing an ink pattern based on the input image onto the substrate by the print head assembly of the inkjet system.

The printing process according to the first aspect of the invention comprises a step of scanning the printed ink pattern by the scanning unit. The scanning unit is arranged to obtain a scan image, in particular a raster scan image, of the printed ink pattern.

The printing process according to the first aspect of the invention comprises a step of comparing the scan image with the input image to carry out a quality inspection. The quality inspection is carried out to detect any print defects in the printed ink pattern.

The printing process according to the first aspect of the invention comprises a step of providing a decision on an approval or a rejection of the printed ink pattern on the substrate. In case of an approval, the substrate can be supplied to a subsequent processing station to finalise the substrate. The next processing station may be positioned adjacent to the inkjet system. In particular, the processing station is an etch station for etching the substrate. In case of a rejection, the substrate including print defects may be discharged.

The printing process according to the first aspect of the invention provides a quality inspection of a printed substrate, wherein the quality inspection is integrated in the printing process. Advantageously, the quality inspection is performed relatively simple by just comparing the scan image with the inputted pattern layout. In particular, the scan image is compared with the input image. Preferably, the scan image is a raster scan image which is compared with a raster input image.

Each individual printed substrate can be immediately inspected before further processing steps are carried out. Substrates which include misprints can directly be discharged from the inkjet system. Substrates with misprints do not longer uphold the printing process which increases the production rate of the system. When detecting a misprint on an individual substrate, an alarm signal may be generated by the control electronics. The alarm signal may indicate a related cause of the misprint. Maintenance can be performed to prevent similar misprints on subsequent substrates. Herewith, the inline quality inspection may prevent a series of substrates all including misprints originating from the same source, e.g. a disturbed nozzle.

The quality inspection is carried out in-line and controlled by the control electronics of the inkjet system. In-line means that the quality inspection is carried out after printing the ink pattern on a substrate and before etching the substrate. The quality inspection can be carried out on a first substrate during a step of printing an ink pattern on a subsequent substrate. The quality inspection is preferably carried out on the inkjet system. The quality inspection is preferably performed on board of the inkjet system, which means that the quality inspection is carried out for a substrate which is located at the inkjet system. No additional stand alone inspection system, like an AIO device, is necessary. Control electronics and a scanning unit of the inkjet system itself are used to carry out the quality inspection.

The quality inspection is an interim quality inspection which is carried out after printing an ink pattern onto the substrate, and before a further finalising process like etching or stripping of the substrate takes place. The interim quality inspection may be performed in between two printing steps on the same surface of a substrate. The interim quality inspection may be followed by a final quality inspection after finishing the manufacturing of the substrate. The quality inspection is carried out on an intermediate state of the substrate. Advantageously, a final quality inspection after etching of the substrate can be less extensive. The substrate is already inspected on typical defects during the interim quality inspection at an intermediate stage of the manufacturing process, which allows a quicker final quality inspection at the end of the manufacturing process.

The interim quality inspection on board of the inkjet system enables several advantageous embodiments.

In an embodiment of the printing process according to the first aspect of the invention, the scan image is a raster scan image which is compared with an input image which is a raster input image. The raster input image is generated by rasterizing the pattern layout to a raster input image for allocating dot positions of the ink pattern to be printed by the printhead assembly. Advantageously, the quality inspection can be performed relatively quick by just comparing the raster scan image with the raster input image. The quick quality inspection reduces an uphold of substrates and increases a production rate of the inkjet system.

In an embodiment of the printing process according to the first aspect of the invention, the substrate is in case of a rejection of the substrate, discharged to a discharge station. The discharge station may be a waste station for buffering rejected substrates. Each individual substrate is subjected to the inline quality inspection before finalising the substrate by an etching process. A rejected substrate including a misprint can be separated from a main production stream of substrates conveyed through the inkjet system and may be discharged from the main production stream. Rejected substrates will not be forwarded to finalising stations like etching baths and stripping stations. Early discharged rejected substrates do not longer reduce an efficiency of a finalising process after the printing process. Advantageously, the finalising stations may only be used to finalise substrates which are already inspected on misprints. Only approved substrates may be further processed which allows a high efficiency and yield of a manufacturing process for electronic substrates. Substrates which include misprints will not negatively affect a work capacity of the further finalising process.

Additionally, the rejected printed substrates will not be subjected to a final inspection by an automated optical inspection AOI unit which has normally a long job time. Herewith, the total printing process and manufacturing of electronic substrates may proceed more efficiently. The production rate is increased.

In an embodiment of the printing process according to the first aspect of the invention, the discharge station is a recycle station for recycling substrates. After carrying out the quality inspection on board of the inkjet system, a rejected substrate is discharged to the recycle station. In the recycle station, the rejected substrate is cleaned by removing a printed ink pattern. Subsequently, the cleaned substrate can be reused again in the inkjet system. The cleaned substrate may be returned to an input station for inputting substrates into the inkjet system. Advantageously, the on process quality inspection after the printing of an ink pattern and before a finalising process, like etching allows a recycling of printed substrates. A recycling of substrates would not be possible in such an easy manner after etching.

In an embodiment of the printing process according to the first aspect of the invention, a quality inspection is carried out for a substrate in a buffer unit of the inkjet system. The buffer unit is connected to the framework of the inkjet system. A substrate is conveyed to a buffer unit of the inkjet system. The quality inspection of the substrate is carried out in the buffer unit. Preferably, the buffer unit is positioned adjacent the scanning unit of the inkjet system. During the comparison of the scan image with the input image carried out by the quality inspection, the substrate is temporary stored in the buffer unit. An upstream substrate in a stream of substrates through the inkjet system may be printed during the quality inspection of a downstream positioned substrate in the buffer unit.

In an embodiment of the printing process according to the first aspect of the invention, a quality inspection step is carried out for a first substrate is simultaneously carried out with a printing step of printing an ink pattern onto a second substrate in a production stream of substrates. The first substrate is positioned downstream the second substrate in the stream of substrates through the inkjet system. The first substrate is subjected to a quality inspection while the second substrate is printed. The first substrate is positioned outside the printing area, wherein the second substrate is positioned inside the printing area. The first substrate is conveyed to a separate position away from the printing area for carrying out the quality inspection. The separate position may be located in the buffer unit for temporary storing at least one substrate. By carrying out the quality inspection on substrates in the buffer unit, the quality inspection does not uphold the production stream of substrates. Advantageously, a higher efficiency of printing process carried out by the inkjet system may be achieved.

In particular, the buffer unit may be a turn buffer unit including a turn unit for turning around a substrate. In a first step, a substrate may be received in the turn buffer unit, in which an ink pattern is printed on a topside of the substrate. Subsequently, a first quality inspection may be carried out to inspect the printed ink pattern on the topside. After an approval, the first substrate may be turned around by the turn-buffer unit and in a subsequent step being re-supplied in the printing area of the inkjet system for a next printing step in which a bottomside of the substrate is provided with an ink pattern. After printing the bottomside of the substrate, a second quality inspection is carried out for inspecting any deficiencies in the printed ink pattern on the bottomside of the substrate. If the first quality inspection on the ink pattern on the topside reveals any deficiencies, the substrate may be discharged from the production stream of substrates.

In a particular embodiment, the inkjet system comprises an input unit which is arranged as a turn-buffer unit. In the first place, the input unit is arranged for inputting blank substrates to the print area of the inkjet system. In the second place the input unit is arranged for receiving, rotating and inputting a topside printed substrate from and to the print area of the inkjet system.

In an embodiment of the printing process according to the first aspect of the invention, the printing process comprises a preparing step of filtering at least one control feature from the input image, in particular the raster input image, before carrying out the quality inspection. The control features are filtered by the control electronics of the inkjet system. A control feature defines a candidate defect of an ink pattern. The candidate defect defined by the control feature is inspected during the quality inspection. A control feature may define a particular position and/or geometry of the input image which might be susceptible to a misprint. The control features may indicate critical geometries and/or spots of the input image. A control feature may define a track, pad or area. A critical spot may for example be formed by a small gap in between distinguished geometries. The control feature may define a region of the ink pattern which has a higher risk on a print failure during a printing process. During the preparing quality inspection step, control features of the input image which contribute to a higher risk of misprints are recognised and marked. During the comparison step of the quality inspection, the control features are taken into account in making a comparison of the input image and the scan image, in particular the raster scan image. By checking only the control features in the made comparison, the quality inspection can be carried out in a short job time. Due to the filtered control features, not all details of the scan image need to be compared. Herewith, the quality inspection step can be carried out in a relatively short timeframe of about thirty seconds. The inline quality inspection enables an fast and hardly uninterrupted printing process.

In an embodiment of the printing process according to the first aspect of the invention, the preparing step of filtering at least one control feature to define candidate defects from the input image is at least partially carried out during the printing and/or scanning step of the printing process. The preparing step of the quality inspection can at least partially be performed simultaneously to other steps of the printing process. The preparing quality inspection step may be performed in a timeframe of about five minutes. A step of the quality inspection can be carried out before finishing a printing step in which an ink pattern is deposited on the substrate. The quality inspection is carried out based on a input image, preferably raster input image, which is already available before printing the ink pattern. Based on the input image, candidate defects may already be identified. The preparing quality inspection step can be completed when finishing the scanning step of the printing process. Subsequently, the comparing step of the quality inspection can be carried out directly by comparing the control features of the input image with the scan image. In comparison with a quality inspection in a separate successive step, the interim quality inspection according to the first aspect of the invention which is at least partially carried out simultaneously during the printing process can be carried out in a shorter time interval. The quality inspection may be less time consuming. A production rate of substrates is advantageously increased.

In an embodiment of the printing process according to the first aspect of the invention, a control feature may be of a particular type. The type of a control feature may e.g. be an arc portion or a chamfered corner portion of the ink pattern to be printed. A control feature may be a position of a connection portion in between two typical distinguishable geometries of an ink pattern. A control feature may indicate e.g. a position of the input image in which a line portion is connected to an arc portion. Such a connection portion of the ink pattern may provide a higher risk on a misprint. If the connection portion does not provide a solid joint, this may result in a poor electrical connection. Advantageously, by classifying the control features, the quality inspection can be carried out for minimising a risk on misprints.

In an embodiment of the printing process according to the first aspect of the invention, each type of control features may be grouped in a corresponding group. A first group of control features may be e.g. be defined by circular portions or pads of the ink pattern. A second group of control features may define line elements which form signal traces. A third group may define holes which may form electrical connections in between a laminated multilayer substrate. A fourth group of control features may define critical spots, like gaps, of the ink pattern. Advantageously, the quality inspection may be carried out for an individual group of control features. Herewith, the quality inspection can be flexible. The accuracy and job time of a quality inspection can be influenced by an operator of the printing process by selecting one or more groups of control features to be inspected.

In an embodiment of the printing process according to the first aspect of the invention, the control features are selected by applying a mask to the input image, in particular to the raster input image. The mask is arranged for filtering a type of control features from the input image. The mask can be applied for masking irrelevant areas of the input image to filter a type of control features from the input image. A mask may be pre-programmed in the control electronics of the inkjet system. Advantageously, the selection of control features by a mask provides a simple manner of deducting relevant positions and geometries of the ink pattern to be checked during the quality inspection.

In an embodiment of the printing process according to the first aspect of the invention, the filtering of control features comprises at least one selection criterion to filter at least one critical part of a input image. A selection criterion makes the filtering of control features dependent on production circumstances. A selection criterion defines under which circumstances the control features are selected. The selection criterion may comprise an input parameter which is adjustable by an operator of the inkjet system. The selection criteria may for example be switched on or off to respectively take a critical part of the ink pattern into account or not. Preferably, the selection criterion is automatically controlled by the control electronics. The selection criterion may be linked to a printing mode and may relate to a required accuracy or a required printing speed. Also other printing characteristics may determine the criterion. The selection criterion may be print job dependent. Advantageously, by selectively defining the selection criteria, the extraction of control features and quality inspection may be carried out in a selective and an efficient manner.

In an embodiment of the printing process according to the first aspect of the invention, the step of scanning is carried out by a scanning unit of the inkjet system. The scanning unit is connected to the framework of the inkjet system. Preferably, the scanning unit is positioned adjacent to the printhead assembly of the inkjet system. The scanning unit comprises a light source for illuminating at least a part of the ink pattern of the substrate. Further, the scanning unit comprises an imaging unit for capturing a raster scan image. Preferably, the light source is arranged to provide an optimal contrast in between the ink pattern printed on the substrate and a background formed by the area of the top surface of the substrate outside the ink pattern. The light source generates an illumination of the ink pattern in a specific light colour. Preferably, the light source is monochrome. An emitted light colour of the light source is tuned to an extreme reflection value of the ink pattern and/or background surface. In practice, the emitted light colour corresponds to a colour of applied ink droplets or to a colour of a top surface of the substrate. In particular, a selected resist colour is blue to achieve an optimal optical contrast with a copper top surface of a substrate, wherein a corresponding illumination is red coloured for maximum absorption in the resist and maximum reflection on the copper top surface. Herewith, an optimal contrast may be obtained which improves the scanning process and allows an increased accuracy of the quality inspection.

In an embodiment of the printing process according to the first aspect of the invention, the printing process comprises a step of marking a substrate before forwarding an approved substrate to a further process station. The substrate may be marked with a unique identification by a marking station to enable a tracing of the substrate during a manufacturing process and in the market. The approved substrate may be marked with a serial number.

In an embodiment of the printing process according to the first aspect of the invention, the printing process is integrated in a manufacturing process for manufacturing electronic substrates. The printing process is carried out in a first stage of the manufacturing process. In a final stage of the manufacturing process, a printed substrate is etched and stripped. A quality inspection is carried out at the end of the first stage of the manufacturing process before starting the final stage.

Further, the first aspect of the invention relates to a use of the printing process for manufacturing an electronic substrate. The first aspect of the invention relates to a manufacturing process for manufacturing a printed electronic substrate. An electronic substrate is for example a display panel or a printed circuit board. In particular the invention relates to a printing process for manufacturing a printed circuit board (PCB).

In an embodiment of the manufacturing process according to the first aspect of the invention, a next process station positioned after the inkjet system is an etch station for etching the substrate. The etch station may comprise an etch bath which may be filled with an etch liquid. The substrate may be submerged in the etch bath to remove a top layer, in particular a copper layer, away from the substrate. After etching the substrate, the substrate may be further processed to a stripping station for stripping away the etch resistant ink. After removing the ink pattern of the substrate, the substrate may be ready for use. A final quality inspection of the substrate may be carried out by an automated optical inspection. Advantageously, the final inspection can be focused on typical failures which might occur during etching or stripping of the substrate. Typical failures which would originate from the printing step are already inspected during the intermediate inline quality inspection and can advantageously be left outside the scope of inspection in a final stage. This allows a more efficient and less time consuming inspection.

Further, embodiments are defined in the sub-claims.

Further, first aspect of the invention relates to an inkjet system for printing and ink pattern on a substrate. The inkjet system comprises a substrate conveyor for carrying and moving a substrate. The inkjet system comprises an inkjet print head assembly for ejecting droplets of ink on a top surface of the substrate for printing the ink pattern. Further, the inkjet system comprises a scanning unit for scanning the printed ink pattern of the substrate. The inkjet system comprises control electronics for controlling the inkjet system. The control electronics are configured to carry out a printing process according to the first aspect of the invention.

In an embodiment of the inkjet system according to the first aspect of the invention, the control electronics comprises logic configured to carry out a quality inspection by comparing a scan image, in particular a raster scan image which originates from the scanning unit with an input image, in particular a raster input image which originates from a pattern layout. In particular, the logic is configured to extract control features from an input image for preparing the quality inspection.

In an embodiment of the inkjet system according to the first aspect of the invention, the logic is embedded in a chip. Preferably, the chip is a field programmable chip, an FPGA chip. The logic embedded in the chip may comprise image correction to increase linearity, up-sampling to increase resolution, noise filtering and threshold functionality. Advantageously, the logic in that it in a chip functions faster and more reliable then logic written in software.

In an embodiment of the inkjet system according to the first aspect of the invention, the inkjet system comprises a buffer unit for temporary storing a substrate. The quality inspection for a substrate is carried out on a temporary stored substrate in the buffer unit, while a subsequent substrate is printed in a printing area of the inkjet system. In a first stage of the printing process, the substrate is received in a printing area of the inkjet system and printed on a topside. Subsequently, the printed ink pattern is inspected by a quality inspection on misprints in the buffer unit. After carrying out the quality inspection and approving the substrate, the substrate may be conveyed away from the inkjet system to a next process station.

In particular, the buffer unit is a turn-buffer unit for temporary storing and turning around a substrate. The turn-buffer unit has a turn unit for rotating received substrates. Received substrates can be turned around by the turn unit. The printing process may comprise a step of turning around a substrate in the turn-buffer unit before re-supplying the substrate to a printing area of the inkjet system. Herewith, both the topside and the bottomside of the substrate can be printed.

A substrate may be turned around by the turn-buffer unit of the inkjet system. After a first stage of the printing process, including a first printing step and a first quality inspection, the substrate may be, supplied again in a second stage of the printing process to the printing area of the inkjet system to print a bottomside of the substrate.

In a particular embodiment, the inkjet system comprises an input unit for inputting substrates to the printing area of the inkjet system, wherein the input unit is arranged as a turn-buffer unit. In a first stage of the printing process, the input unit is arranged for inputting blank substrates to the printing area of the inkjet system. A blank substrate has a non-printed top- and bottomside. In a second stage of the printing process the input unit is arranged for receiving, rotating and inputting a topside printed substrate from and to the printing area of the inkjet system.

In an embodiment of the inkjet system according to the first aspect of the invention, the scanning unit comprises a light source for illuminating at least a part of the ink pattern of the substrate. Further, the scanning unit comprises an imaging unit for capturing a raster scan image. Preferably, the light source is arranged to provide an optimal contrast in between the ink pattern printed on the substrate and a background formed by the area of the top surface of the substrate outside the ink pattern. The light source generates an illumination of the ink pattern in a specific light colour. Preferably, the light source is monochrome. An emitted light colour of the light source is tuned to an extreme reflection value of the ink pattern and/or background surface. In practice, the emitted light colour corresponds to a colour of applied ink droplets or to a colour of a top surface of the substrate. In particular, a selected resist colour is blue to achieve an optimal optical contrast with a copper top surface of a substrate, wherein a corresponding illumination is red coloured for maximum absorption in the resist and maximum reflection on the copper top surface. Herewith, an optimal contrast may be obtained which improves the scanning process and allows an increased accuracy of the quality inspection.

In an embodiment of the inkjet system according to the first aspect of the invention, the scanning unit comprises a LED bar as a light source. Advantageously, the LED bar is suitable to provide a monochromatic illumination. Additionally, the intensity of the illumination is fully adjustable.

Further, the invention relates to a substrate production line for producing electronic substrates, in particular printed circuit boards. The substrate production line comprises an inkjet system according to the first aspect of the invention and further comprises an etch station for etching a substrate. The substrate production line has a main production stream of substrates in which the substrates are first printed at the inkjet system and subsequently etched at the etch station. The etch station is positioned downstream to the inkjet system. The main production stream is branched. The main production stream is branched before the etch station. The main production stream comprises a branch stream upstream the etch station which extends from the inkjet system to a discharge station for ejecting substrates from the main production stream. Substrates can be ejected by the branch stream after carrying out a quality inspection on a printed ink pattern of the substrate.

Further embodiments of the first aspect of the invention are defined by the claims.

Now a second aspect of the invention will be addressed.

A second aspect of the invention relates to an inkjet system, in particular a drop-on-demand inkjet system for industrial applications.

Drop-on-demand inkjet systems are well-known, especially in the consumer market where inkjet printers for paper applications have proven to be very successful over the years. An advantage of inkjet systems over other printing techniques such as impact printing is that no direct contact is required between inkjet system and substrate to provide the substrate with a desired pattern. Also part of the success of consumer inkjet printers is that manufacturers found ways to develop small and relatively cheap inkjet printers.

Recent developments have been directed to make use of inkjet systems in other applications than traditional paper applications as well. However, these developments have not been very successful, especially not when a high accuracy and reliability is required.

Examples of applications where inkjet systems are considered to be a promising manufacturing tool due to its simplicity and speed are:
providing etch resist masks on printed circuit boards (PCB);
providing solder masks for PCB manufacturing;
providing masks for electrode patterning for solar cells; or
manufacturing of active or passive circuit components, display components, antennas and/or electronic components on substrates including flexible substrates.

Inkjet systems can be used to deposit the required mask layers or structures in a desired pattern, e.g. a pattern corresponding to the electronic wiring on a PCB. Depending on the desired line width of the electronic wiring and the size of the droplets used, a missing or misplaced droplet may have an enormous impact on the working of the electronic wiring and thus the PCB. For instance, a missing droplet may cause a wire to have a undesirably high local electrical resistance which may even cause electromigration. A malfunctioning PCB may be the result.

Due to the small droplet size of current inkjet systems, which droplet size is typically 5-50 pL, many droplets are required to produce an average pattern. For instance, the amount of droplets applied to a substrate, e.g. a PCB panel of typically 21×24 inches, will generally be in the order of 109. When e.g. a reasonable yield of 99% is desired, only one error in 1011 droplets is allowed. Such a high reliability of inkjet systems is not yet achievable.

Hence, two major challenges in developing industrial applicable inkjet systems are to improve the placement accuracy of the droplets and to increase the reliability, so that it can be ensured that every droplet required for a pattern has indeed been generated and placed on the substrate.

It is therefore an object of the second aspect of the invention to provide an inkjet system having an improved accuracy and/or an improved reliability.

To achieve this object, an inkjet system according to clause 1 prefix 971 is provided.

An advantage of this inkjet system is that each nozzle has a back-up nozzle which increases the reliability, because in case of a failing nozzle another nozzle is able to take over the printing job of the failing nozzle. Further, by providing back-up nozzles in the form of a back-up print head, a malfunction affecting the entire print head is unlikely to affect the other print head thereby further increasing the reliability. This in contrast to the situation in which back-up nozzles are provided in the same print head.

In an embodiment, each print head comprises a row of nozzles, said row being positioned non-perpendicular to the printing direction, e.g. at an angle between 45 and 65 degrees relative to the printing direction. Due to this orientation of the nozzles, the nozzles do not necessarily have to be placed very close to each other in order to get a sufficient resolution in the direction perpendicular to the printing direction. The nozzles are then positioned at a relative small distance from each other in the direction perpendicular to the printing direction and at a relatively large distance from each other in the printing direction. As a result, the overall distance between the nozzles is large enough to prevent or at least minimize cross-talk between adjacent nozzles. An advantage is that the required resolution may be obtained by a single print head and not by combining multiple print heads which then have to be aligned properly with respect to each other.

In an alternative embodiment, the pitch between the nozzles in the horizontal direction perpendicular to the printing direction is not sufficient to obtain the required resolution in a single passing of the substrate, but the resolution is obtained by passing multiple times, i.e. using multiple swaths, in which the substrate each time is positioned differently in said direction perpendicular to the printing direction. Although this embodiment may require multiple swaths depending on the pattern to be printed, the advantage is that less nozzles and/or less print heads are required.

In an embodiment, each primary print head has an associated tertiary print head arranged at a distance from the primary and secondary print head in the printing direction, wherein each nozzle of a primary print head has a corresponding nozzle at the associated tertiary print head, and wherein a primary print head and its associated tertiary print head are arranged with respect to each other such that the virtual printing lines of corresponding nozzles substantially lie at the same position. This further increases the reliability as each nozzle now has two redundant nozzles which can take over the printing job in case of a failure. The three redundant nozzles also allow one nozzle to be non-available, e.g. for measuring or analysis reasons or for recuperating reasons, while the other two nozzles are able to continue printing without losing any reliability as one of the two nozzles is still able to take over printing of the other of the two nozzles.

In an embodiment, the print head assembly comprises a print head holder for holding the multiple print heads. The print head holder is preferably supported at three distinct locations, e.g. by a frame, such that the print head holder is stably and statically determinately supported which increases the position accuracy of the print heads and thus the accuracy of the droplet placement by the print heads.

In an embodiment, the print head holder is kept stationary and the substrate holder is allowed to move relative to the print head holder. As a result, no disturbances are introduced into the print head holder due to movement and actuation of the print head holder, which allows for an accurate positioning of the print heads with respect to each other. Additionally, the accurate positioning may also be easier to maintain once established as no dynamic deformations may be present.

In an embodiment, the dimension of the printing plane in a direction perpendicular to the printing direction is at least as large as the largest allowable substrate dimension in said direction that can be handled by the substrate holder. As a result, less movements of the substrate are required to finish printing the pattern which increases the obtainable accuracy with respect to the situation in which said dimension of the printing plane is smaller.

From prior art inkjet systems it is known that in case of multiple print heads it is challenging to align the print heads with respect to each other, especially when also taking into account thermal effects such as thermal expansion of the print head holder.

In an embodiment, each print head has an associated print head positioning device arranged between said print head and the print head holder for positioning said print head relative to the print head holder, thereby allowing to align primary print heads with their associated secondary print heads in order to align the virtual printing lines of corresponding nozzles, and to align primary print heads with respect to each other. In case also tertiary print heads or even more print heads are associated with a primary print head, these can also be aligned properly.

An advantage of providing a print head positioning device separate from the print head holder may be that the print head holder may be fabricated less accurate and can be optimized from mechanical (strength and stiffness) and thermal (stability) point of view without having to worry about the positioning of the print heads. Inaccuracies in the print head holder can be compensated for by the print head positioning devices.

Preferably, each print head positioning device comprises a base member releasably mountable to the print head holder, and a body connected to the base member for holding the print head, which body is moveable with respect to the base member by at least one actuator in a plane substantially parallel to the printing plane. The releasability of the base member has the advantage that a print head including print head positioning device can be assembled and introduced into the print head holder as a single unit. In case of failure it is also easy to remove such a unit and replace it with another unit comprising a print head and a print head positioning device.

The actuators positioning the body of the print head positioning device are preferably arranged in between the base member and the body to be replaced along with the unit, but may alternatively be arranged between the print head holder and the body. As a result, the actuator does not have to be replaced along with the unit, which may be beneficial from an electrical connection point of view, because power and data can now be provided to the actuators via the print head holder.

In an embodiment, the body is moveable with respect to the base member in a translational direction and a rotational direction, wherein the translational direction preferably has a component in a direction perpendicular to the printing direction. When a print head comprises a row of nozzles which row is non-perpendicular to the printing direction, the translational direction is preferably perpendicular to the row. If no other movements are allowed, these two degrees of freedom are able to set the required distance in the direction perpendicular to the printing direction between adjacent nozzles (i.e the pitch or resolution) and to align one print head to another print head in said direction. In other words, the rotational direction is able to set the resolution, while the translational direction is able to align the respective print heads in the direction perpendicular to the printing direction.

In an embodiment, it may not be possible to align the print heads in printing direction as well at the same time. However, alignment in that direction may be solved in a different way, for instance by measuring the distance between print heads and adjusting the timing for each nozzle.

In an embodiment, the body is connected to the base member via elastic hinges such that the body is only moveable relative to the base member in said plane parallel to the printing plane. An advantage is that this connection introduces no play which results in a more accurate positioning of the print heads. Further, a hysteresis-free positioning of the print head can be obtained. Preferably, the elastic hinges are made by locally removing material to allow elastic deformation of the remaining material.

When a unit formed by a print head and a print head positioning device is to be placed in and/or removed from the print head holder, any connection between the print head and the print head holder is preferably easy to make and easy to break. However, due to the movability of the print head relative to the print head holder this may not be a straightforward.

To solve this, one or more electrical connections between print head and print head holder are made via the base member of the print head positioning device, i.e. each print head is electrically connected to the print head holder via the base member of the associated print head positioning device. This can easily be done as the base member is always more or less connected to the print head holder in a similar way. The connection from base member to print head can then be integrated into the unit and is preferably flexible in order to cope with the movability of the print head.

Besides electrical connections, the print head may also require a connection to a pressure supply. Also this pressure may be supplied from the print head holder to each print head via the base member of the associated print head positioning device.

Typically, a print head requires two types of pressure supplies. One pressure supply provides underpressure to the print head, which underpressure can be used to prevent ink fluid from 'falling' (i.e. leaking) out of the nozzles due to gravity. An overpressure supply provides overpressure to the print head, which overpressure can be used to purge the nozzles during maintenance by forcing ink fluid through the nozzles without having to use the actuator used to eject droplets during normal operation.

In an embodiment, the print head holder comprises at least one chamber for applying an underpressure to one or more of the print heads, said chamber being connected to said print heads via the base member of the associated print head positioning devices.

In an embodiment, the print head holder comprises at least one chamber for applying an overpressure to one or more print heads, said chamber being connected to said print heads via the base member of the associated print head positioning devices.

In a preferred embodiment, the at least one underpressure chambers and/or the at least one overpressure chambers are integrated into the print head holder.

Using one or more of the abovementioned features in which connections between the print head and the print head holder run via the base member of the associated print head positioning device, the print head holder can advantageously be used to support the necessary supplies such as pressure supplies and control electronics, wherein the control electronics may be provided on a PCB board to be supported by the print head holder.

In an embodiment, the print head holder may also comprise a cooling unit to provide cooling to predefined parts of the print head holder, e.g. control electronics and/or the print head. For instance, the cooling unit may provide cool air in between the control electronics and the print head holder and/or in between the control electronics and the print head to reduce heat transfer from print head holder and/or print head to the control electronics.

In an embodiment, the print head holder comprises composite material, e.g. carbon fibre reinforced plastic, in order to minimize thermal expansion and increase thermal stability. Further, the composite material may be applied such that the stiffness of the print head holder in a plane parallel to the printing plane is high enough to obtain accurate positioning of the print heads. Further, the stiffness of the print head holder may be such that the print head holder is able to stably support the weight of the print heads, which may be up to 45 kilograms in case of sixty print heads.

In an embodiment, the unit formed by the print head and print head positioning device comprises a visual indicator to indicate the status of the unit, thereby allowing to distinguish at least between a properly functioning print head and an improperly functioning unit which requires maintenance or replacement. The information provided to the visual indicator is in that case preferably originating from an appropriate detection system able to detect the status of a print head. Maintenance personnel may benefit from this visual indicator as it can easily be seen which unit needs to be replaced/maintenanced or not.

In order to minimize the thermal effects on the positioning of the print heads, the print head positioning device preferably has a symmetric configuration.

In some inkjet systems, heat may be generated. This is for instance the case when the droplets are generated using a thermal actuator, e.g. as used in commercial available bubble-jet printers. Another possibility is that the ink fluid requires a high working temperature, e.g. to get the right viscosity and/or to be in the liquid phase, such as hot-melt ink.

However, heat may affect the working of other components and may have a dramatic effect on the accuracy of the inkjet system. In order to minimize the effect of heat, one or more of the following measures may be taken.

each print head comprises driving electronics, wherein the print heads and the print head holder are configured such that the driving electronics are arranged on a part of the print head extending outside the print head holder, and wherein the print head holder comprises a thermal shielding, preferably in the form of a thermally isolating layer, on a surface of the print head holder facing towards the driving electronics in order to minimize heat transport to the driving electronics, the print head holder comprises a thermal shielding, preferably in the form of a thermally isolating layer, on a surface of the print head holder facing towards the substrate during printing to minimize heat transport to the substrate, and the print head holder is configured to have minimal thermal expansion in the temperature working range (e.g. 40-120 degrees Celsius) of the inkjet system, e.g. by using suitable materials such as carbon fibre reinforced plastic.

The abovementioned measures to minimize the effect of heat may be combined with active cooling of parts, such as for instance providing cool air from a cooling device to control electronics or print heads.

In order to be able to position the print heads with respect to each other, the inkjet system is preferably comprising a droplet detection unit which is configured to detect the position of the droplets jetted on a substrate in a direction perpendicular to the printing direction.

A calibration unit can be provided which adjusts the position of the print heads based on the output of the droplet detection unit by driving the actuators of the respective print head positioning devices. In other words, the calibration unit drives the respective print head positioning devices in order to align the primary print heads with respect to each other and to align the secondary print heads with respect to their associated primary print head in the direction perpendicular to the printing direction. Driving of the respective print head positioning devices is done in dependency of the output of the droplet detection unit.

The sequence of detecting and adjusting the position of the print heads may be done a few times until the required position accuracy of the jetted droplets is obtained.

When required, the droplet detection device may also be configured to detect the position of the droplets jetted on a substrate in the printing direction. The calibration unit is then preferably configured to determine timing information for each nozzle which enables to accurately time the firing of a nozzle in order to get a respective droplet positioned at the required location on the substrate.

In order to improve the accuracy of the droplet detection unit, the droplet detection unit may emit and/or be sensitive to light having a frequency that is easily absorbed by the ink fluid and not by the substrate or the other way around. This has the advantage that maximum contrast is obtained.

In an embodiment, the droplet detection unit is arranged next to the print head assembly in the printing direction. The droplet detection unit is preferably a line scanner, which scans the substrate surface while the substrate moves relative, e.g. below, the droplet detection unit. Scanning may thus be done at full passing speed, so that a full image of the substrate can be obtained very fast.

In an embodiment, the droplet detection unit comprises multiple optical units which each are able to scan a portion of the substrates surface, wherein the multiple optical units each have a detection range which at least partially overlaps with the detection range of an adjacent optical unit, and wherein the detection ranges are combined electronically or by using software to act as a single optical unit. An optical unit may comprise a lens imaging system and a line CMOS sensor which are combined with image capturing electronics hardware. The fact that detection ranges at least partially overlap can advantageously be used to increase the detection accuracy in the overlapping ranges, because twice as much data is obtained in the overlapping areas.

In an embodiment, the droplet detection unit is supported by a stable and stiff supporting member, which is preferably made of a composite material with high thermal stability, e.g. a carbon fibre reinforced plastic.

The droplet detection unit preferably has a relatively large depth of focus, e.g. of about 50 micrometer, in order to allow substrate thickness or height variations without having to adjust the droplet detection unit or adjust the position of the substrate.

In an embodiment, the droplet detection unit may be calibrated by scanning an accurate prefabricated pattern, which pattern can be used to combine different optical units to act as a single optical unit if multiple optical units are present, but can e.g. also be used to compensate for lens distortion in one or more optical units.

In an embodiment, the droplet detection unit may also be used to inspect a printed pattern to check the printing performance for a specific printing job, i.e. the obtained pattern is compared to the desired pattern, e.g. to check the quality of the by the inkjet system manufactured devices.

The second aspect of the invention also relates to a method for accurately positioning print heads relative to each other, which method at least comprises the steps of:
  printing a test pattern on a test substrate using all print heads;
  obtaining an image of the printed test substrate by a droplet detection unit;
  determining the centre of mass for each printed droplet from the obtained image;
  comparing the determined centre of mass with the desired centre of mass of each droplet;
  determining position adjustment information for each print head from the comparison; and
  adjusting the position of the print heads based on the position adjustment information.

The method may be repeated as many times as required in order to obtain the required position accuracy of the print heads.

The test substrate may comprise a prefabricated calibration pattern which is measured first by the droplet detection unit and which can advantageously be used to calibrate the droplet detection unit itself or can be used as a reference for comparing the printed test pattern with the desired test pattern.

In addition to obtaining information about the position adjustment for each print head, the method may also be used to obtain timing information for the print heads which can advantageously be used to correctly time the ejection of a nozzle, so that the droplet is placed on a substrate at the right location. In this case, the timing determines the location of a droplet on a substrate in the printing direction, and the position of the nozzle, i.e. the print head alignment, determines the location of a droplet on a substrate in a direction perpendicular to the printing direction.

The second aspect of the invention further relates to a method for printing a pattern on a substrate in which use is made of an inkjet system as described above having primary, secondary and tertiary print heads, wherein the method comprises the following steps:
  alternatingly printing with the at least one primary print head and its associated secondary print head;
  while printing with the primary or the associated secondary print head, measuring the printing performance of each nozzle of the other one of the primary or associated secondary print head, i.e. the non-printing primary or associated secondary print head;
  predicting a future printing performance of each nozzle from the measured printing performance;
  in case the predicted future printing performance of a nozzle is unsatisfactory, stop printing with said nozzle and continue printing with a corresponding nozzle of the tertiary print head until the printing performance of said nozzle and the predicted future printing performance have improved to a desired level.

In an embodiment, the method depends on the direction in which the substrate moves relative to the print head assembly. Because the substrate is moveable relative to the print head assembly in the printing direction, two moving directions are possible, namely a positive printing direction alternatively referred to as a forward swath and a negative printing direction alternatively referred to as a backward swath. The first two print heads which are passed by the substrate during a swath are preferably alternatingly printing and the last print head to be passed is preferably used to replace nozzles of the first two print heads if necessary. This has the advantage that replacing a nozzle can always be done as the area of the substrate to be printed on still has to pass the last print head.

In an embodiment, control electronics are provided to determine which nozzles have to eject a droplet in order to obtain a desired pattern. From a control electronics point of view, the primary print head and its associated secondary and tertiary print heads are preferably considered to be one print head. The control electronics then send the information about the nozzles that have to print to a print head group controller. The group controller receives information about the printing performance of the nozzles and knows, if necessary, if a forward swath or a backward swath is carried out. Based on this information, the group controller independently of the other group controllers and the control electronics decides which print head, i.e. which primary, secondary or tertiary print head, will be used for printing the pattern received from the control electronics. In this way, the amount of data that has to be transported through the system is decreased with respect to the situation that the control electronics have to drive all print heads (primary, secondary and tertiary) individually. As a result, switching between nozzles can be done quicker.

In an embodiment, when the tertiary print head takes over the printing job of at least one of the nozzles of the primary or secondary print head, it may happen that a corresponding nozzle of the still printing primary or secondary print head or the tertiary print head also shows unsatisfactory behaviour. In such a case, the remaining nozzle will be used to continue printing without alternating between two print heads. Preferably, the method includes providing a warning signal if at most one nozzle of a group of corresponding nozzles is available for printing as described above, because the risk of a missing droplet may become undesirably high.

Based on a warning signal, printing may be temporarily stopped and/or maintenance may be carried out, e.g. by carrying out an automated maintenance process using a maintenance unit, such as a wiper, or maintenance personnel may be warned to check the system manually.

The second aspect of the invention further relates to a method for printing a pattern on a substrate in which use is made of an inkjet system according to the second aspect of the invention, wherein the method comprises the following steps:
  measuring the printing performance of a nozzle;
  comparing the measured printing performance of corresponding nozzles of a primary print head and its secondary, and tertiary if present, print head, and determining the nozzle with the best printing performance;
  printing with the nozzle having the best printing performance.

The method may be carried out regularly or even continuously in order to minimize the risk of the printing performance dropping below an undesired level. Printing may even regularly be suspended temporarily in order to allow the method to be carried out, such that printing can subsequently be continued with the nozzle having the best printing performance.

This has the advantage that always the best performing nozzle is used for printing, so that accuracy and reliability are increased.

Embodiments of the second aspect according to the invention may be defined by the following clauses with prefix 971:

971_1. An inkjet system comprising:
  a print head assembly with multiple print heads, wherein each print head comprises at least one nozzle from which droplets of ink fluid can be jetted towards the substrate in a jetting direction, and wherein the multiple print heads together define a printing plane perpendicular to the jetting direction,
  a substrate holder to hold the substrate,
  wherein the substrate holder is moveable relative to the print head assembly in a printing direction parallel to the printing plane,
  and wherein each nozzle has a virtual printing line on the substrate on which ink fluid droplets can be deposited when the substrate moves relative to the print head assembly in the printing direction only,
  characterized in that
  the multiple print heads comprise at least one primary print head, each primary print head having an associated secondary print head arranged at a distance from the primary print head in the printing direction, wherein each nozzle of a primary print head has a corresponding nozzle at the associated secondary print head, and wherein a primary print head and its associated secondary print head are arranged with respect to each other such that the virtual printing lines of corresponding nozzles substantially lie at the same position.

971_2. An inkjet system according to clause 971_1, wherein each print head comprises a row of nozzles, said row being positioned non-perpendicular to the printing direction, preferably at an angle of 45 degrees relative to the printing direction.

971_3. An inkjet system according to clause 971_1 or 971_2, wherein each primary print head has an associated tertiary print head arranged at a distance from the primary and secondary print head in the printing direction, wherein each nozzle of a primary print head has a corresponding nozzle at the associated tertiary print head, and wherein a primary print head and its associated tertiary print head are arranged with respect to each other such that the virtual printing lines of corresponding nozzles substantially lie at the same position.

971_4. An inkjet system according to one or more of the previous 971_clauses, wherein the print head assembly comprises a print head holder for holding the multiple print heads.

971_5. An inkjet system according to clause 971_4, wherein the print head holder is supported at three distinct locations only.

971_6. An inkjet system according to one or more of the previous 971_clauses, wherein the print head assembly is kept stationary and the substrate holder is moveable.

971_7. An inkjet system according to clause 971_6, wherein the dimension of the printing plane in a direction perpendicular to the printing direction is at least as large as the largest allowable substrate dimension in said direction that can be handled by the substrate holder.

971_8. An inkjet system according to clause 971_4, wherein each print head has an associated print head positioning device arranged between said print head and the print head holder for positioning said print head relative to the print head holder, thereby allowing to align primary print heads with their associated secondary print heads such that the virtual printing lines of corresponding nozzles lie at the same position.

971_9. An inkjet system according to clause 971_8, wherein each print head positioning device comprises a base member releasably mountable to the print head holder, and connected to the base member a body holding the print head, which body is moveable with respect to the base member by an actuator in a plane substantially parallel to the printing plane.

971_10. An inkjet system according to clause 971_9, wherein the body is moveable with respect to the base member in a translational direction and a rotational direction.

971_11. An inkjet system according to clauses 971_2 and 971_10, wherein the translational direction is perpendicular to the direction in which the row extends.

971_12. An inkjet system according to clause 971_9, wherein the body is connected to the base member via elastic hinges such that the body is only moveable relative to the base member in said plane parallel to the printing plane.

971_13. An inkjet system according to clause 971_9, wherein each print head is electrically connected to the print head holder via the base member of the associated print head positioning device.

971_14. An inkjet system according to clause 971_9, wherein pressure is supplied from the print head holder to each print head via the base member of the associated print head positioning device.

971_15. An inkjet system according to clause 971_14, wherein the print head holder comprises a chamber for applying an underpressure to one or more of the print heads, said chamber being connected to said print heads via the base member of the associated print head positioning devices.

971_16. An inkjet system according to clause 971_14, wherein the print head holder comprises a chamber for applying an overpressure to one or more print heads, said chamber being connected to said print heads via the base member of the associated print head positioning devices.

971_17. An inkjet system according to one or more of the previous 971_clauses, wherein the print head holder comprises a cooling unit to provide cooling to predefined parts of the print head holder and/or the print head.

971_18. An inkjet system according to clause 971_8, wherein the unit formed by the print head and print head positioning device comprises a visual indicator to indicate the status of the unit, thereby allowing to distinguish at least between a properly functioning print head and an improperly functioning unit which needs to be replaced.

971_19. An inkjet system according to clause 971_8, wherein the print head positioning device has a symmetric configuration to minimize thermal distortions.

971_20. An inkjet system according to clause 971_4, wherein each print head comprises driving electronics, wherein the print heads and the print head holder are configured such that the driving electronics are arranged on a part of the print head extending from the print head holder, and wherein the print head holder comprises a thermal shielding, preferably in the form of a thermally isolating layer, on a surface facing towards the driving electronics in order to minimize heat transport to the driving electronics.

971_21. An inkjet system according to clause 971_4, wherein the print head holder comprises a thermal shielding, preferably in the form of a thermally isolating layer, on a surface facing towards the substrate during printing to minimize heat transport to the substrate.

971_22. An inkjet system according to clause 971_4, wherein the print head holder comprises composite material, e.g. carbon fibre reinforced plastic, in order to minimize thermal expansion.

971_23. An inkjet system according to clause 971_8, wherein a droplet detection device is provided for detecting the position of the droplets jetted on a substrate in a direction perpendicular to the printing direction.

971_24. An inkjet system according to clause 971_23, wherein a calibration unit is provided which based on the output of the droplet detection device drives the respective print head positioning devices in order to align the primary print heads with respect to each other and to align the secondary print heads with respect to their associated primary print head.

971_25. An inkjet system according to clause 971_23, wherein the droplet detection device is also configured for detecting the position of the droplets jetted on a substrate in the printing direction.

971_26. An inkjet system according to clause 971_24 and 971_25, wherein the calibration unit is configured to determine timing information for each nozzle which enables to accurately time the firing of a nozzle in order to get a droplet ejected from said nozzle at the required location.

971_27. An inkjet system according to clause 971_23, wherein the droplet detection device emits and detects light at a frequency that is easily absorbed by the ink fluid and not by the substrate.

971_28. An inkjet system according to clause 971_23, wherein the droplet detection unit is arranged next to the print head assembly in the printing direction.

971_29. An inkjet system according to clause 971_23, wherein the droplet detection unit is a line scanner, which scans the substrate surface while the substrate moves relative to the droplet detection unit.

971_30. An inkjet system according to clause 971_23, wherein the droplet detection unit comprises multiple optical units which each are able to scan a portion of the substrates surface, wherein the multiple optical units each have a detection range which at least partially overlaps with the detection range of an adjacent optical unit, and wherein the detection ranges are combined electronically or by using software to act as a single optical unit.

971_31. An inkjet system according to clause 971_23, wherein the droplet detection unit is supported by a stable and stiff supporting member, which is preferably made of composite material with high thermal stability, e.g. carbon fibre reinforced plastic.

971_32. A method for accurately positioning print heads relative to each other, which method at least comprises the steps of:
  printing on a test substrate using all print heads;
  obtaining an image of the printed test substrate by a droplet detection unit;
  determining the centre of mass for each printed droplet from the obtained image;
  comparing the determined centre of mass with the desired centre of mass;
  determining position adjustment information for each print head from the comparison; and
  adjusting the position of the print heads relative to a print head holder based in the position adjustment information.

971_33. A printing method for printing a pattern on a substrate, in which use is made of an inkjet system according to clause 971_3, characterized in that the method comprises the following steps:
  alternatingly printing with the at least one primary print head and its associated secondary print head;
  while printing with the primary or the associated secondary print head, measuring the printing performance of each nozzle of the other one of the primary or associated secondary print head, i.e. the non-printing primary or associated secondary print head;

predicting a future printing performance of each nozzle from the measured printing performance;

in case the predicted future printing performance of a nozzle is unsatisfactory, stop printing with said nozzle and continue printing with a corresponding nozzle of the tertiary print head until the printing performance of said nozzle and the predicted future printing performance have improved to a desired level.

971_34. A printing method for printing a pattern on a substrate, in which use is made of an inkjet system according to clause 971_1, characterized in that the method comprises the following steps:

measuring the printing performance of corresponding nozzles of a primary print head and its secondary, and tertiary if present, print head;

comparing the printing performance of the corresponding nozzles, and determining the nozzle with the best printing performance;

printing with the nozzle having the best printing performance.

Now a third aspect of the invention will be addressed.

A third aspect of the invention relates to a hot-melt ink dosing system. A hot-melt ink is a material that is jettable from an inkjet system. Because an inherent property of a hot-melt ink is that it is solid at normal room temperatures, it needs to be heated to an elevated temperature to melt, so that it can be jetted towards a substrate with an inkjet system after which the ink can solidify on the substrate to form a desired pattern on the substrate.

Compared with aqueous inks, hot-melt inks have some challenges relating to the supply of the hot-melt ink to print heads of an inkjet system. One of the challenges is to do this in a reliable manner, such that at any time during the printing operation of the inkjet system enough properly prepared hot-melt ink is available for the print heads to jet, i.e. enough hot-melt ink has the right predetermined operating temperature.

A further challenge may be that while doing this, the hot-melt ink may age due to the applied thermal load to get and keep the hot-melt ink at the predetermined operating temperature, which means that the properties of the hot-melt ink change undesirably. Aging is especially a problem when the number of print heads increases, because this typically results in a large size reservoir and thus a large amount of ink which is kept at an elevated temperature for a longer period of time. From the reservoir, the hot-melt ink is then supplied to the respective print heads via corresponding supply lines.

Another disadvantage of having a large reservoir is that it takes a relatively long time for the system to heat the corresponding large amount of hot-melt ink during a start-up of the system.

It is therefore an object of the third aspect of the invention to provide a hot-melt ink dosing system in which the risk of aging of the hot-melt ink is reduced while ensuring that hot-melt ink at the predetermined operating temperature is available when required.

The object of the invention is achieved by providing a hot-melt ink dosing system according to clause 972_1.

The circulation of the hot-melt ink in the closed circuit past the fluid connections has the advantage that the required size of the reservoir is substantially independent of the amount of print heads connected to the hot-melt ink dosing system, while at the same time the predetermined operating temperature of the circulating hot-melt ink can easily be maintained for reliability purposes with respect to prior art hot-melt ink systems in which the hot-melt ink is substantially stationary. It is the length of the fluid line of the closed circuit and the amount of fluid connections that need to be adjusted to the amount and size of print heads. The size of the reservoir can then be designed for the estimated consumption rate of the respective print heads and possibly for the desired replenishing rate to minimize the amount of melted hot-melt ink in the dosing system.

In an embodiment, the reservoir is connectable to a hot-melt ink cartridge containing a predetermined amount of solid hot-melt ink to replenish the closed circuit. The heating system preferably comprises a separate heating element to supply heat to the hot-melt ink cartridge when connected to the reservoir, so that the hot-melt ink can be melted and supplied to the reservoir in the liquid phase. A control system may be provided which controls said heating element in dependency of the amount of hot-melt ink circulating in the closed circuit. The control system may be configured to replenish the closed circuit with melted hot-melt ink when the amount of hot-melt ink in the closed circuit drops below a predetermined minimum value, so that hot-melt ink is only subjected to a thermal load if required by the consumption of the inkjet system. This further reduces the chance of the hot-melt ink changing properties due to aging, because the amount of hot-melt ink in liquid phase in the dosing system is relatively low and thus the average residence time in the hot-melt ink dosing system is low.

A relatively small amount of liquid hot-melt ink in the dosing system further has the advantage that the start-up time of the system, in which the hot-melt ink in the closed circuit has to be melted, is reduced.

In order to measure the amount of hot-melt ink in the closed circuit, the dosing system may comprise a level sensor to measure the level of hot-melt ink in the reservoir. The output of the level sensor is then supplied to the control system which in turn drives the heating system in dependency thereof.

In an embodiment, the level sensor is configured to detect whether the level of hot-melt ink in the reservoir is above or below a predetermined minimum level, wherein the level sensor comprises a tubular measuring chamber having a bottom open end arranged at a height in the reservoir corresponding to the predetermined minimum level, an air volume displacing device connected to the measuring chamber to supply a predetermined volume of air to the measuring chamber, and a pressure sensor to measure an air-pressure difference between an air-pressure in the measuring chamber and an air-pressure in the reservoir above the hot-melt ink.

Supplying the predetermined volume of air to the measuring chamber with the air volume displacing device will result in a pressure difference between the air-pressure in the measuring chamber and the air-pressure in the reservoir above the hot-melt ink if the level of hot-melt ink in the reservoir is above the minimum level, and will not result in a pressure difference between the air-pressure in the measuring chamber and the air-pressure in the reservoir above the hot-melt ink if the level of hot-melt ink in the reservoir is below the minimum level. Hence, regularly supplying the predetermined volume of air to the measuring chamber and measuring the pressure difference provides information about the level of hot-melt ink in the reservoir being below or above the predetermined minimum level based on which it can be decided by a control system to replenish the hot-melt ink.

In an embodiment, when the level of hot-melt ink drops below the predetermined minimum level, a predetermined amount of hot-melt ink can be automatically provided to the reservoir from the hot-melt ink cartridge. In that case, it is preferred that the amount of hot-melt ink in the cartridge corresponds to the predetermined amount. However, alternatively, the heating system may be operated to melt the hot-melt ink in the cartridge until the level in the reservoir has risen to a predetermined maximum level. To make this possible, use can be made of a similar level sensor as described above for the minimum level, so that the level sensor is configured to detect whether the level of hot-melt ink in the reservoir is above or below a predetermined maximum level, wherein the level sensor comprises a tubular measuring chamber having an open end arranged at a height in the reservoir corresponding to the predetermined maximum level, an air volume displacing device connected to the measuring chamber to supply a predetermined volume of air to the measuring chamber, and a pressure sensor to measure an air-pressure difference between an air-pressure in the measuring chamber and an air-pressure in the reservoir above the hot-melt ink.

Because the predetermined operating temperature of a hot-melt ink can be above the 100 degrees Celsius and/or the hot-melt ink may in some cases be very aggressive, i.e. have a low pH, the level sensor needs to be able to cope with these conditions. The abovementioned type of sensors are very suitable to be used in these environments due to the use of air-pressure in combination with static components. As a result, the level sensor is reliable due to a lack of moving parts. Further, electrical components, e.g. for the pressure sensor and the driving electronics for the air volume displacing device can be situated at a safe distance from the reservoir and be connected to the measuring chamber and the reservoir by tubing, thereby providing an explosion and spark-free level sensor. The volume of said tubing is preferably small compared to the volume of the measuring chamber.

A further advantage of the level sensor may be that the level sensor is independent of hot-melt ink material and/or temperature.

The components which may get into contact with the hot-melt ink, such as the measuring chamber can be made of a suitable material that is inert to the hot-melt ink, e.g. that is capable of withstanding corrosion.

In an embodiment, the reservoir has a surface-area-to-volume ratio of at least 50 [l/m], preferably at least 100 [l/m] and most preferably at least 150 [l/m]. This is advantageous as the heating system is usually configured to apply heat to the reservoir via the outer surface of the reservoir, so that the larger the surface-area-to-volume ratio of the reservoir, the faster the volume inside the reservoir is heated through the outer surface. As a large surface-area-to-volume ratio typically results in one of the dimensions getting quite large, the reservoir can be folded to get a U-shaped cross-section, thereby keeping the overall dimensions of the reservoir within predetermined values. Preferably, the reservoir is configured such that inside the reservoir the maximum distance to the nearest wall of the reservoir is at most 10 mm, preferably at most 5 mm.

The hot-melt ink cartridges are preferably replaceable units, which are replaced by a full cartridge after being emptied. The reservoir may be configured to be connectable to more than one cartridge at the same time, so that for instance each time the level in the reservoir drops below a predetermined minimum level, a cartridge can be emptied into the reservoir without requiring to manually replace the cartridges immediately. Manual replacement is then only required when the last cartridge has been emptied.

In an embodiment, the hot-melt ink cartridge when connected to the reservoir has a bottom opening in fluid communication with the reservoir, so that melted hot-melt ink will automatically flow towards the reservoir due to gravity forces. Preferably, a spacer is positioned inside the hot-melt ink cartridge at a distance above the opening between solid hot-melt ink and the opening, wherein the spacer has a surface area at least as large as the opening, and wherein the spacer is arranged inside the hot-melt ink cartridge such that melted hot-melt ink has to flow around the spacer towards the opening. As a result, it is prevented that a vacuum is created in the cartridge which would prevent the hot-melt ink from flowing out of the cartridge. Hence, emptying of the cartridges can be ensured, which makes the dosing system more reliable when used in an inkjet system.

In an embodiment, the spacer is a plate with ridges, which ridges automatically provide the desired distance between plate and bottom of the hot-melt ink cartridge.

In an embodiment, the spacer is a plate with sideways extending protrusions to provide a desired distance between plate and sidewall of the hot-melt ink cartridge.

In an embodiment, the hot-melt ink cartridge is connectable to a connection element of the reservoir, wherein the connection element comprises a siphon to provide a gas separation between air inside the reservoir and air outside the reservoir. Even in case no cartridge is connected to the reservoir, fumes or gases due to the relatively high temperature inside the reservoir are not able to escape from the reservoir through the connection element thereby preventing a hazardous situation for other components or people working near the dosing system.

In an embodiment, the dosing valve is operated by air-pressure, which provides the same advantages as the level sensor as due to the use of air-pressure, the actuation of the dosing valves is explosion and spark-free.

The third aspect of invention also relates to a method for dosing hot-melt ink to multiple print heads of an inkjet system, said method comprising the following steps:
heating a portion of hot-melt ink to a predetermined operating temperature to allow the hot-melt ink to flow;
circulating the heated hot-melt ink in a closed circuit;
tap heated hot-melt ink from the closed circuit to a print head if required.

In an embodiment, the method further comprises the step of replenishing the hot-melt ink in case the amount of hot-melt ink in the closed circuit drops below a predetermined minimum value. Preferably, the replenishing stops when the amount of hot-melt ink in the closed circuit reaches a predetermined maximum value.

The third aspect of invention also relates to a level sensor to detect whether the level of hot-melt ink in the container is above or below a predetermined level, wherein the level sensor comprises a tubular measuring chamber having an open end arrangeable at a height in the container corresponding to the predetermined level, an air volume displacing device connected to the measuring chamber to supply a predetermined volume of air to the measuring chamber, and a pressure sensor to measure an air-pressure difference between an air-pressure in the measuring chamber and an air-pressure in the container above the hot-melt ink.

The third aspect of invention further relates to a hot-melt ink cartridge for an inkjet system, comprising an opening, wherein a spacer is positioned inside the hot-melt ink cartridge at a distance from the opening between solid hot-melt ink and the opening, wherein the spacer has a surface area at least as large as the opening, and wherein the spacer is arranged inside the hot-melt ink cartridge such that melted hot-melt ink has to flow around the spacer towards the opening to leave the hot-melt ink cartridge.

The third aspect of invention further relates to an inkjet system, in particular a drop-on-demand inkjet system comprising a hot-melt ink dosing system according to the invention.

Different aspects of the invention may be combined with each other when conceivable.

Embodiments of the third aspect according to the invention may be defined by the following clauses with prefix 972:

972_1. A hot-melt ink dosing system for dosing hot-melt ink to multiple print heads of an inkjet system, comprising:
- a closed circuit including a fluid line, a reservoir, a pump and a heating system, wherein the reservoir is arranged in the fluid line and configured to hold hot-melt ink, wherein the pump is arranged in the fluid line and configured to circulate hot-melt ink in the closed circuit, and wherein the heating system is configured to heat the hot-melt ink in the closed circuit to a predetermined operating temperature allowing the hot-melt ink to flow in the closed circuit;
- a fluid connection per print head, which fluid connection is connected to the fluid line of the closed circuit, wherein each fluid connection comprises a dosing valve to dose the amount of hot-melt ink supplied to the respective print head.

972_2. A hot-melt ink dosing system according to clause 972_1, wherein the reservoir is connectable to a hot-melt ink cartridge containing an amount of hot-melt ink to replenish the closed circuit with hot-melt ink.

972_3. A hot-melt ink dosing system according to clause 972_2, wherein the heating system comprises a heating element capable of supplying heat to the hot-melt ink cartridge in case the reservoir is connected to the hot-melt ink cartridge.

972_4. A hot-melt ink dosing system according to clause 972_1, comprising a level sensor to detect the level of hot-melt ink inside the reservoir.

972_5. A hot-melt ink dosing system according to clause 972_4, wherein the level sensor is configured to detect whether the level of hot-melt ink in the reservoir is above or below a predetermined minimum level, wherein the level sensor comprises a tubular measuring chamber having an open end arranged at a height in the reservoir corresponding to the predetermined minimum level, an air volume displacing device connected to the measuring chamber to supply a predetermined volume of air to the measuring chamber, and a pressure sensor to measure an air-pressure difference between an air-pressure in the measuring chamber and an air-pressure in the reservoir above the hot-melt ink.

972_6. A hot-melt ink dosing system according to clause 972_4, wherein the level sensor is configured to detect whether the level of hot-melt ink in the reservoir is above or below a predetermined maximum level, wherein the level sensor comprises a tubular measuring chamber having an open end arranged at a height in the reservoir corresponding to the predetermined maximum level, an air volume displacing device connected to the measuring chamber to supply a predetermined volume of air to the measuring chamber, and a pressure sensor to measure an air-pressure difference between an air-pressure in the measuring chamber and an air-pressure in the reservoir above the hot-melt ink.

972_7. A hot-melt ink dosing system according to clause 972_1, wherein the reservoir has a surface-area-to-volume ratio of at least 50 [l/m], preferably at least 100 [l/m] and most preferably at least 150 [l/m].

972_8. A hot-melt ink dosing system according to clause 972_7, wherein the reservoir has a U-shaped cross-section.

972_9. A hot-melt ink dosing system according to clause 972_7, wherein the reservoir is configured such that inside the reservoir the maximum distance to the nearest wall of the reservoir is at most 10 mm, preferably at most 5 mm.

972_10. A hot-melt ink dosing system according to clause 972_2, comprising at least one hot-melt ink cartridge.

972_11. A hot-melt ink dosing system according to clause 972_10, wherein, when the hot-melt cartridge is connected to the reservoir, the hot-melt ink cartridge comprises an opening in the bottom of the hot-melt ink cartridge such that melted hot-melt ink is able to flow into the reservoir due to gravity forces, wherein a spacer is positioned inside the hot-melt ink cartridge at a distance from the opening to be arranged in between solid hot-melt ink and the opening, wherein the spacer has a surface area at least as large as the opening, and wherein the spacer is arranged inside the hot-melt ink cartridge such that melted hot-melt ink has to flow around the spacer towards the opening.

972_12. A hot-melt ink dosing system according to clause 972_11, wherein the spacer is a plate with ridges, which ridges automatically provide the desired distance between plate and bottom of the hot-melt ink cartridge.

972_13. A hot-melt ink dosing system according to clause 972_11, wherein the spacer is a plate with sideways extending protrusions to provide a desired distance between plate and sidewall of the hot-melt ink cartridge.

972_14. A hot-melt ink dosing system according to clause 972_2, wherein the hot-melt ink cartridge is connectable to a connection element of the reservoir, and wherein the connection element comprises a siphon to provide a gas separation between air inside the reservoir and air outside the reservoir.

972_15. A hot-melt ink dosing system according to clause 972_1, wherein the dosing valve is operated by air-pressure.

972_16. A method for dosing hot-melt ink to multiple print heads of an inkjet system, said method comprising the following steps:
- heating a portion of hot-melt ink to a predetermined operating temperature to allow the hot-melt ink to flow;
- circulating the heated hot-melt ink in a closed circuit;
- tap heated hot-melt ink from the closed circuit to a print head if required.

972_17. A method according to clause 972_16, further comprising the step of replenishing the hot-melt ink in case the amount of hot-melt ink in the closed circuit drops below a predetermined minimum value.

972_18. A method according to clause 972_17, wherein the replenishing stops when the amount of hot-melt ink in the closed circuit reaches a predetermined maximum value.

Now a fourth aspect of the invention will be addressed.

A fourth aspect of the invention relates to an inkjet system, in particular a drop-on-demand inkjet system for industrial applications.

Drop-on-demand inkjet systems are well-known, especially in the consumer market where inkjet printers for paper applications have proven to be very successful over the years. An advantage of inkjet systems over other printing techniques such as impact printing is that no direct contact is required between inkjet system and substrate to provide the substrate with a desired pattern. Also part of the success of consumer inkjet printers is that manufacturers found ways to develop small and relatively cheap inkjet printers.

Recent developments have been directed to make use of inkjet systems in other applications than traditional paper applications as well. However, these developments have not been very successful, especially not when a high accuracy and reliability is required.

Examples of applications where inkjet systems are considered to be a promising manufacturing tool due to its simplicity and speed are:
- providing etch resist masks on printed circuit boards (PCB);
- providing solder masks for PCB manufacturing;
- providing masks for electrode patterning for solar cells; or
- manufacturing of active or passive circuit components, display components, antennas and/or electronic components on substrates including flexible substrates.

Inkjet systems can be used to deposit the required mask layers or structures in a desired pattern, e.g. a pattern corresponding to the electronic wiring on a PCB. Depending on the desired line width of the electronic wiring and the size of the droplets used, a missing or misplaced droplet may have an enormous impact on the working of the electronic wiring and thus the PCB. For instance, a missing droplet may cause a wire to have a undesirably high local electrical resistance which may even cause electromigration.

Inkjet systems usually comprise a print head assembly with at least one print head, said print head being an integral unit configured to eject droplets of ink fluid from nozzles arranged in a surface of the print head towards a substrate. Misplacement of droplets may occur as a result of ink fluid that has accumulated on the surface of the print head and that interacts with the ink fluid inside the nozzle or interacts with a droplet leaving the nozzle thereby changing the intended trajectory of the fired droplet.

Missing droplets may be caused by a nozzle that is blocked by dried or solidified ink fluid. This can be solved by purging the nozzles with an overpressure which forces ink fluid out of the nozzle, thereby removing the ink fluid portion blocking the nozzle. A disadvantage is that the purging may result in ink fluid accumulating on the surface of the print head which in turn may cause misplacement of the droplets.

In order to prevent the misplacement of droplets due to ink fluid on the surface of the print head, prior art inkjet systems use a maintenance unit with a wiper, which wiper is moved relative to the surface of the print head to remove ink fluid that is present on the surface, either by moving the wiper while keeping the print head stationary, moving the print head while keeping the wiper stationary, or by moving both the wiper and print head.

A disadvantage of currently used maintenance units is that the wiping performance is unsatisfactory, for instance due to changing properties of the wiper, which may be caused by aging of the wiper. As a result, not all ink fluid may be removed from the surface of the print head during a wiping action, which negatively influences the obtainable accuracy and reliability of the inkjet system and thus limits the number of industrial applications for which the inkjet system can be used.

It is therefore an object of the fourth aspect of the invention to provide a maintenance unit with an improved wiping performance, thereby preferably resulting in a more accurate and reliable inkjet system.

According to a first subaspect of the fourth aspect of the invention, this object is achieved by providing a maintenance unit according to clause 973_1. The first subaspect of the fourth aspect of the invention is based on the insight that an important parameter of the wiping action is the force, i.e. the wiping force, with which the wiper is pressed against the surface of the print head, and that the wiping force has to be controlled in order to cope with the changing properties of the wiper. Prior art position control of the wiper can not be used to reliably control the wiping force, because when for instance the properties of the wiper change, e.g. due to aging, the wiping force with which the wiper presses against the surface of the print head is usually also undesirably changed and not corrected for as the wiper remains in the same position.

The maintenance unit according to the first subaspect of the invention is configured to apply a wiping force at a substantially predetermined value, thereby resulting in a constant wiping performance and thus a more accurate and reliable inkjet system. The substantially predetermined value of the wiping force is obtained by position control using a set point that cannot be reached by the wiper due to the presence of the print head, in combination with a limitation in the maximum applicable force of the force actuator. As a result, the controller will continuously apply the maximum force to the wiper in order to urge the wiper to the position corresponding to the set point. When for instance the properties of the wiper change, the controller will automatically change the position of the wiper, such that the maximum force is still applied by the force actuator and no change in wiping performance occurs.

When the wiper does not have to wipe, the set point generator is preferably configured to provide a set point to the controller that corresponds to a position of the wiper at a distance from the surface of the at least one print head seen in a direction perpendicular to the surface of the at least one print head. In this way, the wiper is positioned in a retracted position when no wiping action is required. Consequently, when the wiper is required to perform a wiping action, the set point generator will again provide a set point corresponding to a position of the wiper at least partially inside the at least one print head seen in the direction perpendicular to the surface of the at least one print head.

In an embodiment, the maintenance unit comprises a wiper moving device for moving the wiper, wherein the controller is connected to the wiper moving device, and wherein the controller is configured to drive the wiper moving device in order to move the wiper along the surface of the at least one print head thereby removing ink from said surface with the wiper.

Preferably, the force actuator is provided to only control the position in a direction perpendicular to the surface of the at least one print head, thereby only being able to press the wiper against the surface of the at least one print head, while the wiper moving device is only provided to move the wiper parallel to the surface of the at least one print head. In such an embodiment, the wiping action is a combination of operating the force actuator and operating the wiper moving device.

In an embodiment, the wiper is guided by a guide, i.e. moveably supported, with respect to a frame in a direction perpendicular to the surface of the at least one print head, i.e. a direction parallel to the wiping force applied by the force actuator. Preferably, the wiper is guided in said direction only. The guide defines a moving range in which the wiper is allowed to move.

In an embodiment, the maintenance unit comprises a frame, wherein the wiper moving device is configured to operate on the frame of the maintenance unit in order to move the wiper. The force actuator can then be positioned in between the frame and the wiper in order to be independently controlled with respect to the wiper moving device.

In an embodiment, the force actuator is an electromagnetic actuator, preferably a Lorentz actuator, preferably such that the force generated by the electromagnetic actuator is proportional to the current applied to the force actuator. The controller may then limit the maximum applicable force of the force actuator by limiting the current applied to the force actuator. Preferably, the current-force relationship is substantially constant in the moving range of the wiper, so that the current is representative for the applied force in the entire moving range.

In an embodiment, the guide applies no significant forces to the wiper in the direction parallel to said wiping force, or in case the guide applies a force, this force is preferably constant and independent of the position of the wiper within the moving range. As a result, once the constant force is compensated for if necessary, the force applied by the force actuator is proportional to the wiping force with which the wiper is pressed against the surface. Hence, regulating the maximum applicable force to be applied by the force actuator will automatically regulate the wiping force with which the wiper is pressed against the surface.

In an embodiment, the guide is configured to guide the wiper substantially hysteresis-free, for instance by using leaf springs, e.g. leaf springs arranged parallel with respect to each other, thereby providing a linear guide.

In an embodiment, the force actuator comprises two parts, namely a first part mounted to the frame and a second part mounted to the wiper, wherein the first and second part interact with each other in order to apply a force in between the first and second part. For instance, the first part may be a coil and the second part may be a permanent magnet interacting with the coil via respective magnetic fields.

In an embodiment, the position sensor is configured to measure the position of the wiper relative to the frame of the maintenance unit. For instance, the position sensor measures the position of the second part relative to the first part. Preferably, the distance between frame and surface of the at least one print head is known and constant, so that measuring the position of the wiper relative to the frame is representative for the position of the wiper relative to the surface of the at least one print head.

In an embodiment, the wiper moving device is configured to move the wiper in a single direction along the surface. This requires some initial alignment between the wiper moving device and the surface of the print head when the maintenance unit is provided in an inkjet system, but has the advantage that control of the wiper is relatively simple.

In an embodiment, the wiper width is larger than the width of the surface, wherein the wiper moving device is configured to move the wiper in a longitudinal direction of the surface.

The wiper moving device may additionally be configured to move the wiper in two degrees of freedom, which reduces the required alignment accuracy, but may increase the control demand.

In an embodiment, the wiper moving device is configured to move the wiper in one or more directions parallel to the surface of the at least one print head.

In an embodiment, multiple wipers with respective wiper moving devices are provided on a common wiper support frame, so that each wiper is moveable independent of the other wipers. Alternatively, the multiple wipers may be stationary mounted to the common wiper support frame, which wiper support frame as a whole is moved in order to move the wipers simultaneously. This reduces the control complexity of the maintenance unit considerably, but does not allow for individual control of the movement of the wipers.

In an embodiment, the wiper support frame is moveable in a direction, where the wiper moving devices are configured to move the respective wiper in another direction, thereby obtaining two degrees of freedom moving possibilities of the wipers while keeping the control relatively simple.

In an embodiment, the wiper support frame is controllable in a stepwise manner to position the wiper support frame relative to the print head assembly after which the wiper moving devices are driven to let the wiper carry out a wiping action while the wiper support frame remains stationary relative to the print head assembly. After performing the wiping action, the wiper support frame may be moved to another position to allow the wiper to perform a wiping action with respect to another print head. Alternatively, the wiper support frame may be configured to be moved during the wiping action to cooperate with the wiper moving device in order to provide the required movement of the wiper. The mode of operation of the wiper support frame may depend on the orientation of the print heads. In case all print heads are oriented in a similar way, the stepwise mode may be applied, but when the print heads have different orientations, it may be necessary to move the wiper support frame during the wiping action.

In an embodiment, a heating device is provided in order to heat the wiper. This is especially advantageous when the ink fluid is a hot-melt ink fluid having a melting temperature above room temperature, so that ink fluid may remain behind on the wiper, which may negatively influence the wiping performance of the wiper. By heating the wiper to a temperature above the melting temperature of the ink fluid, the ink fluid may be removed thereby improving the wiping performance of the wiper.

The first subaspect of the fourth aspect of the invention also relates to an inkjet system comprising a print head assembly and a maintenance unit for the print head assembly, said print head assembly comprising at least one print head, wherein the at least one print head is an integral unit configured to eject droplets of ink fluid from nozzles arranged in a surface of the at least one print head towards a substrate, and said maintenance unit being a maintenance unit according to an embodiment of the first subaspect of the invention.

In an embodiment, the wiper of the maintenance unit is moveable between a maintenance position in which the wiper is able to perform a wiping action with respect to the at least one print head, and a non-operational position in which the wiper is arranged at a distance from the print head assembly such that the maintenance unit is not interfering with normal printing activities which usually concerns the moving of a substrate below the print head assembly.

In an embodiment, the mentioned movability of the wiper is provided via the wiper moving device.

Preferably, the mentioned movability of the wiper is provided in a plane parallel to the surface of the at least one print head.

In an alternative embodiment, the wiper is provided stationary and the print head assembly is moved between an operational position in which the print head assembly is able to perform printing activities, and a maintenance position in which the print head assembly is positioned close to the maintenance unit to allow maintenance of the at least one print head by the maintenance unit.

The inkjet system may define a printing direction, which printing direction indicates the direction in which the substrates pass the print head assembly for printing purposes. In an embodiment, the movability of either the maintenance unit or the print head assembly for maintenance purposes is perpendicular to the printing direction, and preferably in a horizontal direction.

The first subaspect of the fourth aspect of the invention also relates to a method to perform maintenance on a print head of a print head assembly, said print head being an integral unit configured to eject droplets of ink fluid from nozzles arranged in a surface of the print head towards a substrate, said method comprising the following steps,
- providing a wiper which is moveable relative to the surface of the print head to remove ink from the surface of the print head,
- urging the wiper to an unreachable position inside the print head with a force actuator while moving the wiper along the surface of the print head;
- while urging the wiper to said position, keeping the maximum by the force actuator applied force below a predetermined value.

As a result, the wiping force with which the wiper is pressed against the surface of the print head is substantially constant during the wiping action, but also relative to subsequent wiping actions over time, and thus independent of property changes of the wiper.

In an embodiment, ink fluid is purged out of the nozzles prior to moving the wiper along the surface of the print head.

In an embodiment, the wiper is moved to a position away from the surface of the print head when no maintenance is to be carried out.

According to a second subaspect of the fourth aspect of the invention, the object of the invention is achieved by providing a maintenance unit for an inkjet system with a print head assembly, said print head assembly comprising at least one print head, which print head is an integral unit configured to eject droplets of ink fluid from nozzles arranged in a surface of the at least one print head towards a substrate, wherein the maintenance unit comprises a wiper, wherein the maintenance unit further comprises a force actuator to press the wiper against the surface of the at least one print head, a force measuring unit configured to determine a wiping force with which the wiper is pressed against the surface of the at least one print head, and a controller configured to control the force applied by the force actuator in dependency of an output of the force measuring unit in order to press the wiper against the surface of a print head with a predetermined wiping force.

The second subaspect of the fourth aspect of the invention is based on the insight that an important parameter of the wiping action is the force, i.e. the wiping force, with which the wiper is pressed against the surface of the print head, and that the wiping force has to be controlled in order to cope with the changing properties of the wiper. If the properties of the wiper change due to aging, the wiping force with which the wiper presses against the surface of the print head is usually also changed. The maintenance unit according to the second subaspect of the invention is configured to adjust its settings automatically, such that the wiping force is kept at a predetermined value, thereby resulting in a constant wiping performance and thus a more accurate and reliable inkjet system.

The difference between the first and second subaspect of the fourth aspect of the invention is that the more or less predetermined wiping force is obtained in different ways. In the first subaspect of the fourth aspect of the invention, smart use of position control in combination with a limited force applied by the force actuator results in a predetermined wiping force, while in the second subaspect of the fourth aspect of the invention, the predetermined wiping force is obtained by properly controlling the applied force of the force actuator.

In an embodiment, the maintenance unit comprises a wiper moving device for moving the wiper, wherein the controller is connected to the wiper moving device, and wherein the controller is configured to drive the wiper moving device such that the wiper is moved along the surface of the at least one print head thereby removing ink from said surface with the wiper In an embodiment, the wiper is guided by a guide, i.e. moveably supported, with respect to a frame in a direction parallel to the by the force actuator generatable wiping force. Preferably, the wiper is guided in said direction only. The guide defines a moving range in which the wiper is allowed to move.

In an embodiment, the wiper moving device is configured to operate on the frame of the maintenance unit in order to move the wiper. The force actuator can then be controlled independently from the wiper moving device. In an embodiment, the wiper moving device is configured to move the wiper in a direction perpendicular to the direction of the by the force actuator generatable wiping force.

In an embodiment, the guide applies no significant forces to the wiper in the direction parallel to said wiping force, or in case the guide applies a force, this force is preferably constant and independent of the position of the wiper within the moving range. As a result, once the constant force is compensated for if necessary, the force applied by the force actuator is proportional to the wiping force with which the wiper is pressed against the surface. Hence, regulating the force to be applied by the force actuator will automatically regulate the wiping force with which the wiper is pressed against the surface. It is then sufficient for the force measurement unit to directly or indirectly measure the force applied by the force actuator.

In an embodiment, the force actuator is an electromagnetic actuator, preferably a Lorentz actuator, such that the force generated by the electromagnetic actuator is proportional with the current applied to the force actuator. The force measurement unit is then able to determine the by the force actuator applied force by measuring the current applied to the force actuator. Preferably, the current-force relationship is substantially constant in the moving range of the wiper, so that the current is representative for the applied force in the entire moving range.

In an embodiment, the guide may comprise resilient members which apply a non-constant guiding force to the wiper, for instance a guiding force depending on the position of the wiper within the moving range, e.g. the guide having a spring-like behaviour. An advantage of the resilient members is that the wiper may be urged towards an equilibrium position, which may be advantageous especially in case the wiper is non-operational. However, the guiding force applied by the resilient members can be a significant disturbance force counteracting the force applied by the force actuator, so that the force applied by the force actuator to the wiper no longer is proportional to the wiping force with which the wiper is pressed against the surface of the print head.

In order to determine the wiping force with which the wiper is pressed against the surface of the print head, it may be necessary for the force measuring unit to measure a parameter representative for a guiding force applied to the wiper by the guide and combine this information with a measured force applied by the force actuator in order to determine the wiping force with which the wiper is pressed against the surface. In case the guiding force applied by the guide is dependent on the relative position of the wiper with respect to the guide, the force measuring unit may comprise a position sensor to measure said relative position. This allows the controller to drive the force actuator in such a manner that the guiding force applied by the guide can be compensated.

In other words, the guide comprises resilient members which urge the wiper towards an equilibrium position, wherein the force measuring unit is configured to determine the guiding force applied to the wiper by the guide in order to allow compensation of said guiding force by the force actuator. Preferably, the force measuring unit is configured to measure the level of deviation from the equilibrium position to determine the guiding force applied to the wiper by the guide.

In an embodiment, the force measuring unit determines the force applied by the force actuator and subtracts from that force the determined guiding force to determine the wiping force, which wiping force is supplied to the controller for control of the wiping force.

In an embodiment, the direction in which the force actuator is able to apply a force to the wiper is substantially perpendicular to the surface of the print head.

In an embodiment, the wiper moving device is configured to move the wiper in a single direction along the surface. This requires some initial alignment between the wiper moving device and the surface of the print head when the maintenance unit is provided in an inkjet system, but has the advantage that control of the wiper is simple.

In an embodiment, the wiper width is larger than the width of the surface, wherein the wiper moving device is configured to move the wiper in a longitudinal direction of the surface.

The wiper moving device may additionally be configured to move the wiper in two degrees of freedom, which reduces the required alignment accuracy, but may increase the control demand.

In an embodiment, the wiper moving device is configured to move the wiper in one or more directions parallel to the surface of the at least one print head.

In an embodiment, multiple wipers with respective wiper moving devices are provided on a common wiper support frame, so that each wiper is moveable independent of the other wipers. Alternatively, the multiple wipers may be stationary mounted to the common wiper support frame, which wiper support frame as a whole is moved in order to move the wipers simultaneously. This reduces the control complexity of the maintenance unit considerably, but does not allow for individual control of the movement of the wipers.

In an embodiment, the wiper support frame is moveable in a direction, where the wiper moving devices are configured to move the respective wiper in another direction, thereby obtaining two degrees of freedom moving possibilities of the wipers while keeping the control relatively simple.

In an embodiment, the wiper support frame is controllable in a stepwise manner to position the wiper support frame relative to the print head assembly after which the wiper moving devices are driven to let the wiper carry out a wiping action while the wiper support frame remains stationary relative to the print head assembly. After performing the wiping action, the wiper support frame may be moved to another position to allow the wiper to perform a wiping action with respect to another print head. Alternatively, the wiper support frame has to be moved during the wiping action to cooperate with the wiper moving device in order to provide the required movement of the wiper. The mode of operation of the wiper support frame may depend on the orientation of the print heads. In case all print heads are oriented in a similar way, the stepwise mode may be applied, but when the print heads have different orientations, it may be necessary to move the wiper support frame during the wiping action.

In an embodiment, a heating device is provided in order to heat the wiper. This is especially advantageous when the ink fluid is a hot-melt ink fluid having a melting temperature above room temperature, so that ink fluid may remain behind on the wiper, which may negatively influence the wiping performance of the wiper. By heating the wiper to a temperature above the melting temperature of the ink fluid, the ink fluid may be removed thereby improving the wiping performance of the wiper.

The second subaspect of the fourth aspect of the invention also relates to an inkjet system comprising a print head assembly and a maintenance unit for the print head assembly, said print head assembly comprising at least one print head, wherein the at least one print head is an integral unit configured to eject droplets of ink fluid from nozzles arranged in a surface of the at least one print head towards a substrate, and said maintenance unit being a maintenance unit according to an embodiment of the invention.

In an embodiment, the wiper of the maintenance unit is moveable between a maintenance position in which the wiper is able to perform a wiping action with respect to the at least one print head, and a non-operational position in which the wiper is arranged at a distance from the print head assembly such that the maintenance unit is not interfering with normal printing activities which usually concerns the moving of a substrate below the print head assembly.

In an embodiment, the mentioned movability of the wiper is provided via the wiper moving device.

In an alternative embodiment, the wiper is provided stationary and the print head assembly is moved between an operational position in which the print head assembly is able to perform printing activities, and a maintenance position in which the print head assembly is positioned close to the maintenance unit to allow maintenance of the at least one print head by the maintenance unit.

The inkjet system may define a printing direction, which printing direction indicates the direction in which the substrates pass the print head assembly for printing purposes. In an embodiment, the movability of either the maintenance unit or the print head assembly for maintenance purposes is perpendicular to the printing direction, and preferably in a horizontal direction.

The second subaspect of the fourth aspect of the invention also relates to a method to perform maintenance on a print head of a print head assembly, said print head being an integral unit configured to eject droplets of ink fluid from nozzles arranged in a surface of the print head towards a substrate, said method comprising the following steps,
  providing a wiper which is moveable relative to the surface of the print head to remove ink from the surface of the print head,
  moving the wiper along the surface of the print head while pressing the wiper against the surface of the print head with a force actuator,
  determining a wiping force with which the wiper is pressed against the surface of the print head by the force actuator, driving the force actuator based on the determined wiping force in order to press the wiper against the surface of the print head with a predetermined wiping force.

In an embodiment, ink fluid is purged out of the nozzles prior to moving the wiper along the surface of the print head.

In an embodiment, determining the wiper force is indirectly done by measuring a parameter of the force actuator representative for the force applied to the wiper by the force actuator when the wiper is guided by a guide introducing substantially no disturbance forces to the wiper.

In an embodiment, determining the wiper force is indirectly done by measuring a parameter of the force actuator representative for the force applied to the wiper by the force actuator and by measuring a parameter of the guide representative for the force applied to the wiper by the guide, and combining the results of both measurements when the wiper is guided by a guide introducing significant disturbance forces to the wiper during guiding of the wiper.

Embodiments of the fourth aspect according to the invention may be defined by the following clauses with prefix 973:

973_1. A maintenance unit for an inkjet system with a print head assembly, said print head assembly comprising at least one print head, which print head is an integral unit configured to eject droplets of ink fluid from nozzles arranged in a surface of the at least one print head towards a substrate, wherein the maintenance unit comprises a wiper to wipe along the surface of the at least one print head, characterized in that the maintenance unit further comprises a force actuator to apply a force to the wiper in a direction perpendicular to the surface of the at least one print head, a position sensor to measure the position of the wiper relative to the surface of the at least one print head, a set point generator for generating a set point corresponding to a desired position of the wiper relative to the surface of the at least one print head seen in a direction perpendicular to the surface of the at least one print head, and a controller to drive the force actuator in dependency of an output of the position sensor and the set point, wherein, in order to wipe along the surface of the at least one print head, the set point generator is configured to output a set point corresponding to a position in which the wiper is at least partially inside the at least one print head, and wherein the controller is configured to limit the maximum applicable force of the force actuator to a predetermined value.

973_2. A maintenance unit according to clause 973_1, wherein the maintenance unit comprises a wiper moving device for moving the wiper, and wherein the controller is configured to drive the wiper moving device such that the wiper is moved along the surface of the at least one print head.

973_3. A maintenance unit according to clause 973_1, wherein the maintenance unit comprises a frame and a guide to guide movement of the wiper with respect to the frame in a direction parallel to the wiping force.

973_4. A maintenance unit according to clause 973_2 and 973_3, wherein the wiper moving device is configured to operate on the frame to move the wiper.

973_5. A maintenance unit according to clause 973_1, wherein the force actuator is an electromagnetic actuator, preferably a Lorentz actuator.

973_6. A maintenance unit according to clause 973_3, wherein the guide is configured to guide movement of the wiper without applying significant forces to the wiper or the guide guides movement of the wiper while applying a constant force to the wiper.

973_7. A maintenance unit according to clause 973_2, wherein the wiper moving device is configured to move the wiper in two degrees of freedom in a plane parallel to the surface of the at least one print head.

973_8. A maintenance unit according to clause 973_1, wherein multiple wipers are arranged on a common wiper support frame.

973_9. A maintenance unit according to clause 973_8, wherein respective wiper moving devices are provided in between the respective wiper and the support frame, such that movement of each wiper can individually be controlled by the controller.

973_10. A maintenance unit according to clause 973_8, wherein the wiper support frame is moveable relative to the print head assembly in one direction only, and wherein the wiper moving devices on the wiper support frame are configured to move the respective wiper in a direction different from said one direction of the wiper support frame such that the wiper is moveable in a two dimensional plane parallel to the surface of the at least one print head.

973_11. A maintenance unit according to clause 973_1, comprising a heating device to heat the wiper in order to melt ink fluid that has accumulated on the wiper, thereby removing the ink fluid from the wiper.

973_12. A maintenance unit for an inkjet system with a print head assembly, said print head assembly comprising at least one print head, which print head is an integral unit configured to eject droplets of ink fluid from nozzles arranged in a surface of the at least one print head towards a substrate, wherein the maintenance unit comprises a wiper, characterized in that the maintenance unit further comprises a force actuator to press the wiper against the surface of the at least one print head, a force measuring unit configured to determine a wiping force with which the wiper is pressed against the surface of the at least one print head, and a controller configured to control the force applied by the force actuator in dependency of an output of the force measuring unit in order to press the wiper against the surface of a print head with a predetermined wiping force.

973_13. An inkjet system comprising a print head assembly with at least one print head, which print head is an integral unit configured to eject droplets of ink fluid from nozzles arranged in a surface of the at least one print head towards a substrate, wherein the inkjet system further comprises a maintenance unit according to one or more of clauses 973_1-973_12 to perform maintenance on the at least one print head.

973_14. An inkjet system according to clause 973_13, wherein the wiper of the maintenance unit is moveable between an operational position in which the wiper is able to perform a wiping action with respect to the at least one print head, and a non-operational position in which the wiper is arranged at a distance from the print head assembly, such that the maintenance unit is not interfering with normal printing activities.

973_15. An inkjet system according to clause 973_14, wherein a printing direction is defined which corresponds to a direction in which substrates pass the print head assembly for printing purposes, and wherein the maintenance unit is moveable in a horizontal direction perpendicular to the printing direction.

973_16. A method to perform maintenance on a print head of a print head assembly, said print head being an integral unit configured to eject droplets of ink fluid from nozzles arranged in a surface of the print head towards a substrate, said method comprising the following steps:

providing a wiper which is moveable along the surface of the print head to remove ink from said surface;

urging the wiper to an unreachable position inside the print head with a force actuator while moving the wiper along the surface of the print head< while urging the wiper to said position, keeping the maximum by the force actuator applied force below a predetermined value.

973_17. A method to perform maintenance on a print head of a print head assembly, said print head being an integral unit configured to eject droplets of ink fluid from nozzles arranged in a surface of the print head towards a substrate, said method comprising the following steps:

providing a wiper which is moveable along the surface of the print head to remove ink from said surface;

moving the wiper along the surface of the print head while pressing the wiper against the surface of the print head with a force actuator;

determining a wiping force with which the wiper is pressed against the surface of the print head by the force actuator;

driving the force actuator based on the determined wiping force in order to press the wiper with a predetermined wiping force against the surface of the print head.

973_18. A method according to clause 973_16 or 973_17, wherein ink fluid is purged out of the nozzles prior to moving the wiper along the surface of the print head.

Now a fifth aspect of the invention will be addressed.

A fifth aspect of the invention relates to an inkjet system and method for printing an ink pattern on a substrate by using an inkjet system and based on a received pattern layout. The method can be applied to any situation in which homogenous, smooth-walled features in a print pattern are required. The ink pattern is a two dimensional pattern. In particular, the ink pattern is an integrated circuit (IC) pattern. An inkjet technology is applied to print the ink pattern.

Integrated circuit (IC) printing, which includes a printing of a printed circuit board, is an emerging technology that attempts to reduce the costs associated with IC production by replacing expensive lithographic processes with simple printing operations. By printing an IC pattern directly on the substrate rather than using the delicate and time-consuming lithography processes used in conventional IC manufacturing, an IC printing system can significantly reduce IC production costs. The printed IC pattern can either comprise actual IC features (i.e., elements will be incorporated into the final IC, such as the gates and source and drain regions of thin film transistors, signal lines, opto-electronic device components, etc. or it can be a mask for subsequent semiconductor processing (e.g., etch, implant, etc.).

Typically, IC printing involves depositing a print solution by raster bitmap along a single print travel axis (the "printing direction") across a solid substrate. Print heads, and in particular the arrangements of the ejector(s) incorporated in those printheads, are optimised for printing along this print travel axis. Printing of an IC pattern takes place in a raster fashion, with the printhead making "printing passes" across the substrate as the ejector(s) in the printhead dispense individual droplets of print solution onto the substrate. Generally, at the end of each printing pass, the printhead makes a perpendicular shift relative to the print travel axis before beginning a new printing pass. The printheads continues making printing passes across the substrate in this manner until the IC pattern has been fully printed.

Once dispensed from the ejector(s) of the print head, print solution droplets attach themselves to the substrate through a wetting action and proceed to solidify in place. The size and profile of the deposited material is guided by competing processes of solidification and wetting. In dependence of a type of ink, the ink solidifies by polymerisation, crystallisation, heat transfer by infra red radiation, etc. In the case of printing phase-change materials for etch mask production, solidification occurs when the printed drop loses its thermal energy to the substrate and reverts to a solid form. In another case, colloidal suspensions such as organic polymers and suspensions of electronic material in a solvent or carrier are printed and wet to the substrate leaving a printed feature. The thermal conditions and material properties of the print solution and substrate, along with the ambient atmospheric conditions, determine the specific rate at which the deposited print solution transforms from a liquid to a solid.

If a first droplet and a second adjacent droplet are applied onto the substrate within a time prior to the phase transformation of the first droplet, the second droplet will wet and coalesce to the first droplet in its liquid or semi-liquid state to form a continuous printed feature.

When a printed feature is printed in a single printing pass, a so called swath, in the printing direction adjacent droplets will deposited during the single printing pass and will not have time to dry between ejection events. A desired homogeneity and smooth side wall profile results when an optimal droplet coalescence occurs. However, in particular, a raster printing in a direction perpendicular to the printing direction often results in an ink pattern having a scalloped edge. An ink pattern extending in a direction perpendicular to the printing direction is typically a "multi-pass" feature; i.e., a printed feature formed by multiple passes, so called multiple swaths, of the print head. In a multi-pass feature, the droplets deposited during sequential passes of the print head are typically dry before any adjacent droplets from the next printing pass are deposited. Consequently, the drops of print solution that make up the multi-pass feature are not able to coalesce and therefore create "scalloped" feature borders. This edge scalloping can be recognised in that individual print solution droplets which are used to form the ink pattern are all clearly visible.

The edge scalloping is related to a variety of problematic issues. For example, if the IC pattern is a mask, the irregular edges of feature can result in unreliable print quality and patterning defects leading to inconsistent device performance. Perhaps more significantly, edge scalloping in an actual IC feature indicates a potentially serious underlying defect. The electronic behaviour of an IC feature is affected by its molecular structure. In particular, the molecules of organic printing fluids are typically long chains that need to self-assemble in a particular order. However, if a droplet of such printing solution solidifies before an adjacent droplet is deposited, those chains are not allowed to properly assemble, leading to a significant reduction in the electrical continuity between the two droplets. This in turn can severely diminish the performance of the device that incorporates the scalloped printed feature.

EP1.392.091 discloses a printing system and method to reduce the scalloping effect, but the printing system and the method is still not satisfying. The disclosed method separates an ink pattern into a first design layer and a second design layer. The first design layer consists of features which run parallel to a first reference axis which is aligned with the printing direction. The second design layer consists of features which run parallel to a second reference axis which is non-parallel with the printing direction. The second design layer is printed after printing the first design layer. A printed pattern can be formed by a series of printing operations, wherein the print direction of each printing operation is aligned with the parallel layout features of the design layer being printed.

A drawback of the method is that it provides no satisfying solution for ink patterns which have a curved geometry. In particular, a circular ink pattern may still have scalloped edges. IC printing includes a lot of circular ink patterns especially at connecting locations at an end of a circuit line for electrically connecting an IC component.

The general object of the present the fifth aspect of the invention is to at least partially eliminate the above mentioned drawbacks and/or to provide a useable alternative. More specific, it is an object of the fifth aspect of the invention to provide a method for printing an ink pattern, wherein the resulted ink pattern has an increased homogeneity and an improved smooth side wall. It is a specific object to obtain an ink pattern which has a more accurate outer contour.

According to the fifth aspect of invention, this object is achieved by a method for printing an ink pattern according to clause 974_1.

According to the fifth aspect of invention a method is provided for printing an ink pattern on a substrate based on a pattern layout. In a step of the method the pattern layout is separated into a discrete contour layer and a discrete inner region layer. The pattern layout is separated in at least one step into at least one discrete contour layer comprising at least one contour part. Further, the pattern layout is separated in least one discrete inner region layer comprising at least one inner region part. An imaginary X-Y plane including a first (X) and second (Y) axis is defined with respect to a used inkjet system. The first axis X is defined with respect to the ink jet system as extending in a direction perpendicular to a direction of movement of a linear movable substrate positioning stage. The second axis Y is oriented perpendicular to the first axis X and in a projection onto the inkjet system in parallel with a direction of movement of the linear movable substrate positioning stage. Each contour part of the contour layer of the pattern layout has an orientation in the imaginary X-Y plane. Each contour part of a selective part of the pattern layout has an accompanying inner region part. The at least one contour part of a selective part of the pattern layout which has an non-parallel orientation with respect to the Y-axis is printed by contour droplets prior to printing an inner region part of the inner region layer of the selective part of the pattern layout by fill-in droplets. Preferably, the at least one contour part has an orientation in parallel with the X-axis.

In the method according to the fifth aspect of the invention an inkjet system is used. The inkjet system receives a pattern layout, in particular an image file. The image file is for example a bitmap. The pattern layout can be received from an information carrier like an USB-stick, CD-rom etc. or be supplied by a network connection. The inkjet system comprises control electronics for controlling the inkjet system. The control electronics comprises software which include logic to separate a received pattern layout into a contour layer and an inner region layer. The contour layer is defined separate from the inner region layer. In the method according to the invention, the contour layer is printed in a first step, wherein the inner region layer is printed later in a next step.

The method according to the fifth aspect of the invention is based on an insight regarding an interaction mechanism between neighbouring droplets after being deposited on a substrate. The interaction mechanism is a relevant factor in the finally obtained accuracy of the ink pattern.

An ink pattern is built up by many adjacent droplets which should recombine to get a desired shape. In an inkjet system, the droplets are typically deposited in a structured way. In a printing direction, which is a direction of movement of a substrate, droplets are typically deposited in multiple swaths. The swaths are successively positioned in parallel to each other. Neighbouring droplets in a same swath have a certain interaction mechanism to each other which differs from an interaction mechanism between neighbouring droplets of successive swaths. The droplets in the swath are deposited shortly after each other to form the swath. A deposit time interval of neighbouring droplets in the same swath is typically about 0.1 msec. After a deposition of a droplet, the droplet starts to solidify and changes from a wet condition to a solid condition. The solidification takes place in a time interval after deposition and may take e.g. 10 seconds. A deposit time interval of neighbouring droplets in successive swaths is typically more than 10 seconds which is far longer than the deposit time interval of neighbouring droplets in the same swath. This time interval difference causes another flow behaviour and thus another interaction mechanism between neighbouring droplets. Due to the different interactions of droplets, the obtained ink pattern as a recombination of droplets varies over its geometry. At a first location in the ink pattern, neighbouring droplets may have started a coalescence after some milliseconds, while at a second location neighbouring droplets may have started coalescence after e.g. 10 seconds. The ink pattern has become for that reason a less accurate representation of the pattern layout.

Advantageously, this negative effect of different interaction is reduced by the method according to the invention. According to the invention, the pattern layout is separated into a contour and inner region, wherein the contour is printed before printing the inner region. The accuracy of the contour of the obtained ink pattern mainly determines whether the ink pattern is an acceptable representation of the pattern layout. By printing first the contour a more accurate outer dimension of the obtained ink pattern is achieved. Also an edge scalloping effect is reduced.

In particular, the contour is printed first by depositing contour droplets and thereafter the inner region is filled with fill-in droplets before a solidification of the ink takes place. The contour of the ink pattern mainly determines the accuracy. Advantageously, the contour is created in a relative short time such that a variety of ink flow behaviour remains limited which results in a more accurate ink pattern.

A pattern layout may represent a complete IC pattern, but may also represent a part of the IC pattern. The pattern layout may be separated in at least one step. The complete pattern layout may be separated in one step into a contour and an inner region. Alternatively, the complete pattern layout may be separated in multiple steps into at least one contour layer and at least one inner region layer. A pattern layout of a complete IC pattern may be subdivided in a set of pattern layout layers before printing. Subsequently, according to the fifth aspect of the invention each pattern layout layer is considered as an individual pattern layout and is separated into a discrete contour and inner region, wherein the contour of the pattern layout part is printed prior to the inner region of the pattern layout part.

In an embodiment of the method according to the fifth aspect of invention, the received pattern layout is separated in one step into a discrete contour and a discrete inner region. The ink pattern is printed by printing first the discrete contour and thereafter the inner region.

In an embodiment of the method according to the fifth aspect of invention, the pattern layout comprises at least two pattern layout layers which are printed in successive printing steps. Each pattern layout layer is printed by printing a contour prior to an inner region of the pattern layout layer.

In a particular embodiment of the method according to invention, the pattern layout may comprise at least two pattern layout layers, wherein a first pattern layout layer is printed at a constant X-coordinate. The complete pattern layout is subdivided in a set of pattern layout layers based on travel movements of the substrate in the inkjet system. During a first printing step, the X-coordinate is kept constant by preventing a movement of the substrate in X-direction. The subsequent second pattern layout layer is subsequently printed in a second printing step after a shift of the substrate in X-direction. The shift may be a distance of at most 100 μm, in particular at most 0.50 μm, but preferably at most 0.25 μm in X-direction. The first pattern layout layer is printed by printing first a contour and subsequently an inner region of the first pattern layout layer. Hereby, the first pattern layout layer is completely printed. Subsequently, the second pattern layout layer is printed by printing first a contour and subsequently an inner region of the second pattern layout layer. Herewith, the second pattern layout layer is completely printed after a complete printing of the first pattern layout layer. It is an advantage to complete a pattern layout layer before printing a next pattern layer by printing both the contour as the inner region, because this allows a reduction of a total of printing steps to complete the ink pattern. The complete ink pattern can be printed in a shorter printing time.

In a particular embodiment of the method according to invention, the pattern layout may comprise at least two pattern layout layers, wherein a first pattern layout layer comprises a first class of contour types and wherein a second pattern layout layer comprises a second class of contour types. A particular classification of contours in dependence of an orientation of at least a part of a contour is described hereafter. The first pattern layout layer comprising contours of the first class may be completely printed in which both the contour and the inner region are included before starting a printing step in which the second pattern layout layer is printed which comprises contours of the second class to obtain a final ink pattern which corresponds with the received pattern layout. A class of contour types may be characterised by a specific time interval for depositing ink droplets. A speed of a substrate positioning stage may correspond with the class of contour types which have to be deposed. The ink pattern may be created by successively printing the first and second pattern layout layer. Advantageously, by subdividing the received pattern layout into several pattern layout layers based on a classification of contour types, a total printing time to print the complete ink pattern may be reduced. According to the fifth aspect of the invention, the plurality of pattern layout layers are each considered as an individual pattern layout in which each individual pattern layout is separated into a discrete contour and a discrete inner region, wherein the contour of the pattern layout is printed by contour droplets prior to printing the inner region of the pattern layout by fill-in droplets.

In a particular embodiment of the method according to invention, a pattern layout may be subdivided in a set of pattern layout features before printing the ink pattern. A feature may e.g. be a connection point for an electrical component on a printed circuit board. Such a feature has typically a circular geometry. The pattern layout feature is separated into a discrete contour and a discrete inner region. The contour of the pattern layout feature is printed prior to printing the inner region of the pattern layout feature.

In an embodiment of the method according to the fifth aspect of the invention, a pattern layout is separated in a contour layer and an inner region layer. In a particular embodiment, a pattern layout may comprise only a contour. After applying the logic to separate the pattern layout, the inner region may appear to be a blank region, such that a printing of the inner region can be omitted.

In an embodiment of the method according to the fifth aspect of the invention, the contour layer of the pattern layout is printed by depositing contour droplets prior to printing the inner region layer of the pattern layout by depositing fill-in droplets. All contour parts are printed prior to an inner region part. Advantageously, no exception needs to be programmed in the control electronics for contour parts having an orientation in parallel with the Y-axis.

In an embodiment of the method according to the fifth aspect of the invention a contour print algorithm is applied for printing the contour, wherein the contour print algorithm converts the contour to a set of droplet positions. The used inkjet system comprises control electronics to control the system. The control electronics comprise software which is configured to convert a received pattern layout into a set of droplet positions. The software comprises logic for separating the pattern layout into a discrete contour and an inner region. The logic includes the contour print algorithm. By applying the contour print algorithm, the contour of a pattern layout is converted into a set of droplet positions. In a next step the inkjet system is operated to deposit contour droplets at the calculated droplet positions.

In an embodiment of the method according to the fifth aspect of the invention, the method comprises a step of defining an orientation of at least a part of a contour of the pattern layout. The orientation of the contour is defined by an angle in a plane with respect to a reference axis. In particular, the reference axis corresponds with a printing direction of the inkjet system. The printing direction of the inkjet system may be defined by a direction of movement of a substrate positioning stage which passes in a movement a printing head.

For instance, the contour or a part of a contour may be a line. The orientation of the line may be determined by measuring an angle between the line and the reference axis. The orientation of the at least part of the contour of a pattern layout may be defined by determining at least two dimensional position coordinates of the contour in a Cartesian system. The orientation may be determined by subtracting the position coordinates.

For instance, the contour or a part of the contour may be arc shaped. The orientation of the arc shaped contour may be determined by measuring an angle between a tangent line and the reference axis.

In dependence of the obtained orientation of the at least part of the contour, the at least part of the contour is subsequently classified in a corresponding contour class of a classification system.

In a subsequent step of the method a contour print algorithm is selected in dependence of the classified contour class. By applying the selected contour print algorithm, the at least part of the contour of the pattern layout is converted to a set of contour droplet positions and the contour droplets of the at least part of the contour are printed to the substrate.

By using dedicated contour print algorithms for several classes of a classification system, it is possible to take due account for an ink flow behavior which is dependent on the orientation of a part of a pattern layout. Advantageously, herewith it is possible to produce a more accurate ink pattern.

In an embodiment of the method according to the fifth aspect of the invention, a contour class is characterized by an orientation of a contour in an imaginary plane including a first X and second Y axis oriented in said plane, wherein the first axis is defined perpendicular to a linear movement of the substrate during operation, wherein the second axis Y is oriented perpendicular to the first axis and in a projection onto an inkjet system in parallel with a direction of movement of a linear movable substrate positioning stage.

In an embodiment of the method according to the fifth aspect of the invention, the classification system comprises a first contour class, a second contour class and a third contour class, wherein the first, second and third contour class include contour orientations in a first quadrant of a Cartesian system including an X and Y axis, wherein the Y-axis corresponds with a printing direction of the inkjet system which is a direction of movement of the substrate.

The first contour class (I) corresponds with a group of contour parts which are orientated in a quadrant region bounded by a direction in parallel with the X-axis and a direction under a predefined angle α with respect to the Y-axis. The first contour class I can also be indicated as an X-X'-orientation, wherein the orientation is aligned with a reference axis in X direction, the X-axis, or under an inclination with respect to the X-axis, a X'-axis.

The second contour class (II) corresponds with a group of contour parts which are orientated in the quadrant region in between the direction under the predefined angle α and a direction in parallel with the Y-axis. The second class may also be indicated as a group of contour parts having an X-Y orientation.

The third contour class (III) corresponds with a group of contour parts which are orientated in a direction in parallel with the Y-axis. The third class may also be indicated as a group of contour parts having an Y orientation.

In an embodiment of the method according to the fifth aspect of the invention, the classification system comprises additional classes which corresponds with orientations in the second, third and/or fourth quadrant of the Cartesian system.

In an embodiment of the method according to the fifth aspect of the invention, the method comprises a step of converting a defined orientation of at least a part of a contour of the pattern layout to an orientation which falls within the first quadrant. The conversion to the first quadrant may be obtained by mirroring an orientation about the first and/or second reference axis. After applying a selected contour print algorithm, the at least part of the contour of the pattern layout is converted to a set of contour droplet positions. Subsequently, the set of contour droplet positions which are determined for the first quadrant are reconverted to the second, third or fourth quadrant. After the reconversion, the final set of positions are obtained and the contour droplets of the at least part of the contour are ready to be printed to the substrate.

In an embodiment of the method according to the fifth aspect of the invention, the contour print algorithm comprises a coverage algorithm for converting at least a part of the contour into a set of coverage elements before generating the set of droplet positions. In stead of a direct conversion in one step from the pattern layout to a set of positions, an intermediate step is introduced to convert at least a part of a contour of a pattern layout to at least one coverage element. Subsequently, calculations defined by the algorithm are performed onto the coverage element. The coverage element may be a simplified form of the at least part of the contour. The coverage element may e.g. be a line, arc or circular element. Preferably, the coverage element is a line element, also called a strip element. Advantageously, by applying a coverage algorithm as a feature of the contour print algorithm, the contour print algorithm is simplified. A number of calculations in the contour print algorithm may be reduced by converting the at least part of the contour into the coverage elements. A calculation capacity of the control electronics is less loaded. Advantageously, the inkjet system may have an increased speed and production capacity.

In an embodiment of the method according to the fifth aspect of the invention, the contour print algorithm of the first contour class I comprises a coverage algorithm which includes at least one of the following parameters: a parameter defining a number of droplets; a parameter defining a size of droplets; a parameter defining a constant mutual distance between droplets; and a parameter defining at least one absolute droplet position.

The outcome of the coverage algorithm of the first contour class may be a strip element as a coverage element. The strip element has an orientation in X-direction. The strip element may extend in X-direction under an angle. The strip is build up with a constant mutual distance between droplets.

In an embodiment of the method according to the fifth aspect of the invention, the contour print algorithm of the second contour class comprises a coverage algorithm which includes at least one of the following parameters: a parameter defining a size of droplets; a parameter defining at least one absolute droplet position; a parameter defining a number of droplets at an X-position extending in Y direction; and a parameter defining at least one mutual distance between droplets as a function of an absolute droplet position.

The outcome of the coverage algorithm of the second contour class may be a strip element as a coverage element. The strip may be an inclined strip. Preferably, the coverage element is a strip element which has an orientation in a direction in parallel with the Y-axis.

The strip is build up with a varying mutual distance between droplets over a length of a contour. Advantageously, a varying mutual distance between the droplets allow a more accurate contour of the ink pattern.

In an embodiment of the method according to the fifth aspect of the invention, the contour print algorithm of the third contour class comprises a coverage algorithm which includes at least one of the following parameters: a parameter defining a size of droplets; a parameter defining a constant mutual droplet distance for at least a part of a contour; a parameter defining at least one absolute droplet position.

The outcome of the coverage algorithm of the third contour class may be a strip element as a coverage element. The strip element has an orientation in Y-direction. The strip element is build up with a constant mutual distance between droplets.

In an embodiment of the method according to the fifth aspect of the invention, the contour print algorithm of the first contour class comprises a coverage algorithm which includes a parameter defining a distance between a contour droplet and a fill-in droplet. Herewith it is possible to accurately position two adjacent coverage elements, wherein a ink flow effect is taken into account which occurs when two coverage elements including a certain orientation are positioned adjacent each other.

In an embodiment of the method according to the fifth aspect of the invention, an inner region print algorithm is applied for printing the inner region of the pattern layout by fill-in droplets. The inner region print algorithm converts the inner region to a set of fill-in droplets. Analogue to the above described contour print algorithm, the inner region print algorithm may also comprise a coverage algorithm for converting at least a part of the inner region into a set of coverage elements before generating the set of fill-in droplet positions. Preferably, the coverage element is a strip element having an orientation in Y-direction. In an embodiment of the method according to the fifth aspect of the invention, the contour print algorithm comprises an ink flow algorithm for taking into account an ink flow effect before generating the set of droplet positions. The ink flow effect may e.g. depend on a applied combination of ink and substrate or a time interval for depositing neighbouring droplets. Advantageously, an incorporation of the ink flow algorithm in the contour print algorithm improves an accuracy of an obtained ink pattern.

In an embodiment of the method according to the fifth aspect of the invention, both the coverage algorithm and the ink flow algorithm may be incorporated in the contour print algorithm. In a first step of the contour print algorithm a contour of a pattern layout may be converted into a certain coverage element. In a subsequent step, the coverage element is converted to a set of droplet positions, wherein due account is taken of flow behaviour of ink droplets for forming the certain coverage element in dependence of current circumstances. For instance the type of ink and substrate material may be taken into account when determining a set of droplet positions for a certain coverage element. Advantageously, an incorporation of both the coverage as the ink flow algorithm in the contour print algorithm improves an accuracy of an obtained ink pattern.

In an embodiment of the method according to the fifth aspect of the invention, the ink flow algorithm includes ink flow parameters originating from a measurement of at least one test pattern. In the method the ink flow parameters are determined by comparing the printed test pattern with a desired pattern, the pattern layout.

The test pattern may comprise at least one coverage element. In particular, the test pattern comprises a pair of coverage elements which are positioned adjacent each other to determine an ink flow effect in between paired coverage elements to define an ink flow parameter which takes account of the measured ink flow effect. The ink flow effect may be a narrowing effect or a time dependent effect which can e.g. be compensated by adjusting a droplet size or positioning. Preferably, the measurement is carried out in the inkjet system, wherein the inkjet system comprises a calibrated scanning unit for capturing an image of the printed test pattern. Advantageously, an online measurement can be carried out to determine the ink flow parameters.

In an embodiment of the method according to the fifth aspect of the invention a width of a test pattern is measured and compared with a pattern layout to determine a deficiency and to determine the ink flow parameter to compensate for the deficiency.

In an embodiment of the method according to the fifth aspect of the invention an outcome of the ink flow algorithm determines the predefined angle $\alpha$ as a boundary between the first and second class of the classification system. Advantageously, the contour print algorithm can be optimised by optimising use of different coverage elements.

In an embodiment of the method according to the fifth aspect of the invention an outcome of the ink flow algorithm determines a value of a parameter of the coverage algorithm.

Further, the fifth aspect of invention relates to an inkjet system, in particular a drop-on-demand inkjet system for industrial applications. The inkjet system is arranged for printing an ink pattern, in particular an IC pattern on a substrate. The inkjet system comprises at least one inkjet print head for ejecting a droplet of ink onto the substrate. The inkjet system comprises a substrate positioning stage for carrying and moving the substrate. The inkjet system further comprises control electronics for controlling the inkjet system. The control electronics comprise software which is configured to apply a method according to the fifth aspect of the invention for printing an ink pattern on a substrate based on a received pattern layout. The software comprises logic to separate the pattern layout into a discrete contour and a discrete inner region. The software comprises logic for extracting the discrete contour and the discrete inner region from the received pattern layout. The control electronics are programmed to print the contour of the pattern layout by contour droplets prior to printing the inner region of the pattern layout by fill-in droplets.

Embodiments according to the fifth aspect of the invention may be defined by the following clauses with prefix 974:

974_1. Method for printing an ink pattern on a substrate based on a received pattern layout by using an inkjet system, wherein the pattern layout is separated in at least one step into at least one discrete contour layer comprising at least one contour part and at least one discrete inner region layer comprising at least one inner region part, wherein the at least one contour part has an orientation in an imaginary plane including a first (X) and second (Y) axis, wherein the first axis is defined with respect to the ink jet system as extending in a direction perpendicular to a direction of movement of a linear movable substrate positioning stage and wherein the second axis is oriented perpendicular to the first axis in parallel with a direction of movement of the linear movable substrate positioning stage, wherein a contour part in the contour layer of a selective part of the pattern layout which has an non-parallel orientation with respect to the Y-axis is printed by contour droplets prior to printing an inner region of the inner region layer of the selective part of the pattern layout by fill-in droplets.

974_2. Method according to clause 974_1, wherein a contour print algorithm is applied for printing the contour, wherein the contour print algorithm converts the contour to a set of contour droplet positions.

974_3. Method according to clause 974_1 or 974_2, wherein the method comprises the steps of:
defining an orientation of the at least contour part of the pattern layout;
classifying the at least contour part in dependence of the defined orientation in a corresponding contour class of a classification system;
selecting a contour print algorithm in dependence of the classified contour class; and
printing contour droplets of the at least contour part of the pattern layout by applying the selected contour print algorithm.

974_4. Method according to clause 974_3, wherein a contour class is characterized by an orientation of a contour part in an imaginary plane including a first (X) and second (Y) axis oriented in said plane, wherein the first axis is defined with respect to an ink jet system as extending in a direction perpendicular to a direction of movement of a linear movable substrate positioning stage, wherein the second axis is oriented perpendicular to the first axis and in a projection onto the inkjet system in parallel with a direction of movement of the linear movable substrate positioning stage.

974_5. Method according to clause 974_3 or 974_4, wherein the classification system comprises a first contour class I, a second contour class II and a third contour class III, wherein the first, second and third contour class include contour orientations in a first quadrant of a Cartesian system including an X and Y axis, wherein the Y-axis corresponds with a printing direction which is in a projection onto an inkjet system in parallel with a direction of movement of a linear movable substrate positioning stage, wherein the first contour class (I) corresponds with a group of contour parts which are orientated in a quadrant region bounded by a direction in parallel with the X-axis and a direction under a predefined angle α with respect to the Y-axis; wherein the second contour class (II) corresponds with a group of contour parts which are orientated in the quadrant region in between the direction under the predefined angle α and a direction in parallel with the Y-axis; wherein the third contour class (III) corresponds with a group of contour parts which are orientated in a direction in parallel with the Y-axis.

974_6. Method according to any of the clause 974_2-974_5, wherein the contour print algorithm comprises a coverage algorithm for converting at least one contour part into a set of at least one coverage element before generating the set of droplet positions.

974_7. Method according to clause 974_6, wherein the coverage element is a strip element which has an orientation in a direction in parallel with the Y-axis.

974_8. Method according to clause 974_6 or 974_7, wherein the contour print algorithm of the first contour class (I: X-X'-orientation) comprises a coverage algorithm which includes at least one of the following parameters:
  a parameter defining a number of droplets;
  a parameter defining a size of droplets;
  a parameter defining a constant mutual distance between droplets; and
  a parameter defining at least one absolute droplet position.

974_9. Method according to any of the clauses 974_6-974_8, wherein the contour print algorithm of the first contour class I comprises a coverage algorithm which includes a parameter defining a distance between a contour droplet and a fill-in droplet.

974_10. Method according to 974_6 or 974_7, wherein the contour print algorithm of the second contour class (II: X-Y orientation) comprises a coverage algorithm which includes at least one of the following parameters:
  a parameter defining a size of droplets;
  a parameter defining at least one absolute droplet position;
  a parameter defining a number of droplets at an X-position extending in Y direction; and
  a parameter defining at least one mutual distance between droplets as a function of an absolute droplet position.

974_11. Method according to 974_6 or 974_7, wherein the contour print algorithm of the third contour class (III: Y-orientation) comprises a coverage algorithm which includes at least one of the following parameters:
  a parameter defining a size of droplets;
  a parameter defining a constant mutual droplet distance for at least a part of a contour;
  a parameter defining at least one absolute droplet position.

974_12. Method according to any of the preceding clauses, wherein the print algorithm comprises an ink flow algorithm for taking into account an ink flow effect before generating the set of droplet positions.

974_13. Method according to clause 974_12, wherein the ink flow algorithm includes at least one ink flow parameter originating from a measurement of at least one test pattern.

974_14. Method according to clause 974_13, wherein the test pattern comprises at least one coverage element.

974_15. Method according to clause 974_13, wherein the coverage element is a strip element which has an orientation in a direction in parallel with the Y-axis.

974_16. Method according to any of the clauses 974_13-974_15, wherein the test pattern comprises a pair of coverage elements which are positioned adjacent each other to determine an ink flow effect in between the paired coverage elements to define an ink flow parameter which takes account of the measured ink flow effect.

974_17. Method according to any of the clauses 974_12-974_16, wherein the measurement is carried out in the inkjet system, wherein the inkjet system comprises a calibrated scanning unit for capturing an image of a printed test pattern, wherein an ink flow parameter is determined by comparing a printed test pattern with a pattern layout.

974_18. Method according to any of the clauses 974_12-974_17, wherein a width of a test pattern is measured and compared with a pattern layout to determine a deficiency to determine the ink flow parameter to compensate for the deficiency.

974_19. Method according to any of the clauses 974_5-974_18, wherein an outcome of the ink flow algorithm determines the predefined angle α as a boundary between the first and second class.

974_20. Method according to any of the clauses 974_11-974_19, wherein an outcome of the ink flow algorithm determines a value of a parameter of the coverage algorithm.

974_21. Inkjet system, in particular a drop-on-demand inkjet system for industrial applications for printing an ink pattern on a substrate comprising
  an inkjet print head for ejecting a droplet of ink on the substrate;
  a substrate positioning stage for carrying and moving the substrate;
  a control electronics for controlling the inkjet system, wherein the control electronics are configured to carry out a method according to any of the clauses 974_1-974_19, comprising software configured to apply a method for printing an ink pattern on a substrate based on a received pattern layout, wherein the pattern layout is separated into a discrete contour and a discrete inner region, wherein the contour of the pattern layout is printed by contour droplets prior to printing the inner region of the pattern layout by fill-in droplets, wherein the software comprises logic for extracting the discrete contour and the discrete inner region from the received pattern layout.

974_22. Use of the method according to any of the clauses 974_1-974_20 to print an integrated circuit pattern, in particular a pattern layout for a printed circuit board (PCB).

Now a sixth aspect of the invention will be addressed.

A sixth aspect of the invention relates to an inkjet system, in particular an IC inkjet system for printing an integrated circuit, and a method for calibrating and controlling a substrate holder with respect to a virtual plane which is in parallel with an imaginary plane formed by a common position of a group of nozzles of a print head.

Integrated circuit (IC) printing, in particular printing of printed circuit boards, is an emerging technology that attempts to reduce the costs associated with IC production by replacing expensive lithographic processes with simple printing operations. By printing an IC pattern directly on the substrate rather than using the delicate and time-consuming lithography processes used in conventional IC manufacturing, an IC printing system can significantly reduce IC production costs. The printed IC pattern can either comprise actual IC features (i.e., elements will be incorporated into the final IC, such as the gates and source and drain regions of thin film transistors, signal lines, opto-electronic device components, etc. or it can be a mask for subsequent semiconductor processing (e.g., etch, implant, etc.).

Typically, IC printing involves depositing a print solution by raster bitmap along a single print travel axis (the "printing direction") across a substrate. Print heads, and in particular the arrangements of the ejector(s) incorporated in those printheads, are optimised for printing along this print travel axis. Printing of an IC pattern takes place in a raster fashion, with the printhead making "printing passes" across the substrate as the ejector(s) in the printhead dispense individual droplets of print solution onto the substrate. Generally, at the end of each printing pass, the printhead makes a perpendicular shift relative to the print travel axis before beginning a new printing pass. The printheads continues making printing passes across the substrate in this manner until the IC pattern has been fully printed.

A drawback in this context is that an accuracy of such IC printing system is limited. The accuracy of the IC printing system is limited due to deviations which occur during printing movements of the print head and the substrate. Deviations are typically introduced by guidances and bearings of the IC printing system.

The general object of the present the sixth aspect of invention is to at least partially eliminate the above mentioned drawbacks and/or to provide a useable alternative. More specific, it is an object of the sixth aspect of the invention to provide an inkjet system which includes a relative simple configuration but which has a high accuracy performance and a method to control a positioning of a substrate in an inkjet system with high precision.

According to the sixth aspect of the invention, this object is achieved by an inkjet system according to clause 975_1.

According to the sixth aspect of the invention, an inkjet system is provided for printing an ink pattern on a substrate. The inkjet system comprises a substrate holder for holding a substrate.

Further, the inkjet system comprises a substrate positioning stage for positioning the substrate holder in a printing direction. The printing direction is defined as a direction of travel of the substrate positioning stage about a longitudinal axis of the inkjet system. The printing direction of the inkjet system may be defined as a direction of movement of a substrate when passing a print head assembly to print a swath onto the substrate. The substrate holder is supported by the substrate positioning stage.

Further, the inkjet system comprises a stage positioning device. The substrate positioning stage is movable by the stage positioning device. In particular, the substrate positioning stage is movable in the printing direction about a long stroke of at least 0.5 m and at most 2 m.

Further, the inkjet system comprises a print head holder for holding a print head assembly which includes at least one print head for ejecting ink from a nozzle to the substrate.

The inkjet system according to the sixth aspect of the invention is improved in that the inkjet system further comprises a holder positioning device for positioning the substrate holder in at least one degree of freedom with respect to the substrate positioning stage. In particular, the substrate positioning stage is movable in at least one degree of movement about a short stroke of at least 0.5 mm and at most 10 mm, more in particular at least 2 mm and at most 8 mm. In particular, the holder positioning device is supported by the substrate positioning stage.

Advantageously, a positioning of the substrate holder with respect to the substrate positioning stage can compensate for deviations which occur during a travel of the substrate positioning stage. Such deviations from a theoretical ideal straight path of the substrate positioning stage may e.g. be caused by a deviation in straightness of a stage guidance. The occurring deviations can be measured during a travel of the substrate positioning stage and subsequently compensated by moving the substrate holder relative to the substrate positioning stage. Herewith, a held substrate in the substrate holder can be guided more accurate along a longitudinal axis of the inkjet system and passed along a print head.

Due to the fact that the substrate holder can be correctly positioned on-the-fly through control and measurement loops, the supporting substrate positioning stage itself does not need a very high accuracy. This makes a low-cost design possible. It is for instance possible to use a belt drive for driving the substrate positioning stage in the printing direction. It is possible to actively correct the substrate holder for all position errors introduced by a lower arranged substrate positioning stage due to deviations in for example a frame and guiding straightness.

An orthogonal system including an X, Y and Z-axis can be projected onto the inkjet system. An Y-axis may be defined in a longitudinal direction which corresponds with a printing direction. An X-axis may be defined in a lateral direction. The X-axis extends in a direction transversal the printing direction. In particular, the X-axis and Y-axis define a horizontal plane. A Z-axis may be defined in upwards direction. The Z-axis is an up-down axis, in particular the Z-axis defines a vertical direction. Rotational directions can be defined in relation to the X-, Y-, and Z-axis. A rotational direction about the X-axis Rx, a pitch motion, may be defined as a rotation of the substrate about the lateral axis. A rotational direction about the Y-axis Ry, a roll motion, may be defined as a rotation of the substrate about a longitudinal axis. A rotational direction about the Z-axis Rz, a yaw motion, may be defined as a rotation of the substrate about the up-down axis.

In an embodiment of the inkjet system according to the sixth aspect of the invention, the at least one degree of freedom in which the substrate holder is positioned coincidences with a direction defined by an axis of the orthogonal system. In particular, the substrate holder is movable, in particular in the printing direction, about a stroke of at most 10 mm, in particular at most 5 mm with respect to the substrate positioning stage.

In an embodiment of the inkjet system according to the sixth aspect of the invention, the least one degree of freedom in which the substrate holder is positioned with respect to the substrate positioning stage is directed in the printing direction. Typically, the at least one printhead ejects ink droplets from a nozzle at a constant frequency. To obtain an accurate ink pattern, it may be preferred to pass the substrate along the printhead at a constant speed such that the ink droplets are deposed at a regular interval. The substrate holder velocity can be controlled through a master slave control system to obtain a constant speed in which the substrate holder compensates for small speed errors along the travel of the substrate positioning stage in the longitudinal direction.

In an embodiment of the inkjet system according to an invention, the at least one degree of freedom in which the substrate holder is positioned with respect to the substrate positioning stage is directed in the upwards direction. Advantageously, the holder positioning device can compensate for deviations in the upwards or downwards direction during a travel of the substrate positioning stage.

In an embodiment of the inkjet system according to an invention, the holder positioning device positions the substrate holder in at least three degrees of freedom. In particular, the holder positioning device positions the substrate holder in upwards direction (Z-direction), in a rotational direction Ry along a longitudinal axis (Y-axis) and a rotational direction Rx along a lateral axis (X-axis).

The holder positioning device provides a possibility to orient a held substrate in the substrate holder in a virtual plane. In particular, the virtual plane coincidences with a plane in parallel with the X-Y plane of the orthogonal system which is in particular a horizontal plane. The virtual plane is arranged in parallel with an imaginary plane in which a group of nozzles is arranged. By positioning a substrate in parallel with the virtual plane, the substrate may be arranged in parallel with the imaginary plane formed by the group of nozzles. The substrate may be spaced at a constant distance from the group of nozzles which allows a more accurate positioning of ink droplets at a top surface of the substrate.

In an embodiment of the inkjet system according to the sixth aspect of the invention, the holder positioning device positions to substrate holder in all degrees of freedom with respect to the substrate positioning stage. Advantageously, the positioning device provides a full control of all possible movements of the substrate. The positioning device allows a compensation for all deviations in all directions of the substrate holder with respect to the substrate positioning stage.

In an embodiment of the inkjet system according to the sixth aspect of the invention, the holder positioning device comprises at least one holder actuator in which the at least one holder actuator positions one degree of freedom in translation. The holder actuator determines one degree of freedom while the remaining five degrees of freedom are left free. Two paired of such holder actuators allow in cooperation a positioning of the substrate holder in a rotational degree of freedom.

In an embodiment of the inkjet system according to an invention, the holder positioning device comprises at least one holder actuator and at least one holder position measurement system. In particular, the holder actuator is a voice coil actuator. The holder position measurement system may be incorporated in the holder actuator. The holder position measurement system may be a built-in encoder with an accuracy of at least 1 μm. The holder actuator has a holder actuator base which is connectable to the substrate positioning stage and a holder actuator body which is connectable to the substrate holder. The holder actuator body is movable with respect to the holder actuator base. In particular, the holder actuator body has a body member which determines only one degree of freedom of available directions of movements. In particular, the body member has an elongated portion. In particular the body member is antenna shaped. The body member allows a movement of five degrees of freedom, but resists a movement, more precisely said a translation, in a direction parallel to the elongated portion.

In an embodiment of the inkjet system according to invention the printhead holder is stationary mounted in the inkjet system. The printhead holder is fixedly connected to a frame of the inkjet system. The printhead holder may be beam-shaped. As a result, the at least one printhead is stationary mounted in the inkjet system during a printing step in which ink droplets are ejected. A necessary relative motion of a substrate with respect to a printhead during the printing step is obtained by moving the substrate holder with respect to the stationary arranged printhead holder. Advantageously, the stationary mounted printhead holder provides a more accurate inkjet system. No deviations are generated which would have occur by a moving printhead holder.

In an embodiment of the inkjet system according to invention, the print head holder comprises at least three reference marks. The three reference marks may be incorporated in one print head holder reference surface. The three reference marks define an imaginary plane, which is parallel to the imaginary plane formed by the group of nozzles of a print head. In particular, the imaginary plane has a normal vector in upwards direction, Z-direction. Advantageously, a substrate holder can be aligned e.g. by contacting with the reference surface of the print head holder to align the substrate holder with the virtual plane. After an alignment step, also called homing of the substrate holder at a homing position, the holder positioning device is programmed to control the substrate holder in parallel with the virtual plane. Particularly, during homing of the substrate holder with respect to the virtual plane, z-, y- and x-coordinates are programmed to the holder positioning device to maintain a substrate in parallel with the virtual plane about a whole printing area in which the printing area is determined by an area of nozzles.

In an embodiment of the inkjet system according to the sixth aspect of the invention, the inkjet system comprises a X-calibration element including a calibration element X-reference surface. The X-calibration element reference surface extends in the printing direction, the Y-direction, in parallel with a plane oriented in the Z- and Y-axis. The X-calibration element is fixedly connected to a frame of the inkjet system. The substrate holder comprises at least two sensors, so called X-sensors for measuring a relative distance in X-direction in between the substrate holder and the calibration element X-reference surface. Preferably, the at least two X-sensors are arranged at a predetermined distance in Y-direction, a shift, from each other. The at least two X-sensors are positioned at a same height level in Z-direction. Advantageously, the arrangement of the substrate holder including the at least two X-sensors can be used in a holder calibration method according to the sixth aspect of the invention as described hereafter. In particular, the at least two X-sensors can be used to provide a more accurate positioning of the substrate holder in X-direction. Advantageously, after homing the substrate holder to the imaginary plane to a home position, the home position of the substrate holder can be maintained more accurately during a travel of the substrate positioning stage. Additionally, a more accurate rotational positioning about an upwards axis Rz can be obtained.

In an embodiment of the inkjet system according to the sixth aspect of the invention, the inkjet system comprises a Z-calibration element including a calibration element Z-reference surface. The calibration element reference surface extends in the printing direction, the Y-direction, in parallel with a plane oriented in the X- and Y-axis. The Z-calibration element is fixedly connected to a frame of the inkjet system. The substrate holder comprises at least two sensors, also called Z-sensors, for measuring a relative distance in Z-direction in between the substrate holder and the calibration element Z-reference surface. The at least two Z-sensors are arranged at a predetermined distance in Y-direction, a shift, from each other. The at least two Z-sensors are preferably positioned at a same lateral level in Z-direction. Advantageously, the arrangement of the substrate holder including the at least two sensors can be used in a holder calibration method according to the sixth aspect of the invention as described hereafter. In particular, the at least two Z-sensors can be used to provide a more accurate positioning of the substrate holder in Z-direction. In particular, the at least two Z-sensors can further be used to provide a more accurate rotational positioning about a lateral axis Rx.

In a further embodiment of the inkjet system according to the sixth aspect of the invention, the inkjet system comprises a Z-calibration element including a calibration element Z-reference surface. The calibration element reference surface extends in the printing direction, the Y-direction, in parallel with a plane oriented in the X- and Y-axis. The substrate holder comprises at least a third sensor, also called a Z3-sensor, for measuring a relative distance in Z-direction in between the substrate holder and the calibration element Z-reference surface. The at least third Z3-sensor is arranged at a predetermined distance in X-direction, a shift, from the at least one other Z-sensor. Advantageously, the arrangement of the substrate holder including the at least three sensors can be used in a holder calibration method according to the sixth aspect of the invention as described hereafter. In particular, the at least three Z-sensors can be used to provide a more accurate positioning of the substrate holder in Z-direction and a more accurate rotational positioning about a longitudinal axis Ry.

In an embodiment of the inkjet system according to the sixth aspect of the invention, the X-calibration element and Z-calibration element are incorporated into one XZ-calibration element. Instead of two separate calibration elements, the XZ-calibration element advantageously provides one component which has a higher functionality. The XZ-calibration element comprises a X-reference surface and a Z-reference surface. The XZ-calibration element is fixedly connected to a frame of the inkjet system.

In an embodiment of the inkjet system according to the sixth aspect of the invention, the inkjet system comprises a marking unit for marking a substrate by applying at least two fiducial members in a substrate reference surface. In particular, the substrate reference surface is a top surface of the substrate. Further, the inkjet system comprises a scanning unit for scanning a reference surface of a substrate to determine a position of a fiducial member. Preferably, the metrology frame supports the scanning unit for scanning a substrate. In particular, the scanning unit is arranged to determine a position of the at least two fiducial members in a substrate reference surface of a substrate with respect to an scanning reference axis. The scanning reference axis has a predetermined orientation in the X-Y plane, e.g. in the X-direction or Y-direction.

In an exemplary embodiment of the inkjet system according to the sixth aspect of the invention, the scanning reference axis extends in parallel with the X-axis of the inkjet system. The scanning unit outputs a scanned position of the at least two fiducial members. The scanned position includes a first coordinate in X-direction and a second coordinate in Y-direction. The control electronics of the inkjet system are configured to determine from the at least two scanned positions a deviation in an initial position of the substrate in a rotational direction about the Z-axis, Rz. The deviation can be compensated by a rotational movement of the substrate holder to bring the substrate in a print position. In the print position, the substrate is ready to be printed. Further, the control electronics are configured to store a X-calibration value and/or an Y-calibration value to establish respectively a X-position and/or Y-position of the substrate in the print position.

In an embodiment of the inkjet system according to the sixth aspect of the invention, the inkjet system comprises control electronics which comprises software which is configured to carry out a method for calibrating the substrate holder with respect to the virtual plane as described. A method for calibrating the substrate holder with respect to the virtual plane is carried out in the inkjet system.

In an embodiment of the inkjet system according to the sixth aspect of the invention, the inkjet system is a printed circuit board inkjet system, a so called PCB inkjet system. The inkjet system is designed for printing substrates which are suitable to be used as printed circuit boards. The inkjet system is designed for producing printed circuit boards.

Further, the sixth aspect of the invention relates to a method for calibrating the substrate holder with respect to the virtual plane. The method is also called a holder calibration method. The method comprises at least one step to calibrate at least one degree of freedom of the substrate holder with respect to the virtual plane.

Preferably, a substrate is held by the substrate holder during the holder calibration method. The holder calibration method may be performed for each individual substrate as a preparing step before starting a printing operation in which ink droplets are deposited onto the substrate. The top surface of the held substrate may be used as a substrate reference surface. Advantageously, this may directly result in a compensation for varying thickness of substrates which increases the accuracy of the printing process.

In an embodiment of the method a step of the holder calibration method is performed, wherein the substrate holder is aligned with the print head holder. The substrate holder is aligned to the print head holder by positioning the substrate holder, in particular the substrate reference surface of a held substrate, at least three spaced points at a constant distance in Z-direction to the virtual plane of the print head holder. This step of aligning may also be called homing of the substrate holder. The substrate holder may be homed to the virtual plane at an individual Y-position of the substrate positioning stage. After homing the substrate holder, the substrate holder can be moved by the substrate positioning stage along the long stroke in which the holder positioning device is controlled to compensate for deviations caused by the substrate positioning device to maintain the substrate holder positioned in the virtual plane. The introduced deviations by the substrate positioning stage can be calibrated and defined by calibration values which are used to control the substrate holder.

In particular, the constant distance in Z-direction to the virtual plane of the print head holder is zero. In an embodiment, the substrate holder is aligned by mechanically contacting the substrate holder to the print head holder. Preferably, the substrate holder contacts the print head holder via the held substrate on top of the substrate holder. The substrate holder may be moved in upwards direction until the substrate holder abuts to the print head holder. The substrate holder is moved in upwards direction until the print head holder blocks a further movement. The substrate holder may be contacted with the three reference marks of the print head holder. The substrate holder may be contacted with the reference surface of the print head holder to align the substrate holder with the print head holder and so to align the substrate holder with the virtual plane. After carrying out this step of the holder calibration method, the substrate holder is positioned in Z-direction and in a rotational direction about the X-axis Rx and about the Y-axis Ry. The positioning of the substrate holder is read out as a function of an Y-position and stored as a calibration value. The calibration value is determined by storing position values of the holder actuators, in particular three vertically oriented holder actuators, as a function of an Y-positioning value of the substrate positioning stage.

In an embodiment of the holder calibration method, the substrate holder may be contacted to the print head holder at a plurality of y-positions of the substrate positioning stage to calibrate the substrate holder at a range of the travel in the printing direction.

In an embodiment of the holder calibration method, another step of the holder calibration method is carried out, wherein the substrate holder is calibrated in a rotational direction about the Z-axis, Rz. In a preparing step a substrate is provided with at least two fiducial members in the substrate reference surface. In particular, the fiducial member is represented by a cross circumvented by at least one ring. A marking unit may be used to apply the at least two fiducial points to the substrate. In the holder calibration method, the substrate including the at least two fiducial members is held by the substrate holder. The inkjet system comprises a scanning unit for scanning a substrate. The scanning unit is mounted to the metrology frame. The scanning unit is arranged in an upper region of the inkjet system at a position above the substrate holder, such that the top surface of the substrate can be scanned. The scanning unit is arranged to determine a position of the at least two fiducial members with respect to a scanning reference axis. In particular, the scanning reference axis extends in parallel with the X-axis of the inkjet system. The scanning unit outputs a scanned position of the at least two fiducial members. The scanned position includes a first coordinate in X-direction and a second coordinate in Y-direction. The control electronics of the inkjet system are configured to determine from the at least two scanned positions a deviation in position of the substrate in a rotational direction about the Z-axis, Rz. The deviation can be compensated by a rotational movement of the substrate holder. Further, the control electronics may be configured to store a X-calibration value to establish an X-position of the substrate. Additionally, the control electronics may be configured to store a X-calibration value to establish an X-position of the substrate.

During a travel of the substrate positioning stage, a travel deviation in at least one direction occurs from a desired straight path of a substrate. In an embodiment of the holder calibration method according to the sixth aspect of the invention, the inkjet system may be provided with a calibration element, in particular an elongated calibration element, more in particular a calibration strip to compensate for a travel deviation in X-direction, a so called X-deviation or Z-direction, a so called Z-deviation. The calibration strip extends in the printing direction, the Y-direction. The calibration strip is fixedly connected to the frame of the inkjet system. The calibration strip reference is positioned in parallel with a plane oriented in the Z- and Y-axis for measuring a deviation in X-direction or with a plane oriented in the X- and Y-axis for measuring deviations in Z-direction.

In an embodiment of the holder calibration method according to the sixth aspect of the invention, the substrate positioning stage travels along the calibration strip. In particular, the calibration strip has at least one calibration strip reference surface which has a relative too low flatness of about 100 μm about a stroke of about 1.5 meter. This flatness is too low, because the substrate needs to be positioned in X-direction with an accuracy of at most 25 μm, in particular at most 10 μm, but preferably at most 5 μm.

In an embodiment, the substrate holder comprises at least two sensors for measuring a relative distance in X-direction in between the substrate holder and the calibration strip reference surface. Preferably, the sensors have a high accuracy of at least 1 μm, in particular at least 0.5 μm, but preferably at least 0.1 μm.

At least one sensor is necessary to measure a main deviation in X-direction which occurs when the substrate positioning stage travels along the long stroke. The measured X-deviation is compensated by a movement of the substrate holder in an opposite X-direction.

At least two sensors are necessary to compensate for the relative low flatness of the calibration strip. The at least two sensors are spaced apart from each other in Y-direction about a predetermined distance 'S'. The at least two sensors measure both a relative distance in X-direction as a function of a position along the Y-axis of the substrate positioning stage. Hence, a first sensor measures a first relative distance X1 at a certain Y-position and a second sensor measure a second relative distance X2 at the same Y-position of the substrate positioning stage. The measurement of relative distances can be performed about the whole travel distance of the substrate positioning stage to output a set of X1 values and a set of X2-values as a function of an Y-position. The distance 'S' in between the first and second sensor is known which implicates a shift in Y-direction of the measured X1 and X2 values. By comparing the two sets of measured values X1 and X2 at a first and second Y-position which correspond to the shift at a distance 'S', the flatness of the calibration strip can be determined. The comparison of the two sets of measured values X1 and X2 can be made by a subtraction of the values X1 and X2 for a corresponding Y positions. Subsequently, the flatness of the calibration strip can be taken into account during a controlled movement of the substrate positioning stage. The flatness of the calibration strip and the main X-deviation can be compensated in a feed forward control by the control electronics.

In an analoguous embodiment, the substrate holder comprises at least two sensors for measuring a relative distance in Z-direction in between the substrate holder and the calibration strip reference surface. Preferably, the sensors have a high accuracy of at least 1 μm, in particular at least 0.5 but preferably at least 0.1 μm.

At least one sensor is necessary to measure a main deviation in Z-direction which occurs when the substrate positioning stage travels along the long stroke. The measured Z-deviation is compensated by a movement of the substrate holder in an opposite Z-direction.

At least two sensors are necessary to compensate for the relative low flatness of the calibration strip. The at least two sensors are spaced apart from each other in Y-direction about a predetermined distance 'S'. The at least two sensors measure both a relative distance in X-direction as a function of a position along the Y-axis of the substrate positioning stage. Hence, a first sensor measures a first relative distance Z1 at a certain Y-position and a second sensor measure a second relative distance Z2 at the same Y-position of the substrate positioning stage. The measurement of relative distances can be performed about the whole travel distance of the substrate positioning stage to output a set of Z1 values and a set of Z2-values as a function of an Y-position. The distance 'S' in between the first and second sensor is known which implicates a shift in Y-direction of the measured Z1 and Z2 values. By comparing the two sets of measured values Z1 and Z2 at a first and second Y-position which correspond to the shift at a distance 'S', the flatness of the calibration strip can be determined. The comparison of the two sets of measured values Z1 and Z2 can be made by a subtraction of the values Z1 and Z2 for a corresponding Y positions. Subsequently, the flatness of the calibration strip can be taken into account during a controlled movement of the substrate positioning stage. The flatness of the calibration strip and the main Z-deviation can be compensated in a feed forward control by the control electronics.

Further, the invention relates to a method of controlling a position of a substrate holder after carrying out a step of the holder calibration method.

Embodiments of the sixth aspect according to the sixth aspect of the invention may be defined by the following clauses with prefix 975:

975_1. Inkjet system IS for printing an ink pattern on a substrate S comprising
- a substrate holder for holding a substrate;
- a substrate positioning stage PS for positioning the substrate holder in a printing direction, wherein the substrate holder is supported by the substrate positioning stage, wherein the substrate positioning stage PS is movable by a stage positioning device;
- a print head holder for holding a print head assembly which includes at least one print head for ejecting ink from a nozzle to the substrate;
- , wherein the inkjet system further comprises a holder positioning device HD for positioning the substrate holder in at least one degree of freedom with respect to the substrate positioning stage.

975_2. Inkjet system according to clause 975_1, wherein the at least one degree of freedom is directed in the printing direction.

975_3. Inkjet system according to clause 975_1, wherein the holder positioning device HD positions the substrate holder SH in at least three degrees of freedom, wherein the substrate holder SH is positioned in upwards direction (Z-direction), in a rotational direction Ry along a longitudinal axis (Y-axis) and a rotational direction Rx along a lateral axis (X-axis).

975_4. Inkjet system according to clause 975_1, wherein the holder positioning device HD positions the substrate holder in all degrees of freedom (X,Y,Z, Rx, Ry, Rz) with respect to the substrate positioning stage.

975_5. Inkjet system according to any of the preceding 975_clauses, wherein the holder positioning device comprises at least one holder actuator in which the at least one holder actuator positions one degree of freedom in translation (X,Y,Z) and wherein two paired holder actuators limit together a rotational degree of freedom in movement (Rx, Ry,Rz).

975_6. Inkjet system according to any of the preceding 975_clauses, wherein the print head holder H is stationary mounted in the inkjet system.

975_7. Inkjet system according to any of the preceding 975_clauses, wherein the print head holder comprises at least three reference marks Z1,Z2, Z3 which define a virtual plane, wherein the virtual plane is in parallel with a imaginary plane formed by a common positioning, in particular a common height level in a Z-direction, of a group of nozzles of the print head, such that a substrate holder can be positioned at a constant distance, in particular a distance zero, to the reference marks of the print head holder to align the substrate holder with the print head holder and so to align the substrate holder with the virtual plane.

975_8. Inkjet system according to clause 975_7, wherein the holder positioning device is programmed to control the substrate holder in parallel with the virtual plane.

975_9. Inkjet system according to any of the preceding 975_clauses, wherein the inkjet system IS comprises a force frame (FF) which supports a metrology frame (MF), wherein a vibration isolation system (VIS) is provided in between the force frame (FF) and the metrology frame MF to support the metrology frame (MF) from the force frame (FF) while isolating the metrology frame MF from vibrations in the force frame (FF), wherein the metrology frame MF supports the substrate positioning stage PS and the print head holder.

975_10. Inkjet system according to clause 975_9, wherein the stage positioning device comprises a stage guidance, a stage positioning measuring system and a stage actuator, wherein the stage guidance and stage positioning device are supported by the metrology frame and wherein the stage actuator is supported by the force frame.

975_11. Inkjet system according to any of the clauses 975_6-975_10, wherein the inkjet system comprises at least one Z-sensor (z) which is stationary mounted to the metrology frame (MF) for measuring a Z-distance to a relevant top surface for maintaining a constant distance in between the virtual plane and a top surface of a substrate and control electronics (CE) which are configured to receive a signal from the at least one Z-sensor (z) during a printing process, which control electronics are programmed to control in a step during the printing process the holder positioning device HD to compensate for a detected deviation by the at least one Z-sensor.

975_12. Inkjet system according to any of the preceding 975_clauses, wherein the inkjet system comprises a calibration element including a calibration element reference surface which extends in the longitudinal axis, the Y-direction, in parallel with a plane oriented in the Z- and Y-axis, wherein the substrate holder comprises at least two sensors for measuring a relative distance in X-direction in between the substrate holder and the calibration element reference surface.

975_13. Inkjet system according to any of the preceding 975_clauses, wherein the inkjet system comprises a marking unit for marking a substrate by applying at least two fiducial members in a substrate reference surface.

975_14. Inkjet system according to any of the preceding 975_clauses, wherein the inkjet system further comprises a scanning unit for scanning a substrate, in particular for scanning a substrate reference surface to detect the at least two fiducial members.

975_15. Inkjet system according to clause 975_14, wherein the scanning unit is arranged to determine a position of the at least two fiducial members in a substrate reference surface of a substrate with respect to an scanning reference axis.

975_16. Inkjet system according to any of the preceding 975_clauses, wherein the inkjet system comprises control electronics which comprises software which is configured to carry out a method for calibrating the substrate holder with respect to the virtual plane as defined in any of the clauses 17-23.

975_17. Method for calibrating a substrate holder with respect to a virtual plane in an inkjet system which virtual plane is in parallel with an imaginary plane formed by a positioning of a group of nozzles of a printhead which are positioned in a common plane, comprising a step of providing the inkjet system comprising:
- a substrate holder for holding a substrate;
- a substrate positioning stage PS for positioning the substrate holder in a printing direction, wherein the substrate holder is supported by the substrate positioning stage, wherein the substrate positioning stage PS is movable by a stage positioning device;

a print head holder for holding a print head assembly which includes at least one print head for ejecting ink from a nozzle to the substrate;
, wherein the inkjet system further comprises a holder positioning device HD for positioning the substrate holder in at least one degree of freedom with respect to the substrate positioning stage;
, wherein the method comprises at least one of the following steps for calibrating at least one degree of freedom (DOF) of the substrate holder with respect to the substrate positioning stage:
  aligning the substrate holder with the print head holder by positioning the substrate holder at a constant distance with respect to at least three reference marks Z1, Z2, Z3 of the print head holder which define a virtual plane, wherein the virtual plane is in parallel with an imaginary plane formed by a common positioning, in particular a common height level in a Z-direction, of a group of nozzles of the print head;
  aligning the substrate holder by using a X-calibration element, which includes a calibration element X-reference surface which extends in the printing direction, the Y-direction, in parallel with a plane oriented in the Z- and Y-axis, wherein the substrate holder comprises at least two X-sensors for measuring a relative distance in X-direction in between the substrate holder and the calibration element X-reference surface, wherein the at least two X-sensors are spaced apart from each other in Y-direction about a predetermined shift 'S', performing a measurement by measuring a relative distance in X-direction as a function of a position along the Y-axis of the substrate positioning stage about at least a part of a travel distance of the substrate positioning stage to output a set of X1 values and a set of X2-values as a function of an Y-position, performing a calculation wherein the predetermined shift 'S' in between the first and second sensor is used to compare the two sets of measured values X1 and X2 at respectively a first and second Y-position which correspond to the shift 'S' to determine a flatness of the calibration element to be compensated during a controlled movement of the substrate positioning stage;
  aligning the substrate holder by using a calibration element, which includes a calibration element Z-reference surface which extends in the printing direction, the Y-direction, in parallel with a plane oriented in the X- and Y-axis, wherein the substrate holder comprises at least two Z-sensors for measuring a relative distance in Z-direction in between the substrate holder and the calibration element Z-reference surface, wherein the at least two Z-sensors are spaced apart from each other in Y-direction about a predetermined shift 'S', performing a measurement by measuring a relative distance in Z-direction as a function of a position along the Y-axis of the substrate positioning stage about at least a part of a travel distance of the substrate positioning stage to output a set of Z1 values and a set of Z2-values as a function of an Y-position, performing a calculation wherein the predetermined shift 'S' in between the first and second Z-sensor is used to compare the two sets of measured values Z1 and Z2 at respectively a first and second Y-position which correspond to the shift 'S' to determine a flatness of the calibration element to be compensated during a controlled movement of the substrate positioning stage;
  aligning the substrate holder by using a scanning unit for scanning a substrate, wherein the scanning unit is arranged to determine a rotational deviation, in particular about the Z-axis, of at least two fiducial members in a substrate reference surface of a substrate held by the substrate holder with respect to a scanning reference axis which rotational deviation is to be compensated by a rotational movement of the substrate holder during a controlled movement of the substrate positioning stage.

975_18. Method according to clause 975_17, wherein a substrate is held by the substrate holder during the holder calibration method.

975_19. Method according to clause 975_17 or 975_18, wherein the substrate holder is aligned by mechanically contacting the substrate holder to the print head holder.

975_20. Method according to any of the clauses 975_17-975_19, wherein the substrate holder is aligned with the virtual plane at a plurality of y-positions of the substrate positioning stage to calibrate the substrate holder at a range of the travel in the printing direction.

975_21. Method according to any of the clauses 975_17-975_20, wherein the calibration method comprises a preparing step in providing a substrate with at least two fiducial members in a substrate reference surface.

975_22. Method according to any of the clauses 975_17-975_21, wherein the method further comprises a step of controlling a motion of the inkjet system by control electronics, wherein the control electronics are programmed to compensate for deviations which are measured during the step of calibration.

975_23. Method according to any of the clauses 975_17-975_22, wherein an inkjet system is provided which comprises a Z-calibration element including a calibration element Z-reference surface, which calibration element Z-reference surface extends in the printing direction, the Y-direction, in parallel with a plane oriented in the X- and Y-axis, wherein the substrate holder comprises at least a third sensor, a Z3-sensor, for measuring a relative distance in Z-direction in between the substrate holder and the calibration element Z-reference surface, wherein the at least third Z3-sensor is arranged at a predetermined distance in X-direction, a shift, from the at least one other Z-sensor, wherein the method comprises a step of measuring a relative distance in Z-direction by using the at least two Z-sensors including the Z3-sensor and determining a rotational deviation Ry of the substrate holder about the longitudinal axis of the inkjet system, Y-axis, with respect to the calibration element Z-reference surface and subsequently compensating the position of the substrate holder.

Now a seventh aspect of the invention will be addressed.

A seventh aspect of the invention relates to a substrate conveyor for an inkjet system and a method for transferring a substrate to the substrate conveyor. In particular, the invention relates to the field of printing substrates with high accuracy like a printing of an integrated circuit. The invention relates to the field of printing printed circuit boards by using an inkjet system. The substrate conveyor is suitable for use in an inkjet system.

A known inkjet system for printing substrates comprises several substrate conveyors for carrying and transporting substrates. A substrate is supported by a substrate conveyor during a printing operation and is transported through the inkjet system. At some places, the substrate has to be transferred from one substrate conveyor to another substrate conveyor. Usually a robot arm is used to transfer the substrates. The robot arm comprises a suction gripper which includes a plurality of suction nozzles to engage the substrate at a flat top surface. The robot arm lifts the substrate from a first substrate conveyor to transfer the substrate to a second substrate conveyor.

A first drawback to the robot arm is that the handling of the substrate leaves residues of silicon rubber or other contaminations on top of the substrate surface. These contaminations disturb the printing process.

Another drawback of the robot arm is that the accuracy of the transfer is not satisfying. The positioning of the substrate on top of the second substrate conveyor is inaccurate which leads to fall out and failures during the printing process.

The general object of the present seventh aspect of the invention is to at least partially eliminate the above mentioned drawbacks and/or to provide a useable alternative. More specific, it is an object of the seventh aspect of the invention to provide a transfer unit which allows an efficient and accurate transfer of a supported substrate from a first substrate conveyor to a second substrate conveyor.

According to the seventh aspect of the invention, this object is achieved by a substrate conveyor as defined in clause 976_1.

According to the seventh aspect of the invention a substrate conveyor is provided for supporting and transporting a substrate in an inkjet system. A substrate is moved together with the substrate conveyor through the inkjet system in a conveyor direction. The substrate conveyor comprises a conveyor body including a conveyor support face for supporting the substrate. The substrate conveyor comprises a conveyor guidance for guiding the conveyor body.

The substrate conveyor comprises further a substrate transfer unit for transferring the substrate to and fro the conveyor support face. The substrate transfer unit comprises at least one gripper for gripping the substrate. The substrate transfer unit further comprises a gripper holder for holding the at least one gripper and a transfer guidance for guiding the gripper holder. Further, the transfer unit comprises a first holder actuator for driving the gripper holder along the transfer guidance in a transfer direction along the substrate conveyor.

The substrate conveyor according to the seventh aspect of the invention is improved in that the substrate transfer guidance is fixed to the conveyor body, such that during a movement of the substrate conveyor body, the substrate transfer guidance moves together with the conveyor body.

Advantageously, a transferring and a subsequent positioning of a substrate onto the conveyor support face can be performed with high precision. Due to the fixation of the transfer guidance to the conveyor body, the substrate can be positioned more accurate on the conveyor support face. Instead of a mounting of the transfer guidance to a frame of an inkjet system, the transfer unit according to the seventh aspect of the invention is mounted directly to the conveyor body. The transfer unit has a transfer unit reference which is located at the conveyor body which makes a high accuracy in positioning of the transfer unit possible. Deficiencies as a result of positioning tolerances build up during an assembly of the inkjet system which would cause inaccuracies during a printing process can be reduced. Additionally, a more precise transferring of substrates reduce failures during operation and improves the reliability of the inkjet system.

In an embodiment of the substrate conveyor according to the seventh aspect of the invention, the at least one gripper is movable along a gripper path. The gripper path extends over the conveyor support face in a conveyor direction from a first position to a second position. The at least one gripper is movable from the first position to the second position with respect to the conveyor body. The first position is located in a front region of the substrate conveyor body and the second position is located in a back region of the substrate conveyor body. In an operation of the inkjet system, seen in the conveyor direction, the at least one gripper grips a rectangular substrate at its front or back located edge instead of its lateral edges. Herewith, the least one gripper pulls or pushes the substrate to the conveyor support face during a transfer operation. Advantageously, especially when conveying relatively thin substrates, a one sided pulling or pushing transfer operation reduces a risk on damages due to bending to the substrate during a transfer operation. A double sided lateral engagement can damage the thin substrate. Preferably, the at least one gripper pulls the substrate to the conveyor support face to prevent a buckling of the substrate during a transfer operation. To obtain a pulling transfer operation, the at least one gripper of the transfer unit grips the substrate at a front or back edge.

In an embodiment of the substrate conveyor according to the seventh aspect of the invention, the gripper path of the at least one gripper is linear and extending across the substrates conveyor in the conveyor direction.

In an embodiment of the substrate conveyor according to the seventh aspect of the invention, the gripper path of the at least one gripper comprises downwardly extending ends. The gripper path includes an downward extending gripper path section for sinking down the gripper with respect to the substrate conveyor support face. When the gripper moves along the gripper path, the gripper moves down at the end of the gripper path. Herewith, the gripper sinks down with respect to the conveyor support face. The gripper sinks down under a height level of the conveyor support face, such that a substrate can pass above the gripper by a sliding movement.

In an embodiment of the substrate conveyor according to the seventh aspect of the invention, the at least one gripper comprises a clamp element for clamping a substrate at an edge region. The clamp element includes a first and second clamping member, which are movable connected to each other for clamping an edge of substrate in between the first and second clamping member. Advantageously, the clamping element engages on a relatively small area at an edge of the substrate which reduces a risk on contaminations of the upper surface of the substrate. In a printing operation, even minute residues of silicon or rubbers can drastically affect ink flow behavior. Additionally, the engagement with the clamping element provides a reliable engagement and reduces a risk on damages to the substrate which can further disturb a printing operation.

In an embodiment of substrate conveyor according to invention, the gripper holder holds at least a pair of a first gripper and a second gripper, wherein the paired first and second gripper are oriented in opposite directions. Advantageously, the paired grippers allow a selection of a pushed or pulled transfer of a substrate to another conveyor body.

In an alternative embodiment of the substrate conveyor according to the seventh aspect of the invention, the at least one gripper comprises a suction head for engaging a substrate to the gripper by a sucking force.

In an alternative embodiment of the substrate conveyor according to the seventh aspect of the invention, the at least one gripper comprises a electrostatic, magnetic or capacitive head for engaging a substrate to the gripper by respectively an electrostatic, magnetic or capacitive force.

In an embodiment of the substrate conveyor according to the seventh aspect of the invention, the gripper holder is elongated. The gripper holder may be beam shaped. The gripper holder extends in a transversal direction with respect to the conveyor direction across a full width of the conveyor body. The transfer guidance includes two transfer rails which are each mounted at a lateral side of the conveyor body. The gripper holder is at both ends linearly movable, e.g. by ball bearings, connected to the transfer rails. Advantageously, herewith a rigid support is provided to obtain an accurate linear movement of the at least one gripper across the conveyor support face.

In an embodiment of the substrate conveyor according to the seventh aspect of the invention, the transfer unit comprises a second holder actuator for acting the gripper holder in an up-down direction. In particular, the gripper holder is movable in substantially vertical direction. Preferably, the second holder actuator is a voice coil actuator. The transfer unit may further comprise a gripper holder guidance for guiding the gripper holder in the up-down direction. Preferably, the gripper holder guidance is a resilient guidance, e.g. a spring leaf guidance including one or two parallel arranged spring leafs. Herewith, the gripper holder which positions the at least one gripper can be moved up and down with respect to the conveyor support face to sink the gripper holder under the height level of the conveyor support face, such that a substrate can pass over the gripper holder.

In an embodiment of the substrate conveyor according to the seventh aspect of the invention, the conveyor support face of the conveyor body comprises a plurality of gas openings for keeping a substrate in abutting engagement with the conveyor support face by sucking or for releasing a substrate from the conveyor support face. Preferably, during a conveyance of the substrate, the substrate is engaged to the conveyor support face by a sucking force, which is generated by sucking a gas, in particular air, through the gas openings. In such a manner it is possible to keep, in particular light weighted substrates in position on top of the conveyor body. When the substrate has to be transferred from the conveyor support face, the sucking force can be cancelled and instead of sucking now a blowing force can be generated by blowing a gas, in particular air, through the gas openings of the conveyor body. The substrate is raised by the blowing force away from the conveyor support face. Subsequently, the transfer unit engages to the substrate to transfer the substrate away from the conveyor body. Advantageously, the gas overpressure allows a contactless substrate transport through an inkjet system.

In an embodiment of the substrate conveyor according to the seventh aspect of the invention, the conveyor support face of the conveyor body is subdivided in a plurality of engagement zones. An amount of engagement zones can be operated in dependence of outer dimensions of a particular substrate. Advantageously, the engagement zones in the conveyor body allow a handling of substrates in a variety of sizes.

In an embodiment of the substrate conveyor according to the seventh aspect of the invention the substrate conveyor is arranged as a printing conveyor of an inkjet system for conveying a substrate during a printing operation relative to a printing head. The printing conveyor comprises a conveyor body which supports a substrate and moves together with the substrate during a printing operation.

In a particular embodiment of the printing conveyor according to the seventh aspect of the invention, the conveyor body of the printing conveyor comprises a substrate positioning stage for moving a supported substrate in a printing direction with respect to the print head holder during the printing operation. Further, the conveyor body of the printing conveyor comprises a stage positioning device for positioning the substrate positioning stage with respect to a frame of the inkjet system. Further, the conveyor body of the printing conveyor comprises a substrate holder connected to the substrate positioning stage for holding a substrate.

In an embodiment of the printing conveyor according to the seventh aspect of the invention, the substrate transfer unit is connected to the substrate holder. The substrate holder may be movable connected in at least one degree of freedom with respect to the substrate positioning stage. A holder positioning device may be provided for positioning the substrate holder with respect to the substrate positioning stage in the at least one degree of freedom. In particular, the transfer guidance is fixedly connected to the substrate holder.

In an alternative embodiment of the printing conveyor according to the seventh aspect of the invention, the substrate transfer unit is connected to substrate positioning stage. The transfer guidance of the subject transfer unit is fixedly connected to the substrate positioning stage. The substrate holder is movable in at least one degree of freedom with respect to the transfer guidance.

In an embodiment of the substrate conveyor according to invention, the substrate conveyor is arranged as a station conveyor for handling a substrate. The inkjet system may comprise a station for handling the substrate. The station is for example a supply station for supplying substrates to a print area of the inkjet system. The station may be a buffer station for temporarily storing a substrate in the inkjet system. The station may be a discharge station for discharging substrates after being processed in the printing area of the inkjet system.

Further, the invention relates to an inkjet system for printing an ink pattern on a substrate. The inkjet system comprises a substrate conveyor in an embodiment as described above. The inkjet system further comprises a frame for holding components of the inkjet system and a printhead holder for holding at least one printhead, which printhead holder is connected to frame. The substrate conveyor has a conveyor body which is movable relative to the frame. The substrate transfer unit is connected to the substrate conveyor, such that during the movement of the substrate conveyor body, the substrate transfer unit moves together with the conveyor body.

In an embodiment of the inkjet system according to the seventh aspect of the invention, the inkjet system comprises a substrate conveyor according to the seventh aspect of the invention as a printing conveyor for transporting a substrate in a printing area during a printing operation.

In an embodiment of the inkjet system according to the seventh aspect of the invention, the inkjet system comprises a handling station for handling a substrate, wherein the handling station comprises a substrate conveyor as a station conveyor for conveying a substrate, wherein the station conveyor comprises a transfer unit which is arranged to transfer a substrate from the station conveyor to the printing conveyor.

In an embodiment of the inkjet system according to the seventh aspect of the invention, the handling station is a supply station for supplying a substrate to the printing conveyor, a buffer station for temporary storing a substrate or a discharge station for discharging a substrate away from the printing conveyor.

Further, the seventh aspect of the invention relates to a method of transferring a substrate from a first substrate conveyor to a second substrate conveyor of an inkjet system. The method comprises a step of providing a first and second substrate conveyor and at least one transfer unit. The at least one transfer unit is connected to at least the first or second substrate conveyor. Only one or both substrate conveyors can be provided with a transfer unit. The transfer unit is mounted to the first or/and second substrate conveyor. The transfer unit comprises a gripper holder including at least one gripper which is movable along a gripper path from a first position at a front region of the substrate conveyor to a second position at a back region of the substrate conveyor.

The method according to the seventh aspect of the invention comprises a step of providing a substrate on a conveyor support face of the first conveyor. Further, the method according to invention comprises a step of positioning the second substrate conveyor adjacent the first substrate conveyor. In dependence of a situation, the first substrate conveyor can be positioned in front of the second substrate conveyor or vice versa. In dependence of the situation, a substrate can be transferred in a forward or backward transfer direction. The substrate can be pulled or pushed onto the second substrate conveyor. The first and second substrate conveyor in the adjacent position are aligned with respect to their conveyor support face.

The method according to the seventh aspect of the invention comprises a step of positioning the gripper holder to the respectively the first position or second position, such that the at least one gripper is able to grip the substrate at the first conveyor at an edge region. The at least one gripper grips the substrate in a small area at the front or back edge of the substrate. Subsequently, the substrate at the first substrate conveyor is gripped at an edge region. The gripper holder is moved to the respectively second or first position while gripping the substrate and moving the substrate from the first substrate conveyor to the second substrate conveyor. After positioning the substrate onto the second substrate conveyor, the substrate is released from the transfer unit.

In an embodiment of the method according to the seventh aspect of the invention, the substrate is transferred in a floating condition from the first substrate conveyor to the second substrate conveyor. The floating condition is provided by generating an gas film underneath a supported substrate. The floating condition is obtained by supplying gas to the substrate conveyor support face underneath the supported substrate. Advantageously, the substrate is transferred without contact with the substrate conveyor which reduces a risk on damages to the substrate and reduces a necessary transfer energy.

In an embodiment of the method according to the seventh aspect of the invention a calibration is performed in a preparing step for positioning the second substrate conveyor adjacent the first substrate conveyor. The calibration is performed by docking the first and second substrate conveyor to each other. The first substrate conveyor is mechanically docked to the second substrate conveyor. A pin and socket structure may be provided for mechanically docking the first and second substrate conveyor. A docking position of the first and second substrate conveyor may be stored by a control electronics of the inkjet system, wherein during a printing process the first and second substrate conveyor may return to the stored docking position for transferring a substrate. Advantageously, the stored docking position may increase an accuracy during the printing process which may reduce a risk of transfer-failure or damages to the substrate during a transfer.

In an embodiment of the method according to the seventh aspect of the invention, the first or second substrate conveyor is a printing conveyor, wherein the at least one gripper is sunken with respect to a conveyor support face of the printing conveyor after transferring a substrate onto a printing conveyor. Advantageously, a printing process may be performed without an interference with the transfer unit.

Embodiments of the seventh aspect according to the invention may be defined by the following clauses with prefix 976:

976_1 Substrate conveyor for supporting a substrate during a movement in an inkjet system, wherein the substrate conveyor comprises a conveyor body including a conveyor support face for supporting the substrate, and a conveyor guidance for guiding the conveyor body in a conveyor direction, wherein the substrate conveyor comprises further a substrate transfer unit for transferring the substrate to and fro the conveyor support face, wherein the substrate transfer unit comprises at least one gripper for gripping the substrate;

a gripper holder for holding the at least one gripper;

a transfer guidance for guiding the gripper holder;

a first holder actuator for driving the gripper holder along the transfer guidance in a transfer direction along the substrate conveyor;

wherein the substrate transfer guidance is fixed to the conveyor body, such that during a movement of the substrate conveyor body, the substrate transfer guidance moves together with the conveyor body.

976_2. Substrate conveyor according to clause 976_1, wherein the at least one gripper is movable over the conveyor support face along a gripper path from a first to a second position, wherein the first position is located in a front region of the substrate conveyor body and wherein the second position is located in a back region of the substrate conveyor body.

976_3. Substrate conveyor according to clause 976_1 or 976_2, wherein the gripper path includes an downward extending gripper path section for sinking down the at least one gripper with respect to the substrate conveyor support face.

976_4. Substrate conveyor according to any of the clauses 976_1-976_3, wherein the at least one gripper comprises a clamp element for clamping a substrate at an edge region.

976_5. Substrate conveyor according to any of the clauses 976_1-976_4, wherein the gripper holder holds at least a pair of a first gripper and a second gripper, wherein the paired first and second gripper are oriented in opposite directions.

976_6. Substrate conveyor according to any of the clauses 976_1-976_5, wherein the conveyor support face comprises a plurality of gas openings for keeping a substrate in abutting engagement with the conveyor support face by sucking.

976_7. Substrate conveyor according to any of the preceding 976_clauses, wherein the substrate conveyor is a printing conveyor for conveying a substrate during a printing operation, wherein the printing conveyor comprises a substrate positioning stage for moving a substrate in a printing direction with respect to the print head holder during the printing operation;

a stage positioning device for positioning the substrate positioning stage with respect to the frame; and a substrate holder connected to the substrate positioning stage for holding a substrate;

wherein the substrate holder is movable connected in at least one degree of freedom with respect to the substrate positioning stage, wherein a holder positioning device is provided for positioning the substrate holder with respect to the substrate positioning stage in the at least one degree of freedom, wherein the transfer guidance of the substrate transfer unit is fixed to the substrate holder.

976_8. Substrate conveyor according to any of the clauses 976_1-976_6, wherein the substrate conveyor is a station conveyor of a handling station for handling a substrate in the handling station.

976_9. Inkjet system for printing an ink pattern on a substrate comprising a substrate conveyor according to any of the preceding clauses, and further comprising:
 a frame for holding components of the inkjet system;
 a print head holder for holding at least one print head, which printhead holder is connected to the frame;
 wherein the substrate conveyor has a conveyor body which is movable relative to the frame, wherein the substrate transfer unit is connected to the conveyor body, such that during a movement of the conveyor body, the substrate transfer unit moves together with the conveyor body.

976_10. Inkjet system according to clause 976_9 comprising a substrate conveyor as a printing conveyor for transporting a substrate in a printing area during a printing operation.

976_11. Inkjet system according to clause 976_9 or 976_10, wherein the inkjet system comprises a handling station for handling a substrate, wherein the handling station comprises a substrate conveyor as a station conveyor for conveying a substrate, wherein the station conveyor comprises a transfer unit which is arranged to transfer a substrate from the station conveyor to the printing conveyor.

976_12. Inkjet system according to clause 976_11, wherein the handling station is a supply station for supplying a substrate to the printing conveyor, a buffer station for temporary storing a substrate or a discharge station for discharging a substrate away from the printing conveyor.

976_13. Method of transferring a substrate from a first substrate conveyor to a second substrate conveyor of an inkjet system comprising the steps of:
 providing a first and second substrate conveyor, wherein at least one of the first and second substrate conveyor comprises a transfer unit, wherein the transfer unit is mounted to the substrate conveyor, wherein the transfer unit comprises a gripper holder including at least one gripper which is movable along a gripper path from a first position at a front region of the substrate conveyor to a second position at a back region of the substrate conveyor;
 providing a substrate on a conveyor support face of the first conveyor;
 positioning the second substrate conveyor adjacent the first substrate conveyor;
 positioning the gripper holder to the respectively first position or second position, such that the at least one gripper is able to grip the substrate at the first conveyor at an edge region;
 gripping the substrate at the first substrate conveyor at the edge region;
 moving the gripper holder to the respectively second or first position while gripping the substrate and moving the substrate from the first substrate conveyor to the second substrate conveyor;
 releasing the substrate when the substrate is positioned at the second substrate conveyor.

976_14. Method according to clause 976_13, wherein the substrate is transferred in a floating condition from the first substrate conveyor to the second substrate conveyor, which floating condition is obtained by supplying gas to the substrate conveyor support face underneath a supported substrate.

976_15. Method according to clause 976_13 or 976_14, wherein the substrate is kept in position at the second substrate conveyor by a sucking force at the substrate conveyor support face.

976_16. Method according to any of the clauses 976_13-976_15, wherein a calibration for positioning the second substrate conveyor adjacent the first substrate conveyor is performed by mechanically docking the first and second substrate conveyor to each other, wherein the calibration comprises a step of storing a docking position in which the first substrate conveyor is docked to the second substrates conveyor by control electronics.

976_17. Method according to any of the clauses 976_13-976_16, wherein the first or second substrate conveyor is a printing conveyor, wherein the at least one gripper is sunken with respect to a conveyor support face of the printing conveyor after transferring a substrate onto the printing conveyor.

Thus, this patent application presents several measures, features and aspects of the invention which may be considered as stand-alone inventions or aspects, but which inventions or aspects may also be combined in one embodiment as complementary to each other and/or to reinforce obtainable effects. Here it is explicitly stated, that the described first till seven aspects of the invention are considered patentable as such and may be subject to a divisional patent application. In particular, the provided clauses which are dedicated to the respective aspects are considered to define patentable subject matter relating to the respective aspects of the invention. The provided clauses can be considered as claims for a possible divisional application for each individual aspect of the invention.

The several aspects of the invention will be explained in more detail with reference to the appended drawings. The drawings show a practical embodiment according to any of the aspects of the invention, which may not be interpreted as limiting the scope of the invention. Explained measures with reference to one aspect of the invention can be readily combined with measures explained with reference to another aspect of the invention. Specific features may also be considered apart from the shown embodiment and may be taken into account in a broader context as a delimiting feature, not only for the shown embodiment or aspect but as a common feature for all embodiments of any aspect falling within the scope of the appended claims and/or presented clauses, in which:

in particular with respect to the first aspect,

Figure 3:
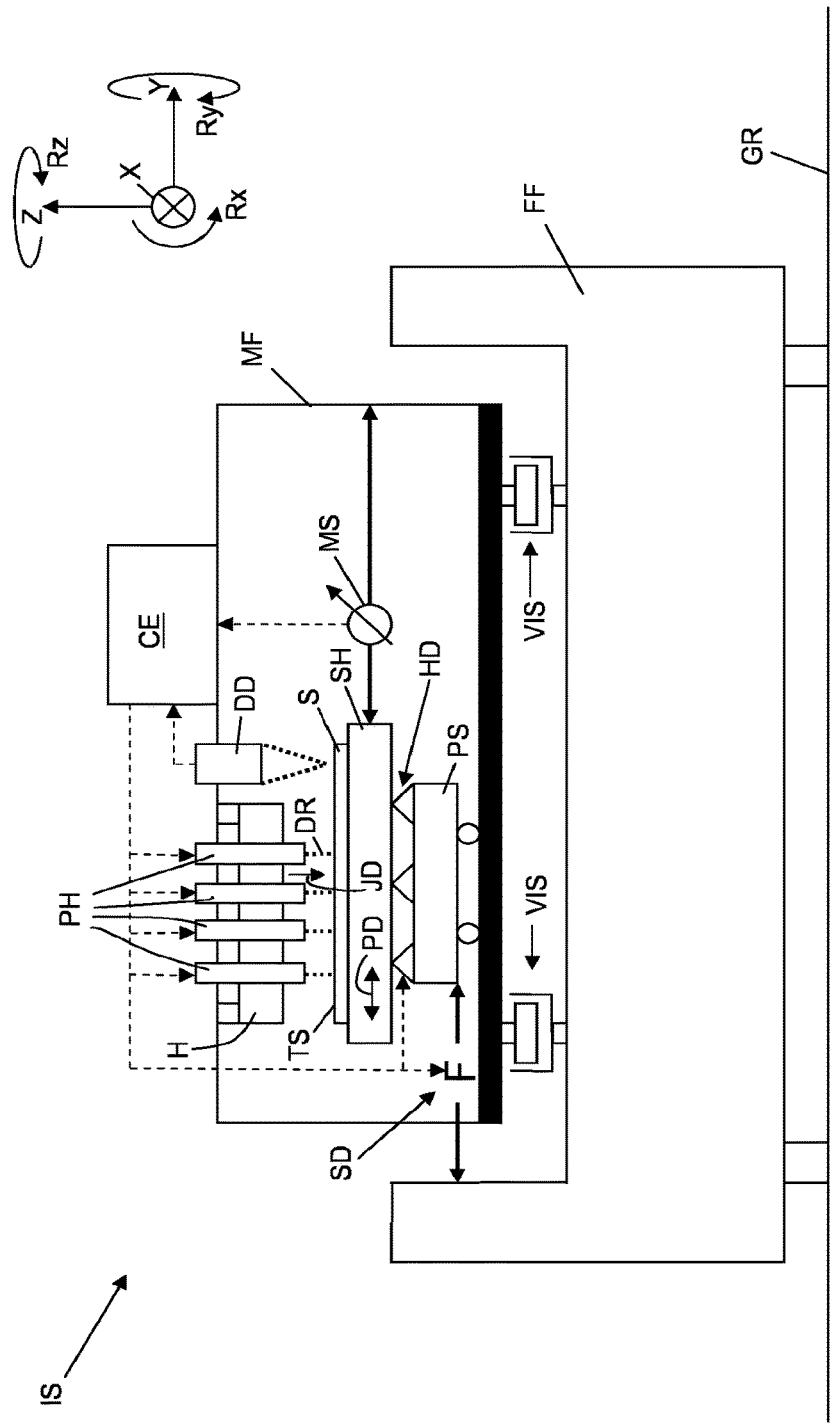
Figure 4:
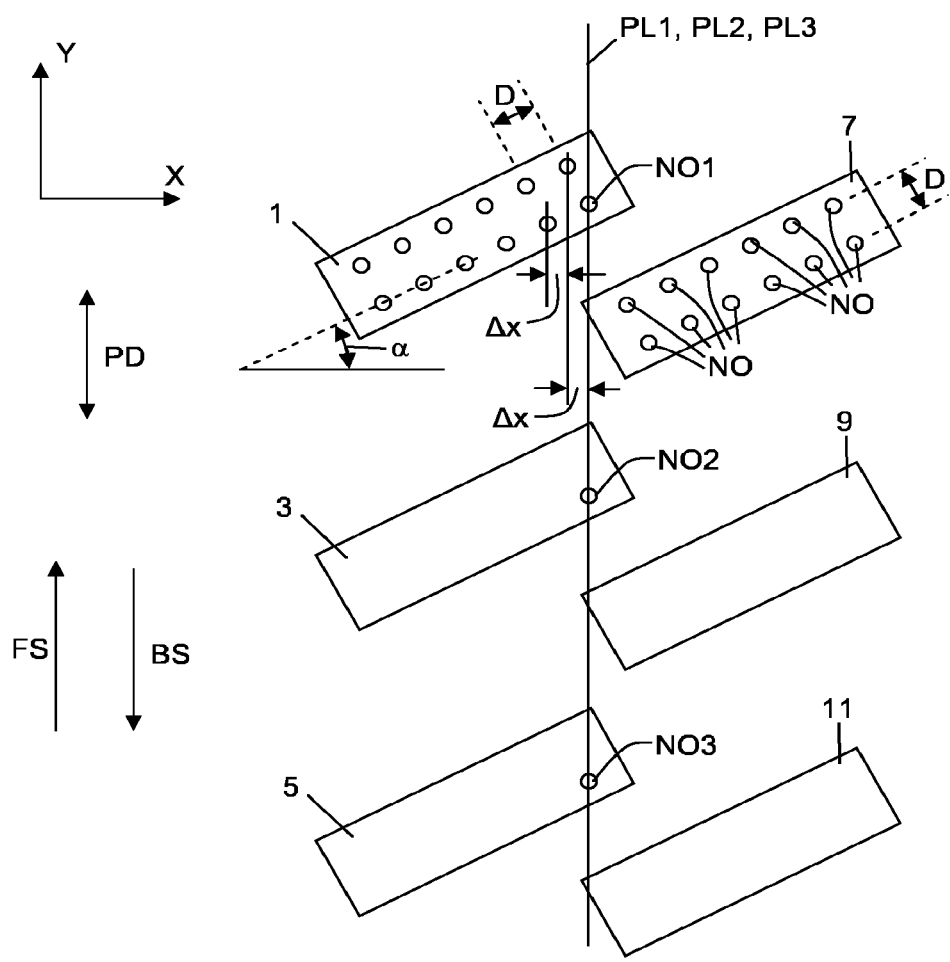
Figure 5:
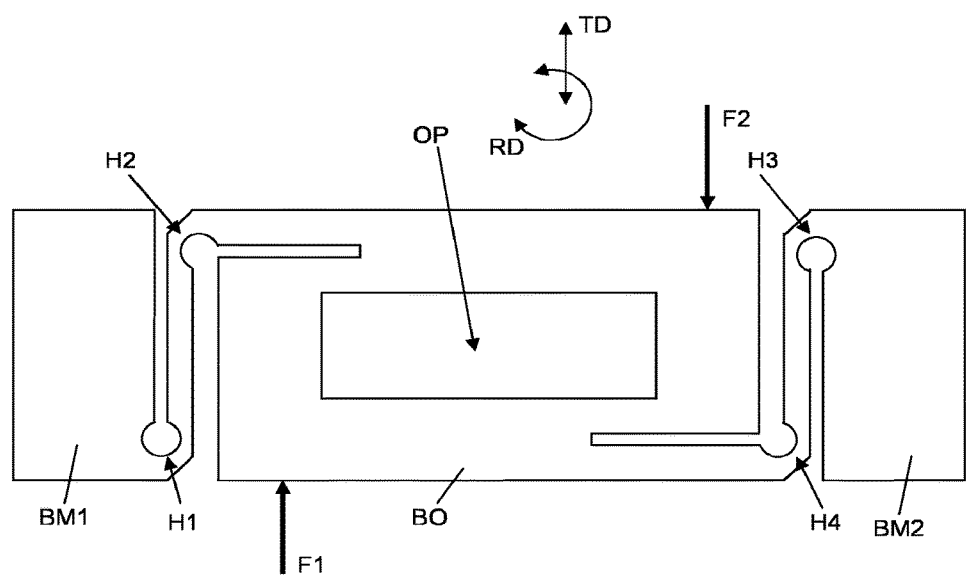
Figure 6:
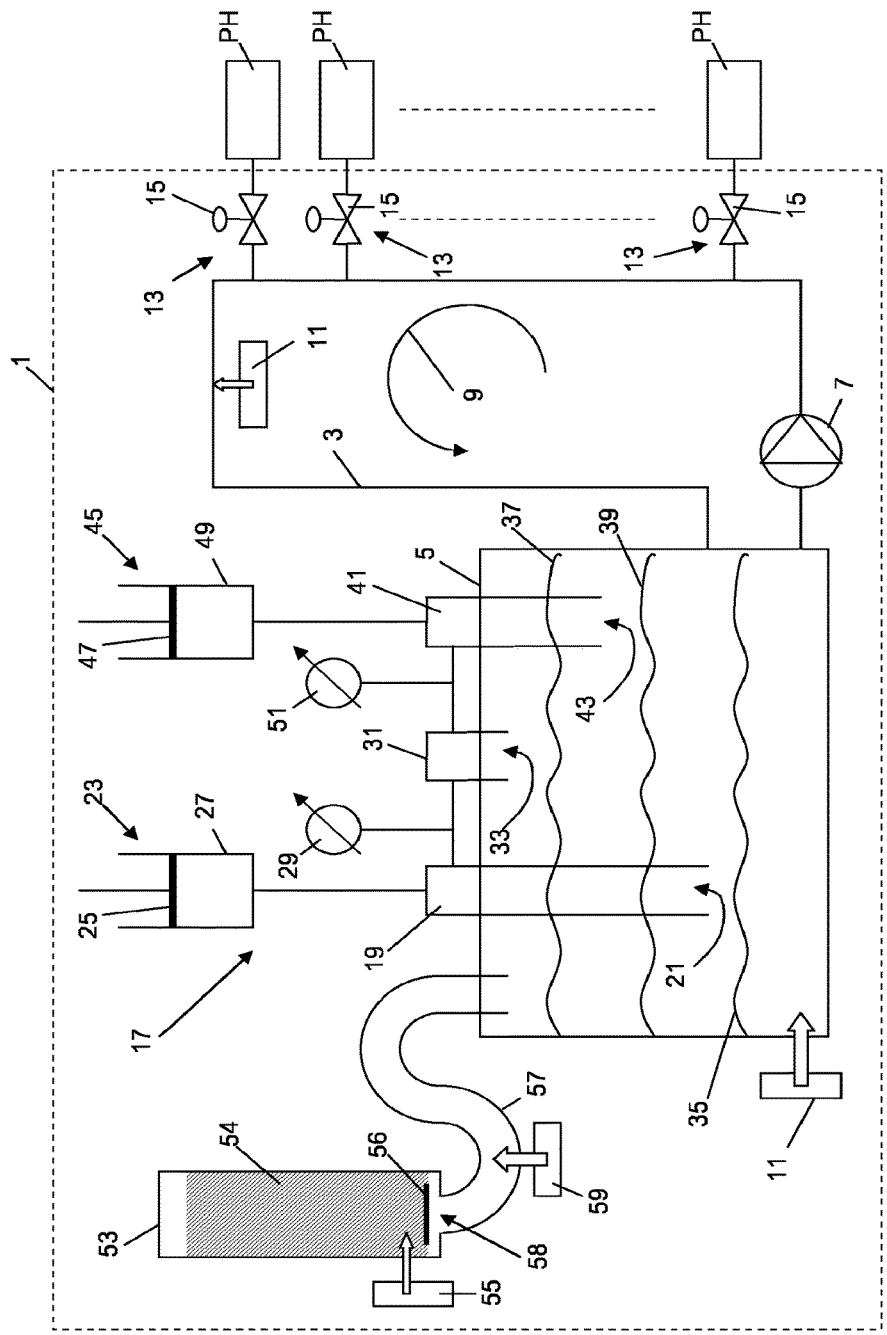
Figure 7:
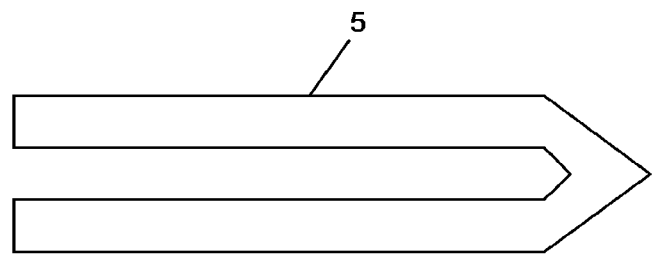
Figure 8:
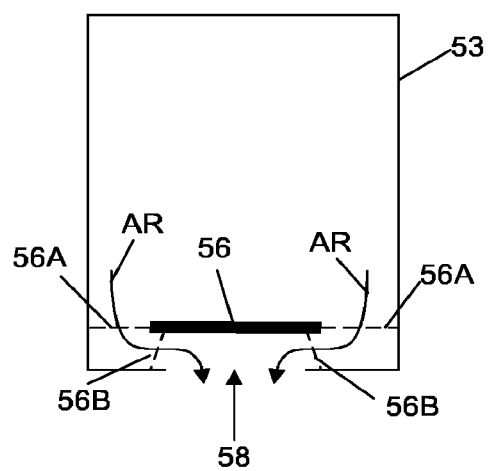
Figure 9:
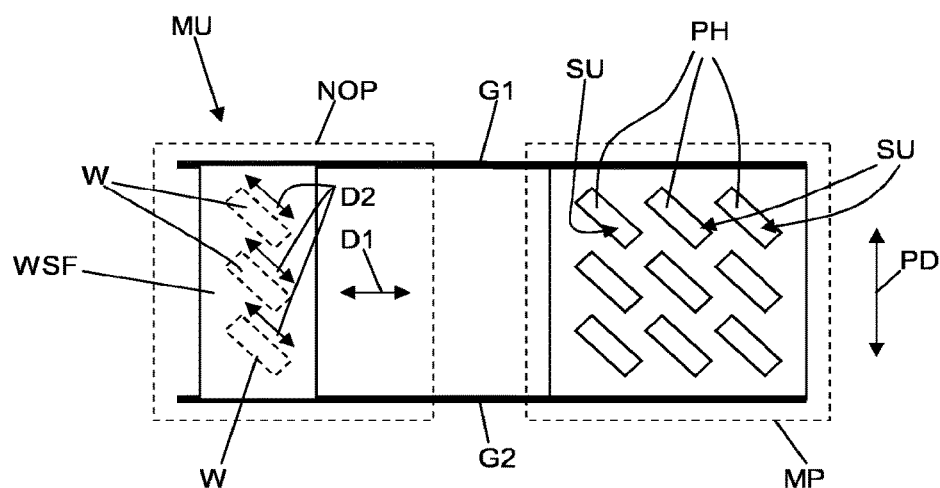
Figure 10A:
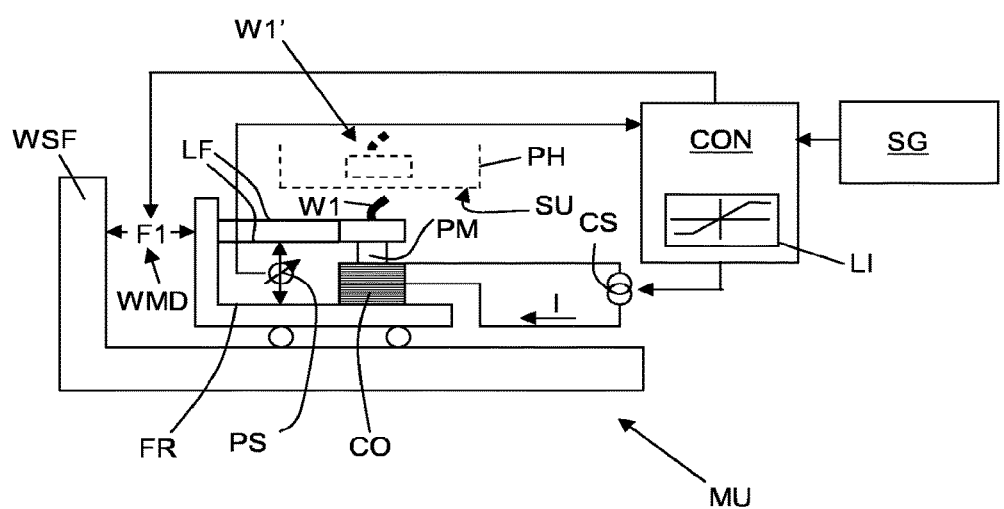
Figure 10B:
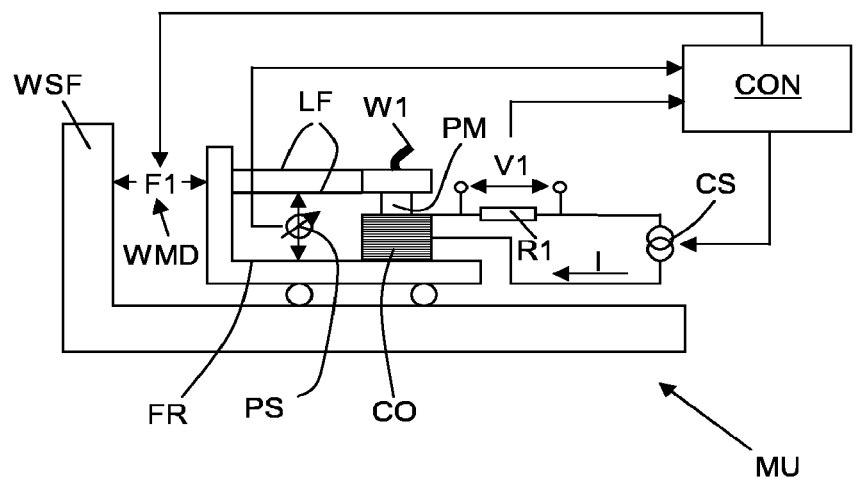
Figure 11A:
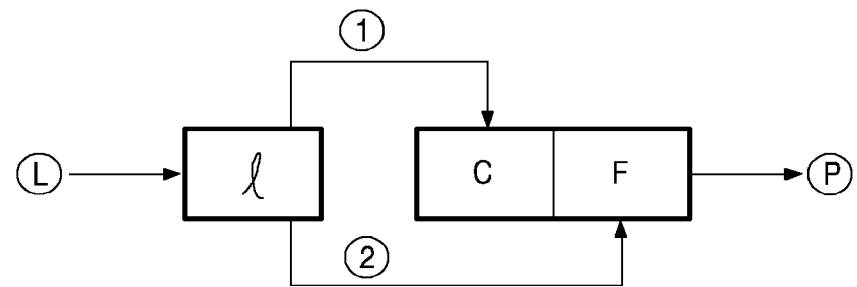
Figure 11B:
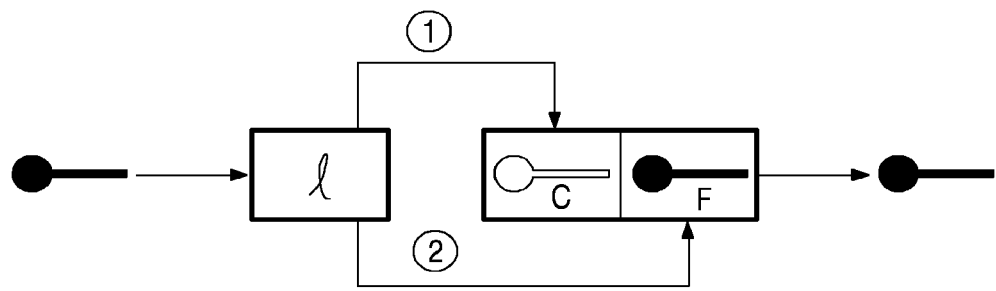
Figure 12:
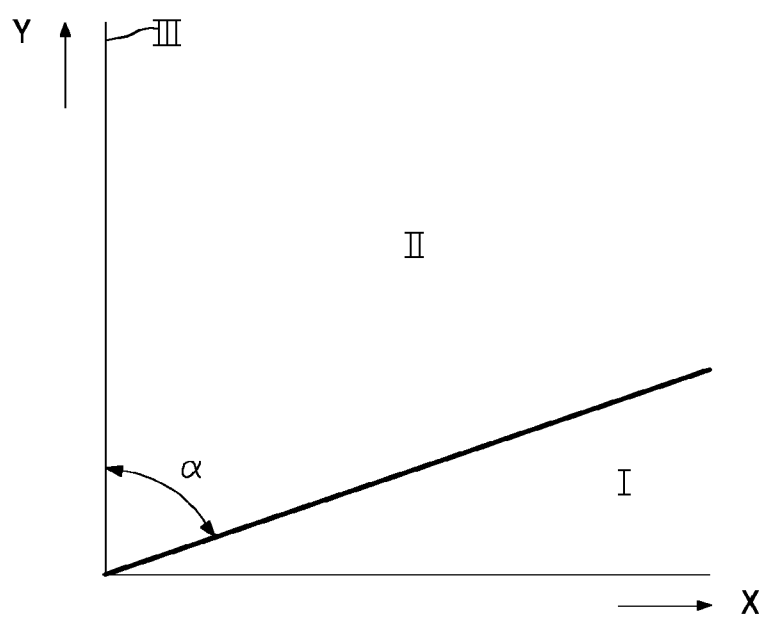
Figure 14:
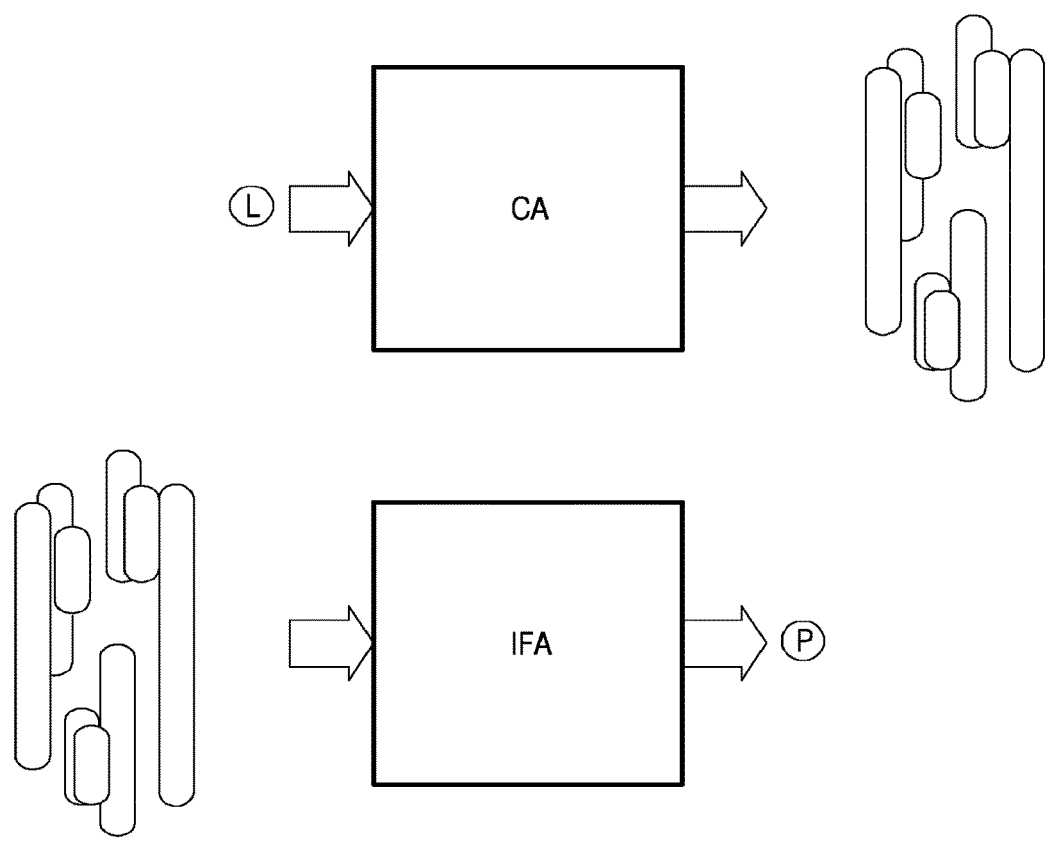
Figure 15:
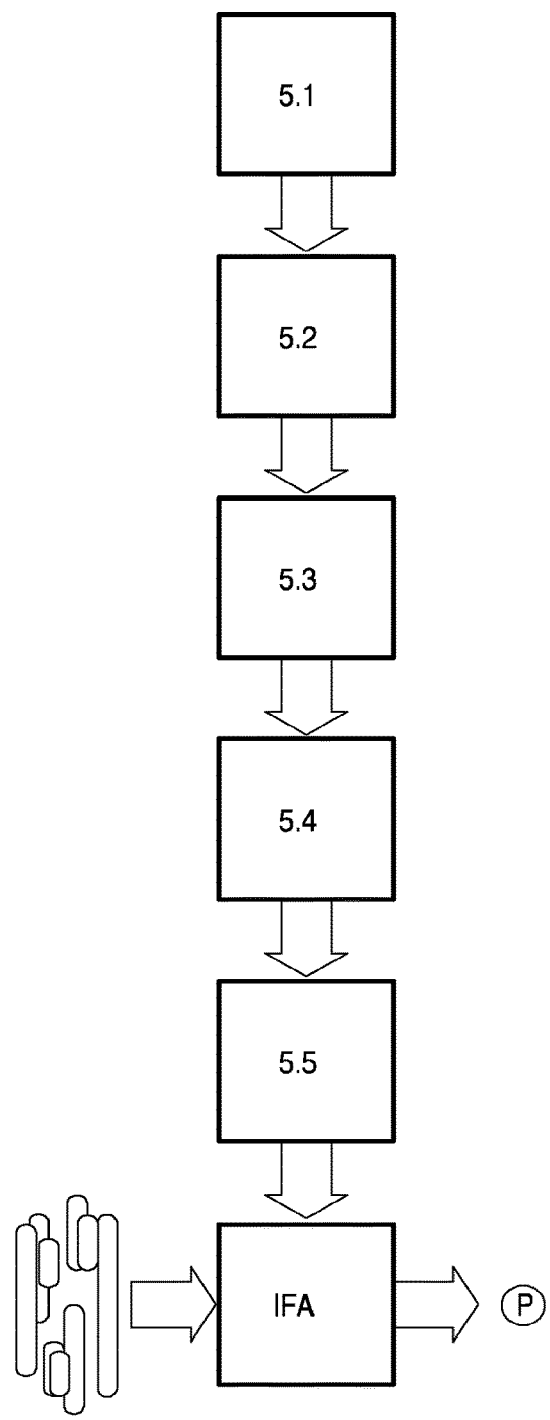
Figure 16A:
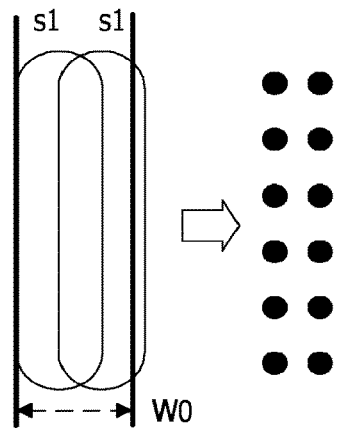
Figure 16B:
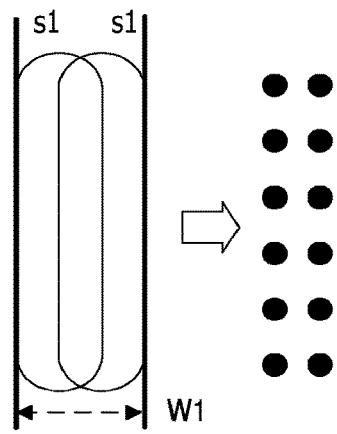
Figure 16C:
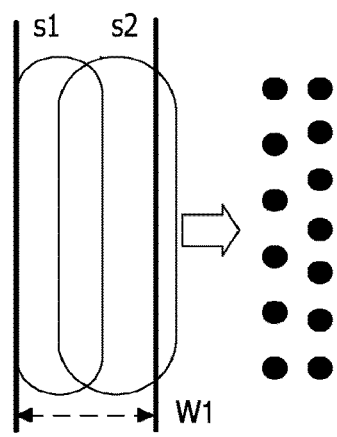
Figure 17A:
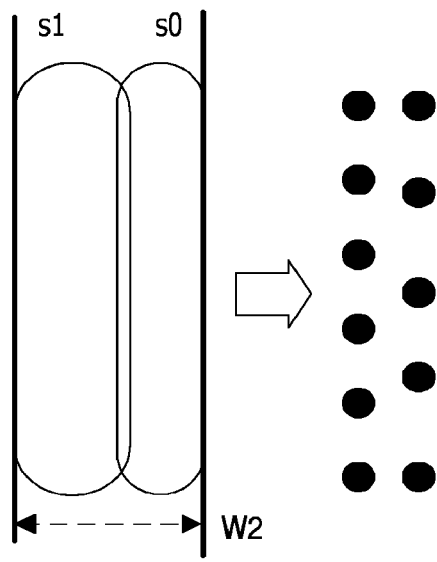
Figure 17B:
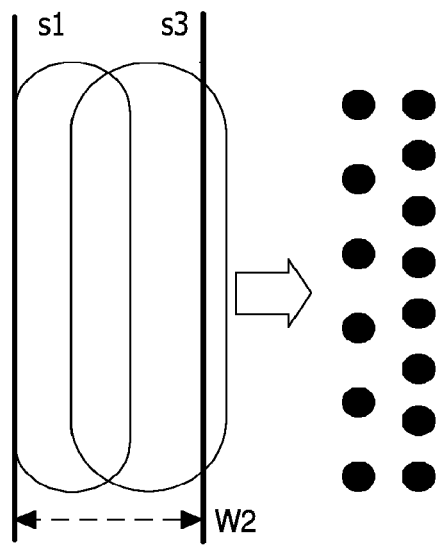
Figure 18:
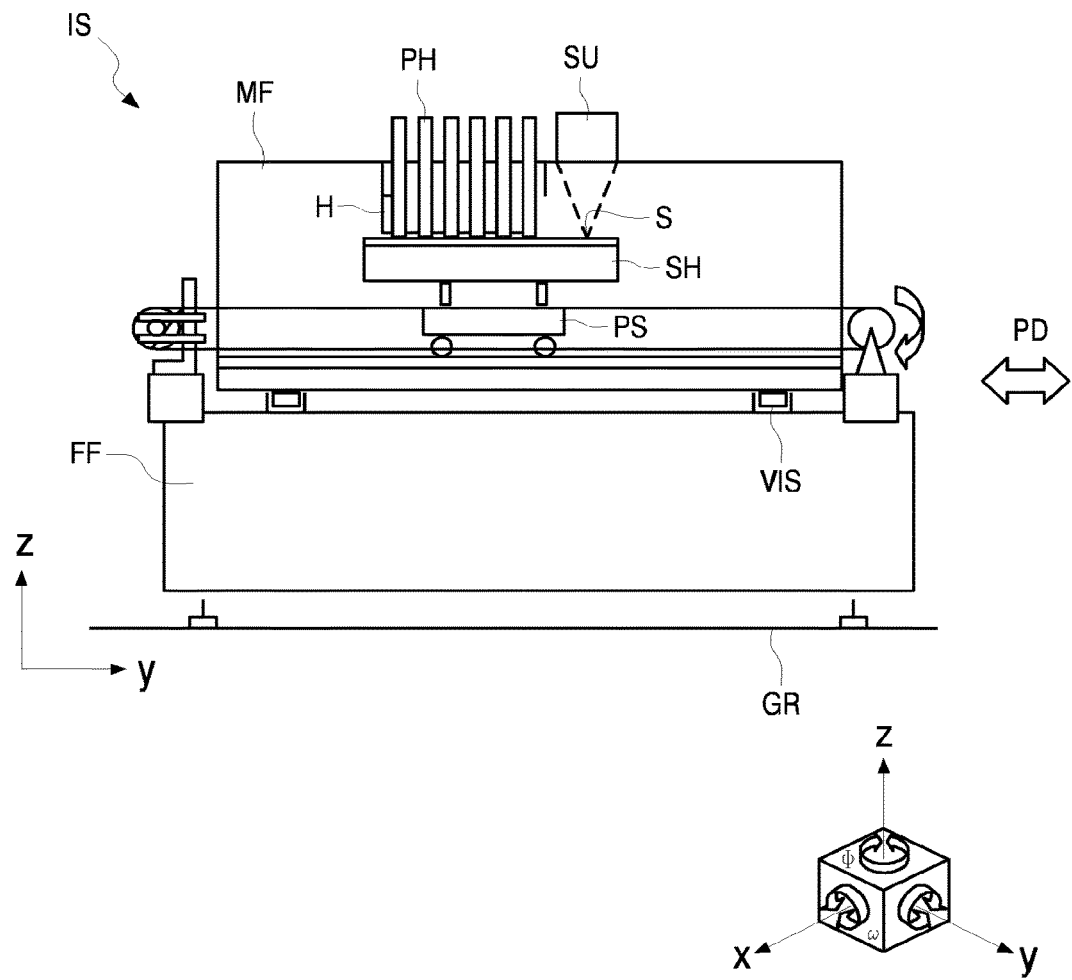
Figure 19:
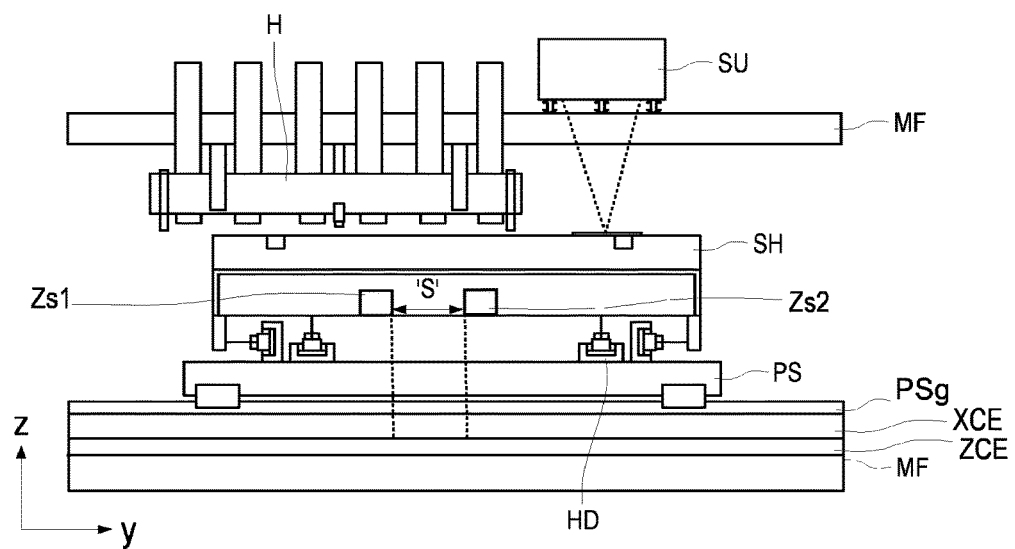
Figure 20:
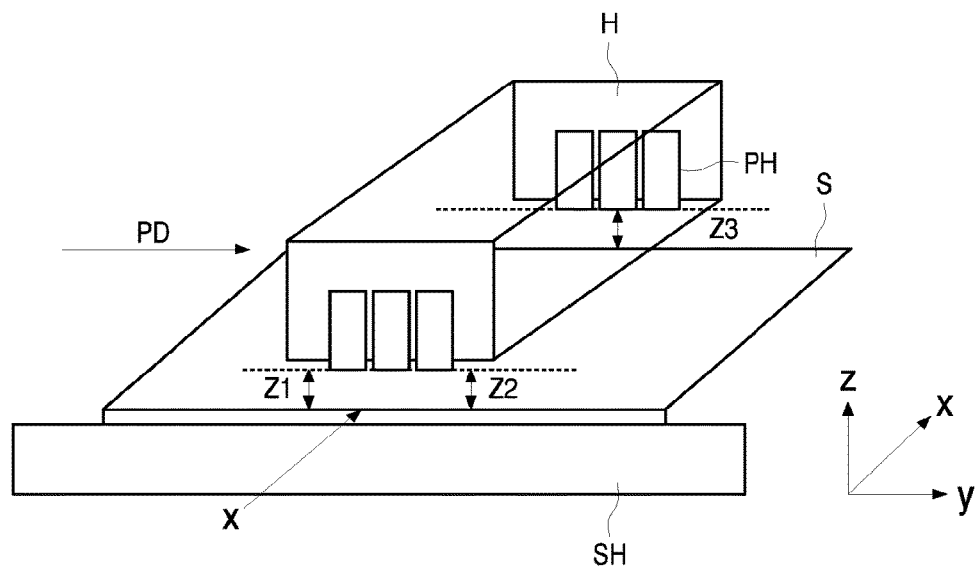
Figure 21:
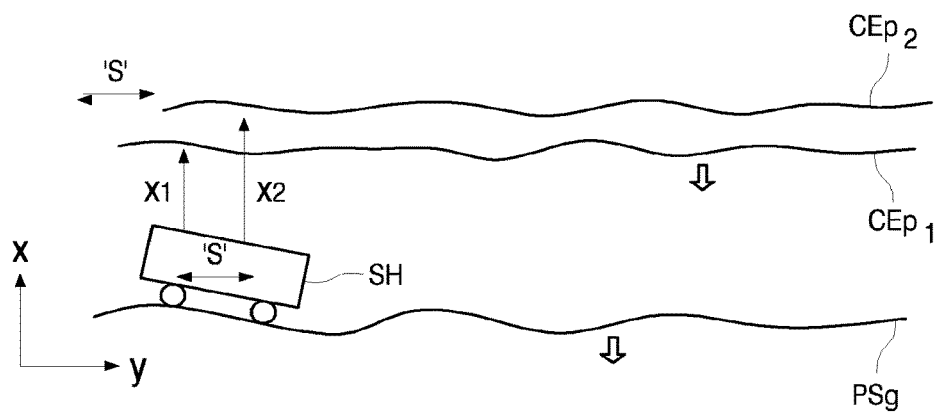
Figure 22:
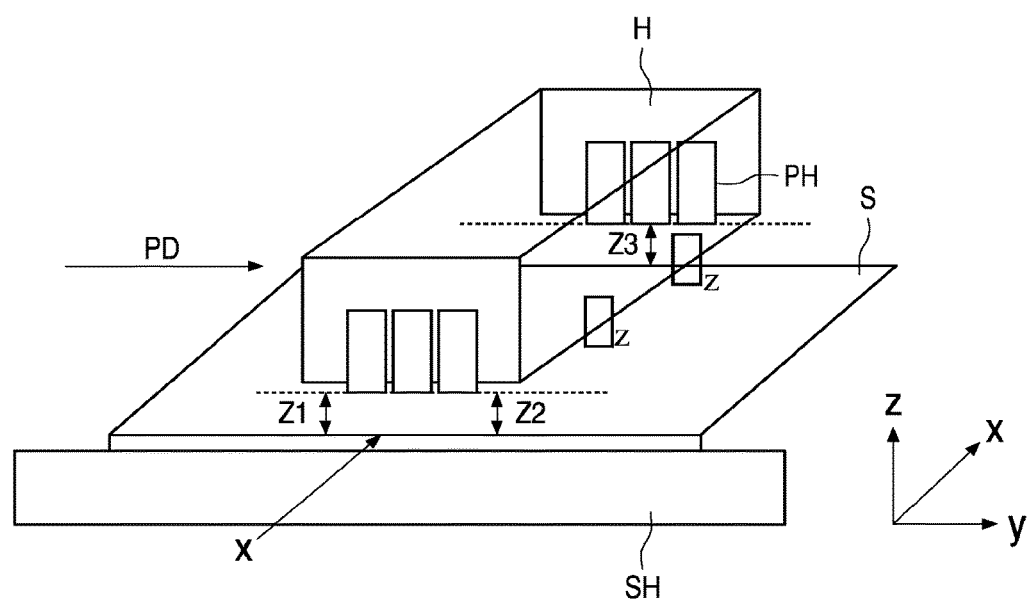
Figures 23A, 23B:
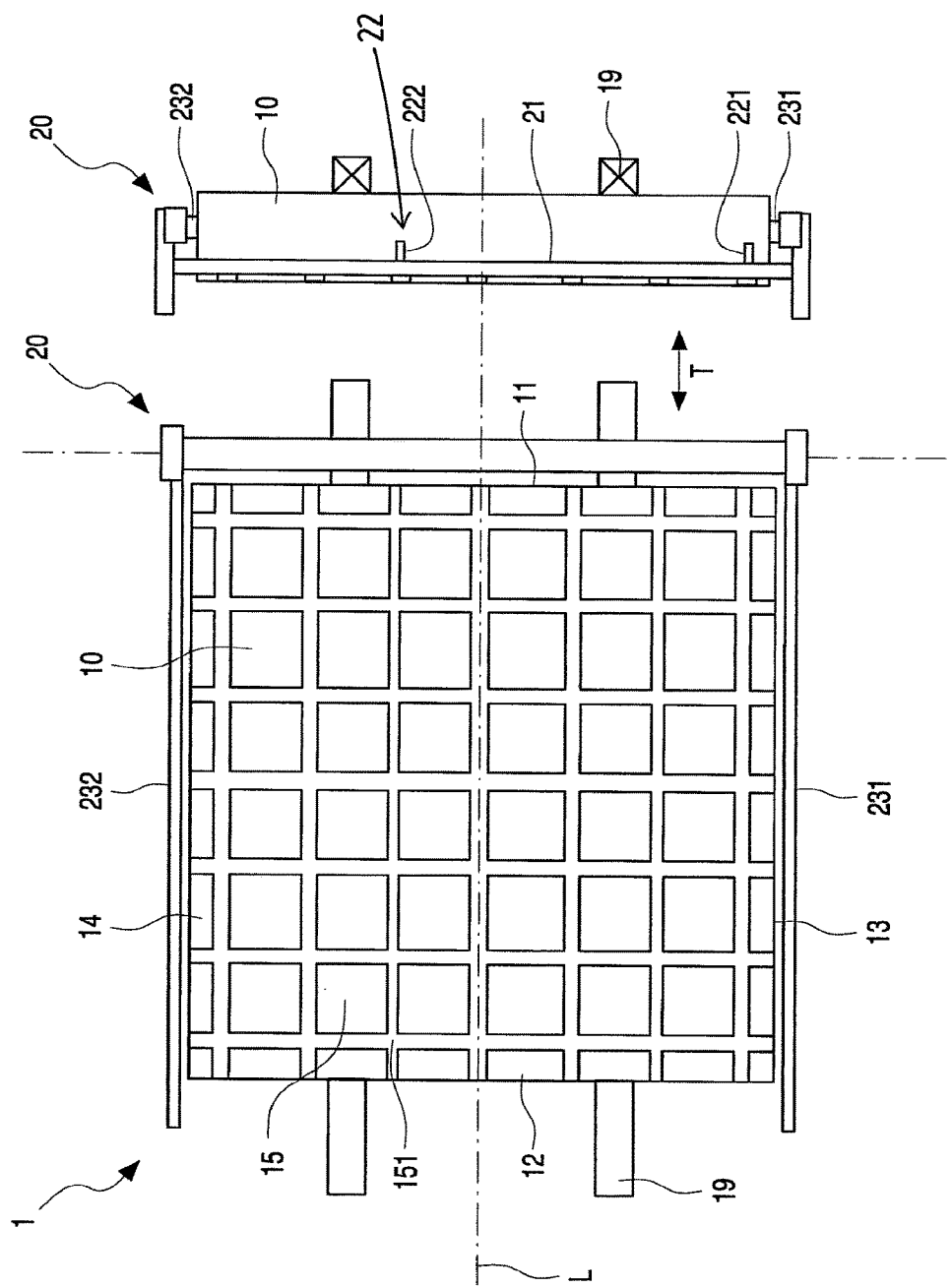
Figure 24A:
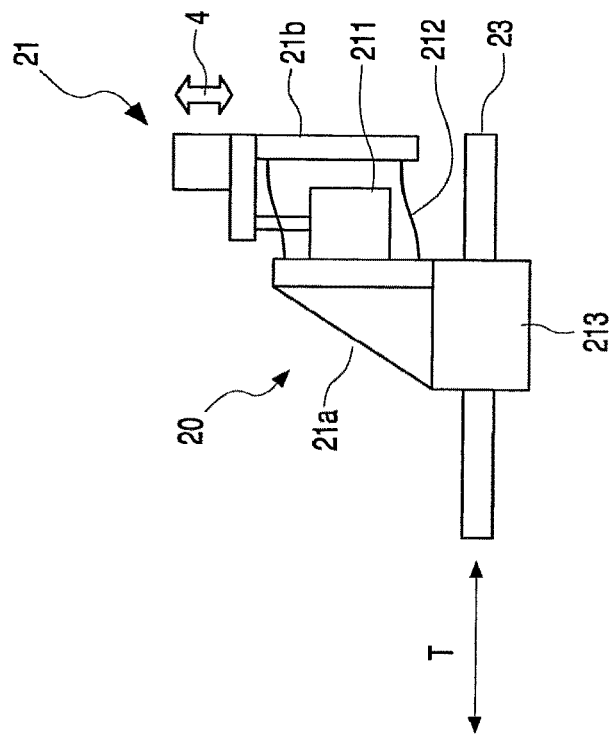
Figure 24B:
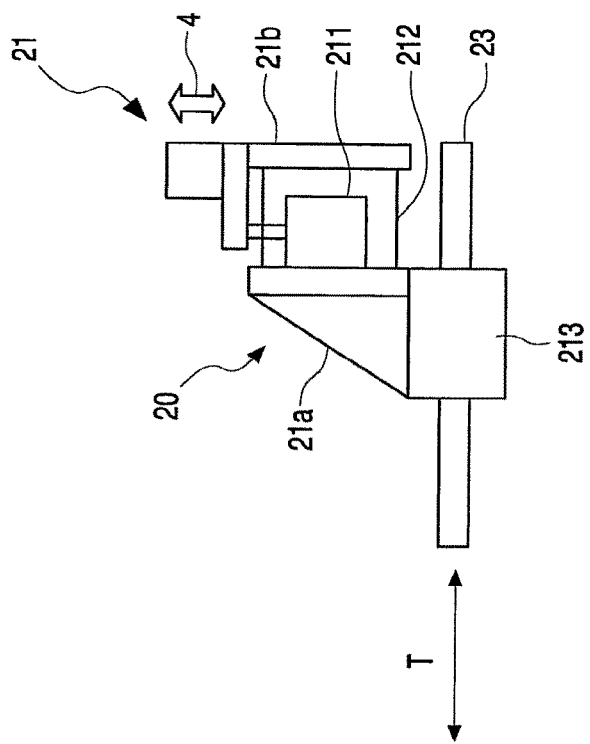
Figure 25A:
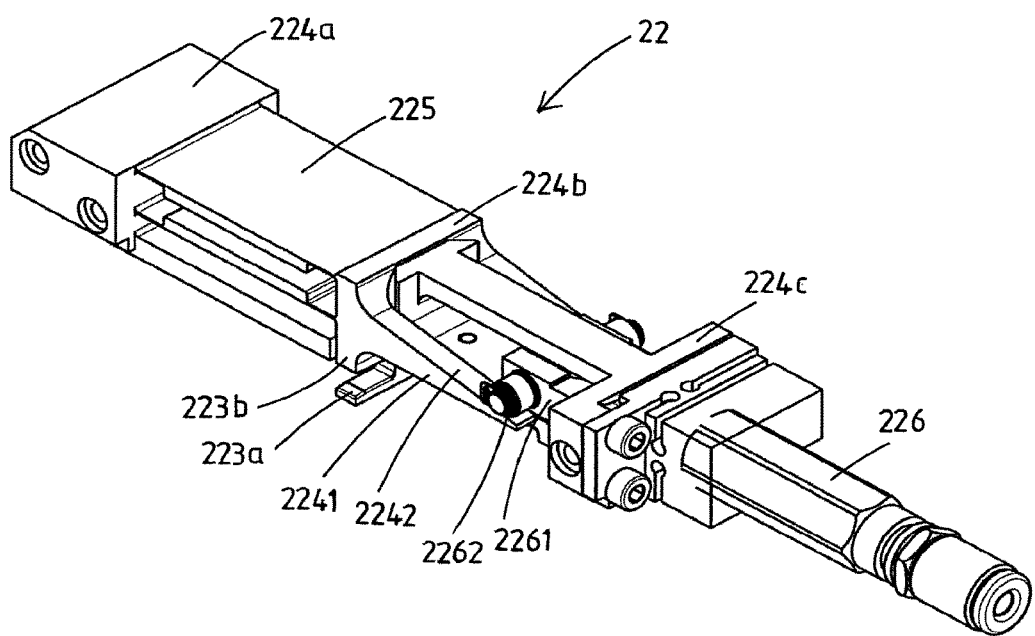

in particular with respect to second aspect,

FIG. 3 depicts an inkjet system according to an embodiment of in particular the second, third and fourth aspect of the invention;

FIG. 4 depicts a schematic top view of a print head assembly of the inkjet system of FIG. 3;

FIG. 5 depicts a schematic view of a print head positioning device according to a second aspect of the invention suitable to position a print head in the inkjet system of FIG. 3;

in particular with respect to third aspect,

FIG. 6 depicts schematically a hot-melt ink dosing system according to the invention FIG. 7 depicts schematically a reservoir of the dosing system of FIG. 6 and FIG. 8 depicts schematically a hot-melt ink cartridge according to the invention in particular with respect to the first and second subaspect of the fourth aspect, FIG. 9 depicts a part of the inkjet system of FIG. 3 and shows schematically a maintenance unit according to an embodiment of the invention;

FIG. 10A depicts in more detail a part of a maintenance unit according to an embodiment of the first subaspect of the fourth aspect of the invention, which is suitable to be used in the inkjet system of FIG. 3;

FIG. 10B depicts in more detail a part of a maintenance unit according to an embodiment of the second subaspect of the fourth aspect of the invention, which is suitable to be used in the inkjet system of FIG. 3.

in particular with respect to the fifth aspect,

FIG. 11a shows a flow chart of the method according to the fifth aspect of the invention for printing an ink pattern;

FIG. 11b shows the flow chart of FIG. 11a including an example of a pattern layout;

FIG. 12 shows a classification system in a Cartesian system;

FIGS. 13a-13d show several examples of orientations of contours in several directions;

FIG. 14 shows a flow chart, wherein the contour print algorithm is subdivided into a coverage algorithm and an ink flow algorithm;

FIG. 15 shows a flow chart of the ink flow algorithm, wherein a set of coverage elements is converted to an ink pattern;

FIG. 16a shows a combination of coverage elements which include a narrowing effect as an ink flow effect;

FIG. 16b shows the same combination of two coverage elements as shown in FIG. 16a, but by applying another time interval;

FIG. 16c shows an alternative combination of coverage elements to achieve an ink pattern with a certain width; and FIGS. 17a and 17b show a further exemplary illustration of two different combinations of test patterns.

in particular with respect to the sixth aspect,

FIG. 18 shows in a schematic view an inkjet system according to the sixth aspect of the invention;

FIG. 19 shows in a cross-sectional view the inkjet system of FIG. 18;

FIG. 20 shows a printhead assembly in a schematic view in detail, which print head assembly is spaced from a substrate on a substrate holder in a vertical direction;

FIG. 21 shows in a schematic view a step of a calibration method to deliberate a substrate holder in a lateral direction; and FIG. 22 shows a printhead assembly in a schematic view in detail, which print head holder is provided with additional Z-sensors.

in particular with respect to the seventh aspect,

FIG. 23a shows in a top view an embodiment of the substrate conveyor according to the invention;

FIG. 23b shows in a front view the substrate conveyor as shown in FIG. 23a;

FIG. 24a shows in a side view a transfer unit in a lower position;

FIG. 24b shows in a side view the transfer unit in an upper position;

FIG. 25a shows in a perspective view a gripper of the transfer unit; and

Figure 25B:
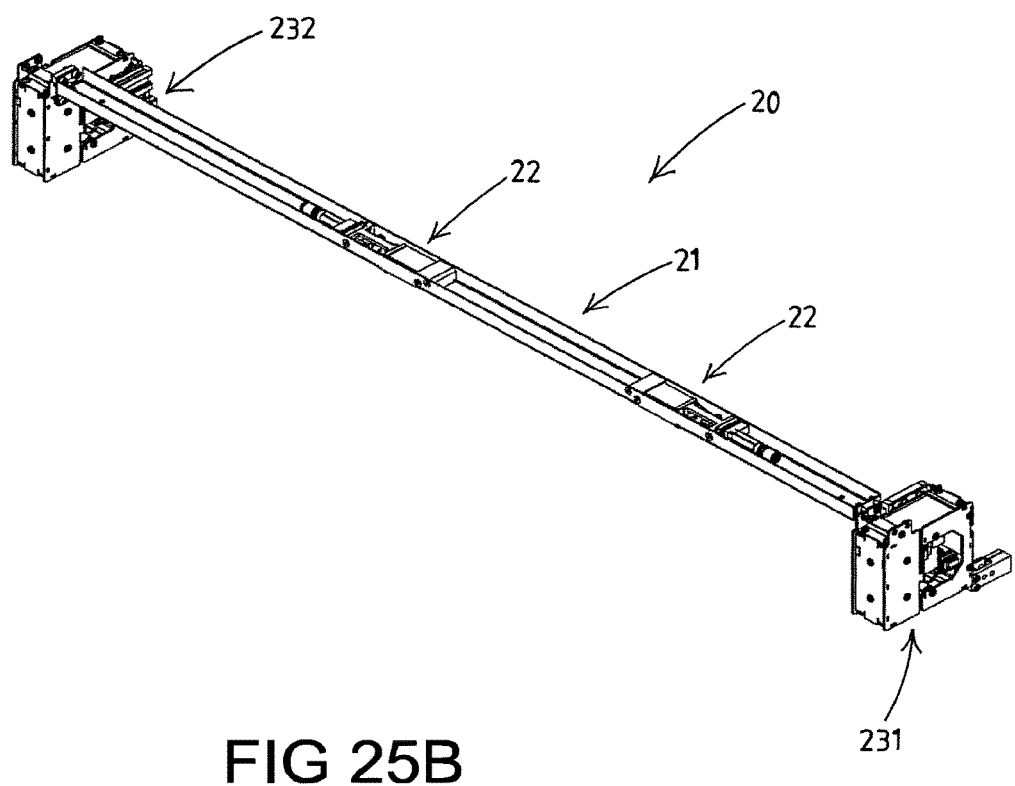

FIG. 25b shows in a perspective view the gripper of FIG. 25a mounted to a transfer unit.

A printed circuit board, called a PCB, is used to mechanically support and electrically connect electronic components. A PCB is also referred to as printed wiring board (PWB) or etched wiring board. Printed circuit boards are used in virtually all but the simplest commercially produced electronic devices. A PCB comprises a substrate which includes at least one conductive pathway etched from at least one copper sheet laminated onto a non-conductive base panel. The substrate has a base panel which is non-conductive. The base panel comprises typically a resin bounded fibres. The base panel is typically formed by insulating layers dielectric which are laminated together with epoxy resin. The board is typically coated with a solder mask that is mostly green in colour. The non-conductive base panel is laminated with at least one copper sheet to form a blank PCB, or simply called 'a blank'. A blank forms a base product for manufacturing a PCB.

A printed circuit board can be manufactured in several manners. To manufacture PCB's in large volumes and with fine line widths to create tracks or signal traces, it is general practise to manufacture the PCB by a photographic process. In the photographic process a photoengraving step is carried out which uses a photomask and developer to selectively remove a photo resist coating. The remaining photo resist protects the copper sheet. Subsequent etching removes unwanted copper. The photomask is usually prepared with a photo plotter from data produced by a technician using CAM, or computer-aided manufacturing software.

In this application, the manufacturing of the printed circuit board comprises a step of printing an etch resistant ink onto the substrate by an inkjet system instead of using a photographic process. The etch resistant ink, or simply called 'resist', is dropped onto a surface of the blank by an inkjet system. The etch resistant ink is applied onto the blank to cover copper areas which have to be maintained during a later etching operation. After applying the resist, the substrate is etched to remove the copper sheet outside the covered areas.

Figure 1A:
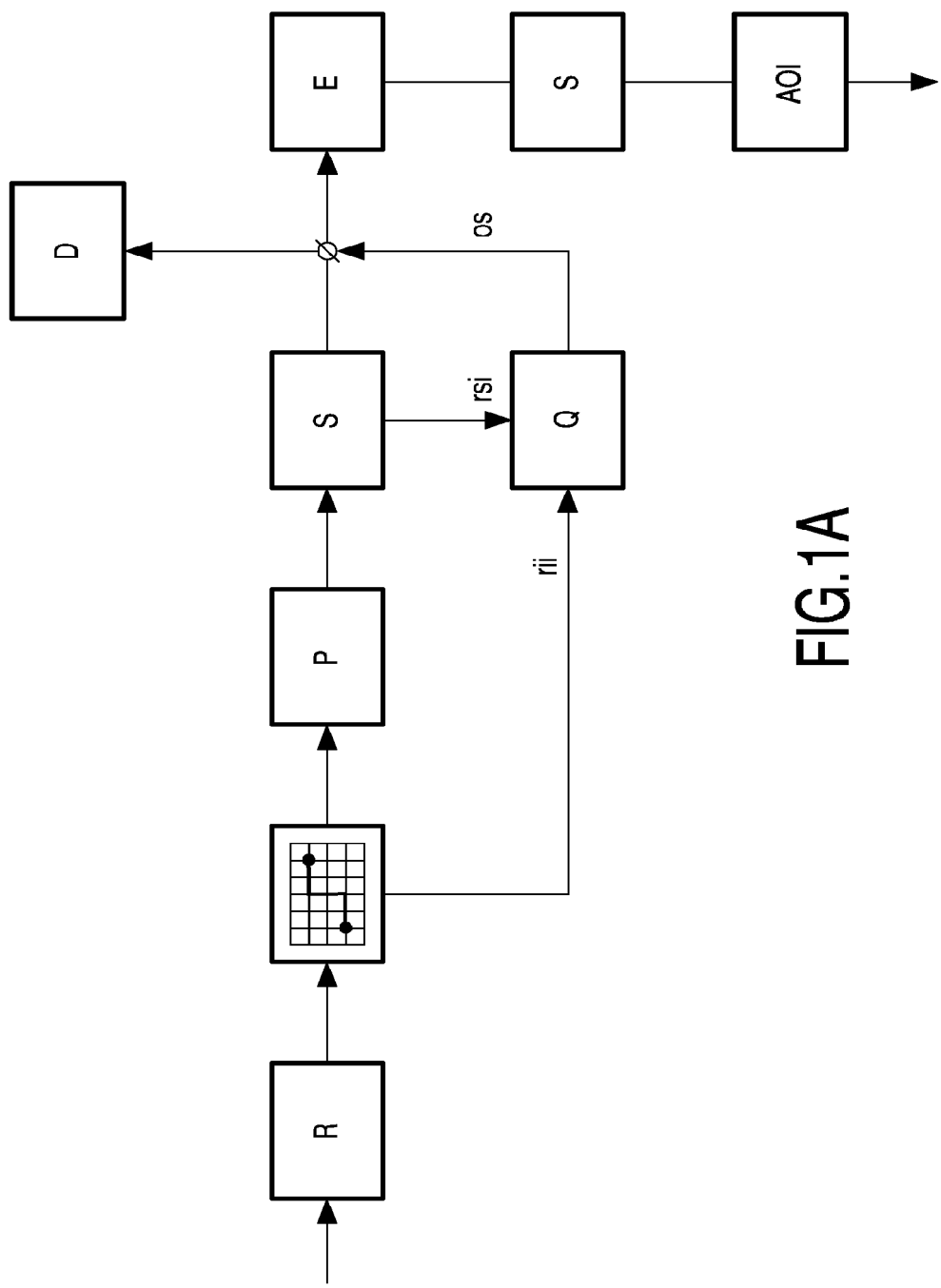
FIG. 1A shows a flow scheme of a printing process including a quality inspection according to a first aspect of the invention.

FIG. 1A shows in a flow scheme successive steps of a method for manufacturing a printed circuit board. The manufacturing of the printed circuit board is carried out by an inkjet system for printing an electronic substrate. The inkjet system comprises a print head assembly for ejecting droplets of ink on a substrate and control electronics for controlling the inkjet system. The flow scheme shows a first step, an initial step, in which a pattern layout is received by the inkjet system. The pattern layout defines a desired layout of an ink pattern to be printed onto the substrate. The pattern layout is digitally received by control electronics. The pattern layout comprises software data. The pattern layout may be submitted to the control electronics by a transfer via a network or data carrier like a memory stick. The received pattern layout defines a desired layout of the PCB which has to be produced. The pattern layout may already comprise a raster image, but typically, the pattern layout as provided represents a vector image of a desired PCB. The received pattern layout comprises data which can be read out or converted by the inkjet system. The pattern layout may be read out and defined as a raster input image or read out and converted to a raster input image by the control electronics of the inkjet system.

After receiving the pattern layout, a step is carried out, a rasterizing step R, in which the received pattern layout is read out, converted or adapted into an raster input image 'rii' by the control electronics of the inkjet system. The obtained raster input image 'rii' complies to technical input requirements of an inkjet system which is used in the manufacturing method. The input requirements may depend on technical specifications of the inkjet system, like an amount and positioning of available nozzles of the printhead assembly. The raster input image is a dot matrix data structure and provides a grid for allocating ink dot positions. Generally, the grid is a rectangular grid. The raster input image provides a two dimensional representation of the ink pattern in an X-Y plane of ink dot positions. The raster image provides for each ink dot of the ink pattern a length Y and width X coordinate.

In a next third step, a printing step P, an ink pattern is printed by dropping ink dots onto the substrate by the printhead assembly of the inkjet system. Based on the raster input image, the ink pattern is printed onto the substrate. The printhead assembly is arranged for dropping ink droplets onto a top surface of the substrate and has a plurality of nozzles for ejecting ink droplets. In the inkjet system, the printhead assembly is arranged above a substrate conveyor for conveying the substrate. By driving the substrate conveyor, a substrate is movable underneath the printhead assembly.

In a next fourth step, a scanning step S, the printed ink pattern is scanned by a scanning unit of the inkjet system. The scanning unit is arranged to scan the printed ink pattern on the top surface of the substrate. By scanning the top surface of the printed substrate, a raster scan image is obtained of the printed ink pattern. The scanning unit captures a raster scan image 'rsi' from the ink pattern of the printed substrate.

During a next step Q, a quality inspection is carried out. The quality inspection is carried out by the control electronics of the inkjet system. The quality inspection is carried out inline. The quality inspection is carried out during the presence of the printed substrate in the inkjet system. The printed substrate may stay at a scanning or printing area of the inkjet system during a carrying out of the quality inspection. The printing area may be defined as an area in which a substrate moves during a printing operation. The scanning area may lie adjacent to the printing area. The printed substrate may stay in a buffer area of the inkjet system during the quality inspection. The buffer area is integrated in the inkjet system. The buffer area is inline positioned in the inkjet system. The quality inspection is carried out by the control electronics of the inkjet system. During the quality inspection, the obtained raster scan image 'rsi' is compared with the raster input image 'rii' and a decision is made to approve or reject a printed substrate. After the quality inspection an output signal 'os' is provided to indicated a further processing of the printed substrate. A first output signal may indicate an approved substrate which can subsequently be forwarded to an etch station for etching the substrate. A second output signal may be provided to indicate a rejected, disapproved substrate which is subsequently discharged e.g. to a recycle station.

After carrying out the inline quality inspection, an approved printed substrate is further processed by forwarding the printed substrate to a next to the inkjet system positioned process station. A next process station may be a subsequent inkjet system for printing a bottomside of the substrate or an etch station for etching the printed substrate. Subsequently, the substrate may be forwarded to a stripping station for stripping the ink pattern from the substrate to expose a conductive pattern. In a final step, the substrate may be inspected by an automated optical inspection unit. The automated optical inspection may be carried out to inspect only on typical failures of the conductive pattern which have been occurred during etching or stripping. After the final inspection, the substrate may be definitively approved for use.

After carrying out the in-line quality inspection, a rejected printed substrate may be discharged from the inkjet system. The rejected substrate may be discharged to a discharge station D which is positioned adjacent the inkjet system. The discharge station D may be a recycle station for recycling rejected substrates or a storage station for storing rejected substrates. The recycle station may comprise a cleaning unit for removing an ink pattern from a rejected substrate. Cleaned substrates may be reused and inputted into the inkjet system.

Figure 1B:
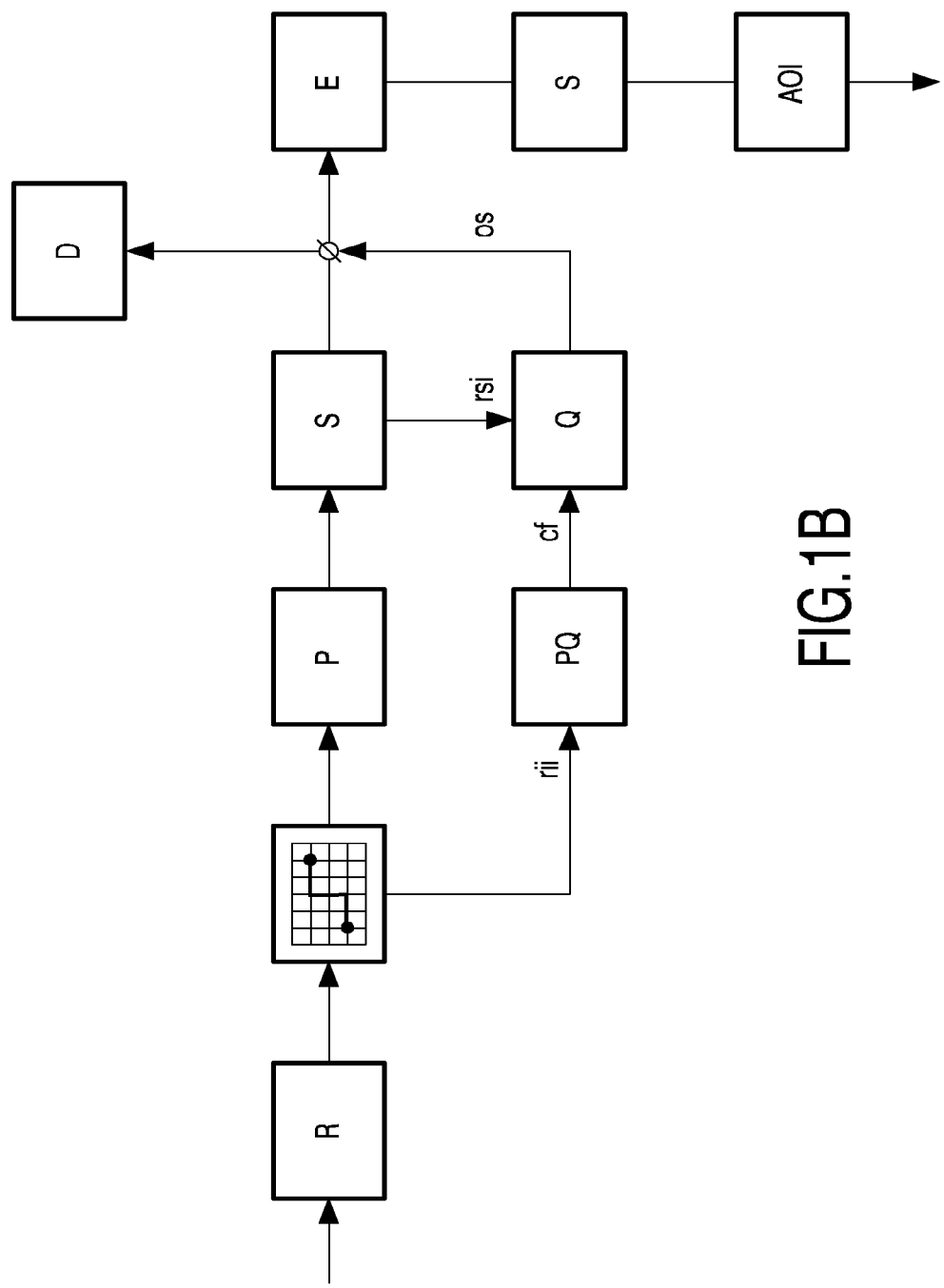
FIG. 1B shows the flow scheme of FIG. 1A further elaborated with a preparing step of extracting control features from a raster input image.

FIG. 1B shows a further elaborated flow scheme of a printing process including an inline quality inspection Q. The quality inspection Q is improved by a preparing step of extracting at least one control feature 'cf' from a raster input image 'rii'. A control feature may define a particular part i.e. a position or a geometry of the raster input image which is susceptible to a print failure. The control features may define a print region of the ink pattern which has a higher risk on a print failure during a printing process. During the preparing quality inspection step, features of the raster input image which might contribute to a higher risk of misprints are recognised.

Figure 2:
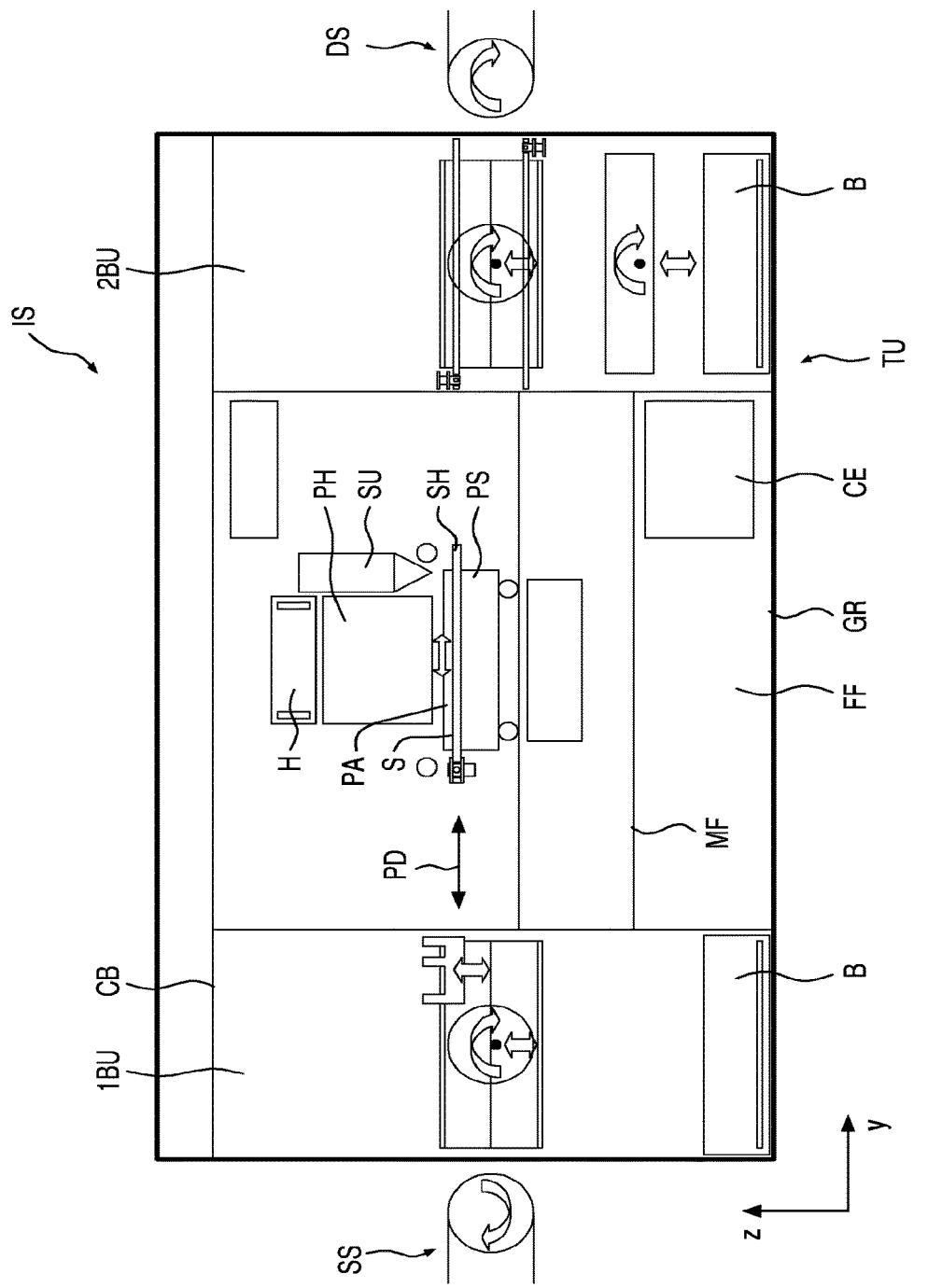
FIG. 2 shows in a schematic view an inkjet system which is configured to carry out the printing process as shown in FIG. 1A.

FIG. 2 depicts an inkjet system IS according to an embodiment of in particular a first aspect of the invention for depositing material in a desired ink pattern on a substrate S by jetting liquid droplets of the material towards the substrate. The inkjet system is preferably a drop-on-demand inkjet system in which a droplet is only jetted when required. This is in contrast to continuous inkjet systems in which droplets are continuously jetted at a predetermined frequency and wherein droplets required to form the pattern are directed towards the substrate and the remaining droplets are captured and thus prevented from reaching the substrate.

The inkjet system of FIG. 2 is an industrial inkjet system IS, for instance an inkjet system used to deposit resist material as a mask layer on a printed circuit board as an alternative to the more traditional process of providing a mask layer using lithography. Because the mask layer can be deposited directly by the inkjet system, the amount of process steps can be reduced dramatically and thus the time for PCB manufacturing. Such an application requires a high droplet placement accuracy and a high reliability (every droplet counts).

The inkjet system IS is in particular suitable to be used in the method according to the invention. The applied material is in particular ink, also called resist. The ink pattern has to be produced according to an available pattern layout. In a first step, the pattern layout is supplied to control electronics CE of the inkjet system.

An orthogonal system including an X, Y and Z-axis may be projected onto the inkjet system.

The Y-axis is a longitudinal axis. The Y-axis may be defined as a direction extending in a printing direction. The printing direction of the inkjet system is defined as a direction of movement of a substrate when passing a print head assembly to print a swath onto the substrate. The printing direction corresponds with a travel of the substrate positioning stage. The travel of the substrate positioning stage corresponds with a largest stroke of the substrate with respect to the printing assembly.

The X-axis may be defined as a direction perpendicular to the Y-axis. The X-axis extends in a direction transversal the printing direction. The X-axis is a lateral axis. The X-axis and Y-axis define a substantially horizontal plane in the inkjet system.

The Z-axis may be defined as a direction perpendicular to the X- and Y-axis. The Z-axis extends in upwards direction. The Z-axis is an up-down axis. The Z-axis extends in a substantially vertical direction.

A rotational direction about the X-axis Rx, a pitch motion, may be defined as a rotation of the substrate about the lateral axis.

A rotational direction about the Y-axis Ry, a roll motion, may be defined as a rotation of the substrate about a longitudinal axis. The longitudinal axis extends from a front to a back of the substrate.

A rotational direction about the Z-axis Rz, a yaw motion, may be defined as a rotation of the substrate about the up-down axis.

The inkjet system IS comprises a climate box CB for generating a climate controlled zone around components of the inkjet system IS. The climate box comprises a temperature control means for generating stable climate conditions during printing.

To provide a high accuracy inkjet system, the inkjet system IS comprises a framework including a force frame FF which supports a metrology frame MF from the ground GR. Between the force frame FF and the metrology frame MF a vibration isolation system is provided to support the metrology frame MF from the force frame FF while isolating the metrology frame MF from vibrations in the force frame FF. As a result, a relatively steady and quiet printing environment can be created on the metrology frame which is advantageous for accuracy.

The inkjet system further comprises a print head holder H. Here, the print head holder H is stationary mounted in the inkjet system. The print head holder H is fixedly connected to the metrology frame MF. The print head holder has a shape of a beam. The print head holder extends in an X-direction. The print head holder bridges a printing area PA in which an ink pattern is supplied to a surface of a substrate S. The print head holder holds a print head assembly which comprises at least one print head PH. Each print head PH comprises one or more, typically dozens of, nozzles from which droplets can be ejected towards the substrate S. The print head assembly defines a printing range in the X-direction in which droplets can be placed during a forward or backward swath. The printing range in X-direction defines a width of the printing area PA. A distance in between a first and last nozzle in a row of nozzles in Y-direction defines a length of the printing area PA.

Further, the inkjet system comprises a substrate holder SH to hold a substrate S.

The substrate holder SH is moveable relative to the print head PH and scanning unit SU in the printing direction PD parallel to the Y-direction in order to let a substrate S pass below the print head assembly.

In the embodiment, the print head assembly has a printing range in X-direction at least as large as the largest possible dimension in X-direction of a substrate the substrate holder SH can handle. The print head assembly is mounted stationary with respect to the metrology frame MF.

In the embodiment of FIG. 2, the substrate holder SH is supported by a substrate positioning stage PS. The substrate positioning stage PS is supported by the metrology frame MF. The substrate positioning stage PS is supported by the metrology frame such that it is moveable in the printing direction PD, thereby allowing to position the substrate holder SH and thus the substrate S in the Y-direction. Positioning of the substrate positioning stage is done using a stage positioning device SD. The stage positioning device comprises a stage guidance, a stage position measuring system and a stage actuator.

The stage guidance is a linear guidance. The stage guidance comprises a pair of bar elements to support and guide the substrate positioning stage. The substrate positioning stage is beared to the stage guidance by ball bearings. The stage guidance is connected to the metrology frame MF. Herewith, vibrations from the ground do not disturb a linear guidance of the substrate positioning stage.

The stage position measuring system comprises a linear encoder. The linear encoder includes an elongated ruler which extends in Y-direction and an optical reader which is mounted to the substrate positioning stage. In operation, the substrate positioning stage passes along the ruler to obtain an Y-position of the substrate positioning stage.

The stage actuator comprises a belt and a driving member. The substrate positioning stage is connected to the driving element by the belt. The driving element is mounted to the force frame FF. The driving element may include a gearwheel and a motor. Herewith, driving forces F are applied between the substrate positioning stage PS and the force frame FF. As a result, the driving forces F do not introduce disturbances to the metrology frame MF, but are transmitted to the ground GR via the force frame, which results in a higher obtainable accuracy of the inkjet system.

FIG. 2 further shows a scanning unit SU for scanning an ink pattern which is printed on a substrate. The scanning unit SU is fixedly connected to the metrology frame MF. In particular, the scanning unit SU is mounted to the print head holder H. The scanning unit SU is positioned adjacent the printing area PA. The scanning unit SU comprises a light source for illuminating at least a part of the ink pattern of the substrate. Further, the scanning unit SU comprises an imaging unit for capturing a scan image, in particular a raster scan image. The light source generates an illumination of the ink pattern in a specific light colour. Preferably, the light source is monochrome, in which an emitted light colour of the light source is tuned to an extreme reflection value of the ink pattern and/or background surface.

Control electronics CE are provided to control the inkjet system IS. In particular, the control electronics are arranged to control the position and speed of the substrate positioning stage. A constant speed of the substrate positioning stage is required, because of the constant frequency of jetted droplets. A variation in speed of the substrate passing a print head may cause gaps in a jetted track.

The control electronics CE are further configured to control a stream of substrates in the inkjet system. During the printing process the stream of substrates S are moved through the inkjet system IS. An initial blank substrate S can be supplied to the inkjet system IS by a supply station SS for supplying blank substrates e.g. a supply conveyor. The inkjet system IS may have a first buffer unit 1BU at an entrance of the inkjet system for receiving blank substrates from the supply station SS. The first buffer unit 1BU is positioned inside the climate box CB. The buffer unit BU provides a buffer area for temporary storing a substrate S. The first buffer unit 1BU may buffer received substrates from the supply station, such that the supplied substrates acclimate to stable conditions. After stabilizing, the blank substrates are transferred from the first buffer unit 1BU to the substrate holder SH into the printing area PA of the inkjet system for printing a surface of the substrate S. The first buffer unit may be a turn buffer unit. The inkjet system IS may have a second buffer unit 2BU for buffering substrates before discharging printed substrates away from the inkjet system IS. The second buffer unit 2BU is positioned inside the climate box CB adjacent the metrology frame MF at an exit of the inkjet system. A printed substrate may be transferred from the substrate holder SH to the second buffer unit 2BU. The printed substrate may be buffered in the second buffer unit until the control electronics CE determine whether or not the substrate can be processed further. In case that the control electronics determines that the substrate is approved for further processing, the buffered substrate may be discharged from the inkjet system to a discharge station DS. Alternatively, the buffered substrate may be returned and re-entered into the printing area PA to print a back-side of the substrate. The discharge station DS may be an etch station which may include a discharge conveyor. In case that the control electronics determines a disapproval of a substrate, the substrate may be ejected to a bin. The first and/or second buffer unit may comprise a bin B for collecting disapproved substrates from the stream of substrates. Collected disapproved substrates may be recycled to obtain blank substrates.

To determine an approval or disapproval of printed substrates, the control electronics CE are configured to carry out a quality inspection Q as explained by FIG. 1A and FIG. 1B. The quality inspection is carried out by the control electronics of the inkjet system. The control electronics CE are configured to digitally receive a pattern layout. The pattern layout defines a desired layout of an ink pattern to be printed on a surface of a substrate S. The control electronics convert the pattern layout to an input image. The input image defines dot positions of the ink pattern to be printed. The control electronics further receive a scan image from the scanning unit SU. The control electronics are configured to compare a received scan image with the input image. The comparison of the scan and input image results in an approval or rejection of a printed substrate. After carrying out the quality inspection, the control electronics generate an output signal for further processing the substrate.

Beside the illustrated embodiments, several variants are possible which lie within the scope of protection defined by the appended claims. Instead of printing circuit boards, the printing process can be carried out to manufacture other electronic substrates e.g. display panels.

It is remarked that measures according to the invention and in particular mentioned in the dependent claims can be patentable as such and are considered patentable as such.

The FIGS. 3-5 relate in particular to the second aspect of the invention.

FIG. 3 relate in particular to the second, third and fourth aspect according to the invention.

FIG. 3 depicts an inkjet system IS according to an embodiment of the invention for depositing ink fluid in a desired pattern on a substrate S by jetting liquid droplets DR of the ink fluid in a jetting direction JD towards the substrate S. The inkjet system is preferably a drop-on-demand inkjet system in which a droplet is only jetted when required. This is in contrast to continuous inkjet systems in which droplets are continuously jetted at a predetermined frequency and wherein droplets required to form the pattern are directed towards the substrate and the remaining droplets are captured and thus prevented from reaching the substrate.

The inkjet system of FIG. 3 is an industrial inkjet system, for instance an inkjet system used to deposit resist material as a mask layer on a printed circuit board (PCB) as an alternative to the more traditional process of providing a mask layer using lithography. Because the mask layer can be deposited directly by the inkjet system, the amount of process steps can be reduced dramatically and thus the time for PCB manufacturing. However, such an application requires a high droplet placement accuracy and a high reliability (substantially every droplet counts).

To provide a high accuracy inkjet system, the inkjet system IS comprises a force frame FF which supports a metrology frame MF from the ground GR. Between the force frame FF and the metrology frame MF a vibration isolation system VIS is provided to support the metrology frame MF from the force frame FF while isolating the metrology frame MF from vibrations in the force frame FF. As a result, a relatively steady and quiet printing environment can be created on the metrology frame MF which is advantageous for accuracy.

The inkjet system further comprises a print head assembly with one or more print heads PH which are held by a print head holder H, and a substrate holder SH to hold the substrate S. The print heads PH each comprise one or more, typically dozens of, nozzles from which droplets DR can be ejected towards the substrate S. The nozzles are preferably arranged in an array, i.e. in one or more rows. The print heads together define a printing plane perpendicular to the jetting direction JD, said printing plane indicating where the substrate has to be positioned in order to receive jetted droplets from the print heads.

The substrate holder SH is moveable relative to the print heads PH in a printing direction PD parallel to the Y-direction and thus parallel to the printing plane in order to let a substrate S pass below the print head assembly. In this application a distinction is made between passing the print head assembly while moving from left to right in FIG. 3, i.e. moving the substrate holder in the positive Y-direction, and passing the print head assembly while moving from right to left, i.e. moving the substrate holder in the negative Y-direction. The right to left movement will be referred to as a forward swath and the left to right movement will be referred to as a backward swath.

In order to be able to cover the entire top surface TS of the substrate S, many configurations are possible. In a first configuration, the printing plane in the X-direction is at least as large as the largest possible dimension in X-direction of a substrate S that can be held by the substrate holder SH. In that case, a single swath of the substrate holder SH may suffice to cover the entire top surface with droplets. In a second configuration, the printing plane in X-direction is smaller than the largest possible dimension in X-direction of a substrate S that can be held by the substrate holder SH. In that case, multiple parallel swaths are necessary to cover the entire top surface TS of the substrate S. To allow multiple parallel swaths, the print head assembly and/or the substrate holder SH is moveable in the X-direction perpendicular to the printing direction PD.

In case of the printing plane in the X-direction being at least as large as the largest possible dimension in X-direction of a substrate S that can be held by the substrate holder SH, multiple swaths may still be necessary in order to obtain the required printing resolution, because the nozzles in the print heads PH may be arranged at a larger distance than the corresponding pitch from each other, e.g. to prevent or reduce cross talk between adjacent nozzles. The substrate is then passing the print head assembly multiple times, wherein each time the substrate has been moved in X-direction corresponding to the resolution in order to print the entire pattern.

In this embodiment, the print head assembly has a printing plane with a dimension in X-direction at least as large as the largest possible dimension in X-direction of a substrate the substrate holder SH can handle. As a result, the print head assembly can be mounted stationary with respect to the metrology frame MF.

In the embodiment of FIG. 3, the substrate holder SH is supported by a substrate positioning stage PS, which substrate positioning stage PS in turn is supported by the metrology frame MF. The substrate positioning stage PS is supported by the metrology frame such that it is moveable in the printing direction PD, thereby allowing to position the substrate holder SH and thus the substrate S in the Y-direction. Positioning of the substrate positioning stage PS is done using a stage positioning device SD, which is able to apply forces F between the substrate positioning stage PS and the force frame FF. As a result, the forces F do not introduce disturbances to the metrology frame MF, but are transmitted to the ground via the force frame FF, which results in a higher obtainable accuracy of the inkjet system.

Between the substrate positioning stage PS and the substrate holder SH, a holder positioning device HD is provided in order to position the substrate holder SH in one or more degrees of freedom, preferably at least in the printing direction PD, relative to the substrate positioning stage PS. Using this configuration, the stage positioning device SD can be used for coarse positioning the substrate holder SH in the printing direction while the holder positioning device HD can be used for fine positioning of the substrate holder in the printing direction relative to the print head assembly. If required, the holder positioning device HD may also be used for fine positioning of the substrate holder in other directions as well, e.g. the X-direction and/or the Z-direction, and may even fine position the substrate holder in rotational directions such as Rx, Ry and Rz as well. Preferably, the holder positioning device HD is able to position the substrate holder relative to the substrate positioning stage in six degrees of freedom.

Position information about the substrate holder SH relative to the metrology frame MF is measured by a measurement system MS. The measurement system is at least configured to measure a position quantity, i.e. actual position, velocity or acceleration, of the substrate holder in the printing direction PD. In an embodiment, the measurement system measures position information about the substrate holder in six degrees of freedom, depending on the level of control that is applied/required.

The output of the measurement system MS is provided to control electronics CE. The control electronics are here depicted as a black box that controls all processes in the inkjet system IS. As an example, the output of the measurement system MS can be used by the control electronics to drive the stage positioning device SD and the holder positioning device HD (as shown in dashed lines) in order to position the substrate holder accurately relative to the print head assembly. The control electronics may further send driving signals to the print heads PH (see dashed lines) in order to print a desired pattern on the substrate while the substrate S passes the print heads PH.

The inkjet system IS further comprises a droplet detection device DD which measures the position of placed droplets on the substrate, e.g. by emitting light towards the substrate and detecting the reflected light. The obtained information is also send to the control electronics, which may comprise a calibration unit in order to adjust the position of the print heads relative to each other based on the droplet position information obtained by the droplet detection device. The droplet detection device DD may further be used to calibrate the timing for firing the nozzles.

A more detailed explanation of parts of the inkjet system IS can be found below with reference to the respective drawings.

FIG. 4 depicts schematically a print head assembly with six print heads 1, 3, 5, 7, 9, 11 as seen from below. The shown print head assembly may be part of the inkjet system IS shown in relation to FIG. 3.

In this embodiment, all print heads are identical. Each print head comprises in this embodiment twelve nozzles NO (see for reference numeral print head 7) arranged in two rows of six nozzles. The nozzles are only shown with respect to the upper print heads 1, 7 for simplicity reasons. The print heads are grouped in groups of three print heads, namely print heads 1, 3, 5 and print heads 7, 9, 11, wherein each group comprises a primary print head 1, 7, an associated secondary print head 3, 9, and an associated tertiary print head 5, 11.

Each nozzle has a virtual printing line on the substrate on which ink fluid droplets can be deposited when the substrate moves relative to the print head assembly in the printing direction PD only. The printing line PL1 for nozzle NO1 of the primary print head 1 is depicted in FIG. 4.

The secondary and tertiary print heads are arranged at a distance from the associated primary print heads in the printing direction. Due to the print heads being identical in terms of amount of nozzles and nozzle positions, each nozzle of the primary print head has a corresponding nozzle at the secondary and tertiary print head. For nozzle NO1 of the primary print head, these corresponding nozzles NO2 and NO3 are shown in FIG. 4.

The primary, secondary and tertiary print heads are further arranged such that the respective virtual printing lines PL2, PL3 of the nozzles NO2 and NO3 are lying at the same position as the printing line PL1 of the nozzle NO1.

The rows of nozzles NO of each print head are positioned non-perpendicular to the printing direction, i.e. the rows have a non-zero angle $\alpha$ with a direction perpendicular to the printing direction PD. As a result, the distance $\Delta x$ between virtual printing lines of other nozzles can be very small which means that the resolution can be high, while the distance D between the nozzles can be larger to minimize cross talk between neighboring nozzles without requiring additional print heads as is done in prior art systems.

Because in this embodiment three nozzles are positioned on the same virtual printing line, they can advantageously be used to increase the reliability of the system.

In an embodiment, a printing performance measuring unit may be provided to measure the printing performance of a nozzle, e.g. by looking at the acoustics of an actuation chamber connected to the nozzle which may provide information about the presence of air bubbles in the actuation chamber, clogging of the nozzles, etc.

Such a printing performance measuring unit may measure printing performance of each nozzle on a regular basis. The printing performance of a nozzle can then be compared with the printing performance of corresponding nozzles within the group. Subsequently, the nozzle having the best printing performance may be used to print until another nozzle is measured to have the best printing performance and is used for printing. In this way, the nozzle with the best characteristics is always used to print, which increases the reliability and the accuracy of the inkjet system.

The printing performance measuring unit may also be able to predict future printing performance. This allows for the following method:

During a backward swath BS of the substrate holder, the substrate will first pass the primary print heads, then the secondary print heads and finally the tertiary print heads. In an embodiment, the primary and secondary print heads may be used for printing in an alternate fashion, in which e.g. each print head prints for 10 ms. When one of the primary or secondary print heads is not printing, the printing performance measuring unit may be used to measure the printing performance and to derive therefrom the future printing performance. If the printing performance measuring unit for instance predicts that nozzle NO1 will behave unsatisfactory within a certain amount of time, printing with nozzle NO1 may be stopped and continued with nozzle NO3 of the tertiary print head, so that alternatingly nozzle NO2 and NO3 are used for printing.

When the substrate holder makes a forward swath FS, the printing order may be reversed, so that in a normal situation the tertiary and secondary print head alternatingly print and the primary print head is used as a back-up print head in case of an upcoming nozzle failure.

In case two corresponding nozzles fail or behave unsatisfactory, the third corresponding nozzle can still be used for printing, although the risk for errors increases, also because this nozzle continuously has to print. A warning signal is then preferably communicated to e.g. maintenance personnel.

FIG. 5 depicts schematically a portion of a print head positioning device for positioning a print head in the inkjet system IS of FIG. 1 relative to a print head holder. The print head positioning device comprises a base member, which in this embodiment comprises two parts BM1 and BM2, to be releasably mounted to the print head holder.

Connected to the base member is a body BO with an opening OP for receiving a print head, such that the body is able to support the print head. The body is moveable with respect to the base member parts BM1, BM2 by the use of elastic hinges H1, H2, H3 and H4 in a translational direction TD and a rotational direction RD.

The print head positioning device may further comprise actuators to position the body relative to the base member. The actuators are schematically shown by the forces F1 and F2 they can apply. The shown forces F1 and F2 have an opposite direction, which would result in a rotation of the body. By applying forces in the same direction a translation of the body can be performed. The actuators may for instance be stepper motors.

Connections between print head holder and print head are preferably provided at the base member so that further transport of power, data, pressure, etc can be done from the base member to the print head. As a result, placement of a unit formed by a print head and a print head positioning device can be done in an easy plug and play manner without having to worry about the position accuracy.

The FIGS. 3, 6-8 relate in particular to the third aspect of the invention.

In particular with respect to the third aspect of the invention, the inkjet system as shown in FIG. 3 further comprises an ink dosing system for dosing ink to the multiple print heads of the inkjet system. In the embodiment of FIG. 3, the ink used is hot-melt ink, which has the property that it is a solid material at room temperature and thus needs to be heated to an elevated temperature to become liquid and therefore jettable. The ink dosing system is thus a hot-melt ink dosing system and is not shown in FIG. 3 for simplicity reasons, but schematically in FIG. 6 instead. To show the connections to the multiple print heads, some print heads PH are shown in FIG. 6 as well.

FIG. 6 depicts schematically a hot-melt ink dosing system 1 for dosing a hot-melt ink to multiple print heads PH according to an embodiment of the invention. The hot-melt ink dosing system 1 of FIG. 6 is suitable to be used in the inkjet system according to FIG. 3.

The dosing system 1 comprises a closed circuit including a fluid line 3, and arranged in the fluid line a reservoir 5 and a pump 7. The reservoir 5 is configured to hold hot-melt ink, and the pump 7 is configured to circulate hot-melt ink in the closed circuit in a direction indicated by arrow 9.

Hot-melt ink has the property that it needs to be heated to an elevated temperature in order to be able to flow through the closed circuit. The dosing system therefore comprises a heating system configured to heat the hot-melt ink to a predetermined operating temperature allowing the hot-melt ink to flow in the closed circuit. In this embodiment, the heating system comprises a set of heating elements 11 which are able to supply heat to the fluid line and the reservoir. The heating elements 11 are shown as individual blocks for simplicity reasons, but may in practice be multiple heating elements distributed along the closed circuit. A heating element may for instance also be integrated into the pump 7.

The dosing system further comprises a fluid connection 13 per print head PH, which fluid connection is in fluid communication with the fluid line 3 of the closed circuit to drain hot-melt ink from the closed circuit to the print head PH. To control the amount of hot-melt ink to the print head PH, a dosing valve 15 is provided in each fluid connection.

Due to the fact that the hot-melt ink is circulated in the closed circuit, as many print heads can be connected to the closed circuit without significantly influencing the reliability of the dosing system. The size of the dosing system can be adapted to the consumption rate of the set of print heads connected to the dosing system and the corresponding replenishing rate that is desired.

For instance, the volume of hot-melt ink in the dosing system 1 for about sixty print heads PH may be in the order of 2 liters. This has the advantage that the residence time in the closed circuit is limited and the chance of the hot-melt ink changing properties due to aging is reduced. The small volume also has the advantage that the start-up time, i.e. the time it takes to heat the volume of hot-melt ink in the closed circuit to the predetermined operating temperature is reduced with respect to prior art dosing systems. Further, the circulation of the hot-melt ink has the advantage that the predetermined operating temperature of the hot-melt ink can be easily maintained, as a disturbance, e.g. a thermal disturbance, at a specific location in the closed circuit is in principle averaged over the entire closed circuit by the circulation and can easily be compensated at another location in the closed circuit. This is also advantageous from reliability point of view.

To measure the amount of hot-melt ink in the closed circuit, the reservoir comprises a level sensor 17. It may be desirable that the amount of hot-melt ink in the closed circuit is above a predetermined minimum level so that it can be ensured that enough hot-melt ink is available for the print heads. The level sensor is therefore preferably configured to detect whether the level of hot-melt ink is below or above a predetermined minimum level.

The level sensor 17 of FIG. 6 comprises a tubular measuring chamber 19 having an open end 21 at the bottom of the tubular measuring chamber 19 which can be closed off by the hot-melt ink if the level of the hot-melt ink in the reservoir is above the height at which the open end 21 is situated. The measuring chamber 19 is connected to an air-volume displacing device 23 which is configured to supply a predetermined volume of air into the measuring chamber 19. In this embodiment, the air-volume displacing device 23 is a moveable piston 25 in a cylinder 27. By moving the piston 25 up and down in the cylinder 27, air is moved in and out of the measuring chamber 19.

The level sensor further comprises a pressure sensor 29 to measure a pressure difference between the air-pressure in the measuring chamber 19 and an air-pressure in the reservoir above the hot-melt ink. In this embodiment, the pressure sensor 29 is connected to the reservoir via a tubular member 31 extending in the reservoir, said tubular member 31 being in fluid communication with the inside of the reservoir via an open end 33.

In the reservoir, three possible levels of the hot-melt ink are shown, namely a low level 35, a high level 37 and an intermediate level 39. When the level of the hot-melt ink in the reservoir is for instance at the low level 35, the measuring chamber 19 is in fluid communication with the tubular member 31, so that supplying air to the measuring chamber 19 using the air-volume displacing device 23 will not result in a pressure difference between the air-pressure in the measuring chamber 19 and the air-pressure in the tubular member 31. When the level rises to above the open end 21 of the measuring chamber 19, e.g. to the intermediate level 39 or the high level 37, the measuring chamber 19 is closed off by the hot-melt ink and is no longer in fluid communication with the tubular member 31. If air is now introduced into the measuring chamber 19, the air-pressure inside the measuring chamber 19 will increase relative to the air-pressure inside the tubular member 31. Hence, an air-pressure difference in favour of the air-pressure in the measuring chamber 19 indicates whether the level of the hot-melt ink in the reservoir is below or above the level corresponding to the height at which the open end 21 of the measuring chamber 19 is situated.

By moving the piston 25 up and down at regular intervals, the level inside the reservoir can also be measured at regular intervals. Other alternatives for the air-volume displacing devices are also envisaged.

The level sensor of FIG. 6 further comprises a tubular measuring chamber 41 having an open end 43 at the bottom of the tubular measuring chamber 41 which can be closed off by the hot-melt ink if the level of the hot-melt ink in the reservoir is above the height at which the open end 43 is situated. The measuring chamber 41 is connected to an air-volume displacing device 45 which is configured to supply a predetermined volume of air into the measuring chamber 41. In this embodiment, like the air-volume displacing device 23, the air-volume displacing device 45 is a moveable piston 47 in a cylinder 49. By moving the piston 47 up and down in the cylinder 49, air is moved in and out of the measuring chamber 41.

The level sensor further comprises a pressure sensor 51 to measure a pressure difference between the air-pressure in the measuring chamber 41 and the air-pressure in the reservoir above the hot-melt ink, in this embodiment implemented via a connection between the pressure sensor 51 and the tubular member 31. When the level of hot-melt ink inside the reservoir is below the open end 43, e.g. at the intermediate level 39 or the low level 35, supplying air to the measuring chamber 41 using the air-volume displacing device 45 will not result in a pressure difference between the air-pressure in the measuring chamber 41 and the air-pressure in the tubular member 31. When the level rises to above the open end 43 of the measuring chamber 41, e.g. to the high level 37, the measuring chamber 41 is closed off by the hot-melt ink and is no longer in fluid communication with the tubular member 31. If air is now introduced into the measuring chamber 41, the air-pressure inside the measuring chamber 41 will increase relative to the air-pressure inside the tubular member 31. Hence, an air-pressure difference in favor of the air-pressure in the measuring chamber 41 indicates whether the level of the hot-melt ink in the reservoir is below or above the level corresponding to the height at which the open end 43 of the measuring chamber 41 is situated.

By moving the piston 47 up and down at regular intervals, the level inside the reservoir can also be measured at regular intervals. Other alternatives for the air-volume displacing devices are also envisaged.

The measuring chamber 19 can thus be used to indicate a low level inside the reservoir and the measuring chamber 41 can be used to indicate a high level inside the reservoir, so that a control system is able to keep the level of hot-melt ink in the reservoir substantially between these two levels so that it is ensured that enough hot-melt ink is available to the print heads PH while the amount of hot-melt ink is kept below a predetermined maximum value to avoid hot-melt ink unnecessarily being subjected to a thermal load, thereby reducing the chance of aging.

Connectable to the reservoir is a hot-melt ink cartridge 53. The hot-melt ink cartridge 53 is in FIG. 6 shown in a connected state, but can be disconnected when necessary so that an empty hot-melt ink cartridge can be replaced by a filled hot-melt ink cartridge.

The hot-melt ink cartridge comprises solid hot-melt ink 54 in a filled state. The heating system of the dosing system comprises a heating element 55, which is able, when the cartridge is connected to the reservoir, to apply heat to the cartridge to melt the hot-melt ink which allows the hot-melt ink to flow into the reservoir to replenish the hot-melt ink in the closed circuit.

In this embodiment, the hot-melt ink cartridge allows to melt hot-melt ink only when required by the dosing system. Hence, when the level in the reservoir drops below the predetermined minimum level set by measuring chamber 19, the heating element 55 may be operated to melt hot-melt ink in the cartridge until the level has increased sufficiently. Replenishing the reservoir may be done until the level set by measuring chamber 41 is reached, but the size of cartridge may also be such that an intermediate level is obtained when emptying the cartridge, such that the maximum level may only be present for safety reasons or can be omitted.

The reservoir in the embodiment of FIG. 6 comprises a siphon 57 to which the cartridge is connectable. When the cartridge is removed from the reservoir, the siphon ensures that there is a gas separation between the inside of the reservoir and the environment, which provides a safe working situation. The heating system may further comprise a heating element 59 in order to melt solidified hot-melt in the siphon when necessary.

The cartridge, when connected to the reservoir comprises a bottom opening 58 through which melted ink is able to flow to the siphon 57. Due to the fact that hot-melt ink is present inside the ink cartridge in the solid and liquid phase there is a high chance of vacuum formation inside the cartridge preventing ink to flow out of the cartridge if no measures are taken. In the embodiment of FIG. 6 this is prevented by providing a spacer 56 above the opening 58, wherein the spacer has a surface area at least as large as the opening to cover the opening entirely, and wherein the spacer is arranged inside the cartridge between the solid hot-melt 54 and the opening such that melted ink has to flow around the spacer to get to the opening.

FIG. 7 depicts a cross-sectional view of a reservoir 5 according to an embodiment of the invention. The cross-section of the reservoir has a U-shape and therefore provides a large surface-area-to-volume ratio to the reservoir 5. As a result, the maximum distance inside the reservoir to the nearest wall of the reservoir is limited, so that when heat is applied through the wall to the interior of the reservoir, the hot-melt ink is heated up relatively quickly. The advantage of the U-shape is that the overall dimensions of the reservoir are within certain limits.

FIG. 8 depicts a cross sectional view of a hot-melt ink cartridge 53 according to an embodiment of the invention. The cartridge is a container having at least an opening 58 which is connectable to a reservoir. The orientation of the cartridge is such that the opening faces downwards, so that ink is able to flow out of the cartridge due to gravity forces. When the cartridge is not connected to the reservoir, the opening may be closed by a removable closing member.

Inside the cartridge a spacer 56 is provided at a distance from the opening between the opening and the solid hot-melt ink. As a result, melted ink has to flow around the spacer towards the opening 58 as indicated by arrows AR. In order to correctly position the spacer inside the cartridge, the spacer may be provided with protrusions 56A which extend sideways from the spacer towards a side wall of the cartridge. Ink is then able to flow between the protrusions towards the opening. To keep the spacer at a distance from the opening, the spacer may comprise extensions 58B, which may be formed by ridges. The extensions 58B and the protrusions 56A may also be used as heat conductors, so that heat applied to the lower portion of the cartridge to melt the hot-melt ink is also conducted to the spacer via the extensions 58B and protrusions 58A.

The FIGS. 3,9-10B relate in particular to the fourth aspect of the invention.

The inkjet system IS as shown in FIG. 3 further comprises a maintenance unit MU (see FIG. 9) configured to remove ink fluid from the surfaces SU of the print heads PH in which the nozzles are arranged, because ink fluid may accumulate on said surface during printing which reduces the obtainable accuracy and reliability.

The surfaces SU of the print heads PH are shown with reference to FIG. 9 in which the print head assembly is shown from below. The printing direction PD is also indicated by the respective arrow to indicate the transport direction of the substrates for printing. Only a few print heads and a few surfaces SU are indicated by the respective reference numerals PH and SU for clarity reasons.

Also schematically shown in FIG. 9 are a wiper support frame WSF of the maintenance unit MU that can be moved between a non-operational position NOP as shown in FIG. 9 in which no maintenance can be performed on the print heads and a maintenance position MP (see dashed box) below the print heads in which the maintenance unit is able to perform maintenance actions on the print heads. For this purpose guides G1,G2 are provided along which the wiper support frame is able to move between the non-operational position and the maintenance position. Movement of the wiper support frame may be caused by a respective actuation system provided between the wiper support frame and the guides G1, G2.

The non-operational position of the wiper support frame is in this case adjacent the transport area of the substrates, i.e. the movability of the wiper support frame is in a direction D1 perpendicular to the printing direction PD, which has the advantage that the maintenance unit can be moved to a position in which the maintenance unit does not interfere with the printing activities, i.e. does not collide with passing substrates or substrate holders.

The maintenance unit MU further comprises multiple wipers with respective wiper moving devices to move the wipers in a direction D2 relative to the wiper support frame WSF. Direction D2 is in this embodiment parallel to the longitudinal direction of the surfaces SU of the print heads PH. The wipers and wiper moving devices are schematically indicates by dashed boxes W as they are operational at the other side of the wiper support frame, i.e. the side of the wiper support frame facing towards the surfaces of the print heads when being in the maintenance position MP.

This configuration allows the wiper support frame to be positioned in the direction D1 such that the wipers are aligned with the surfaces SU of a first column of print heads after which the wipers are subsequently moved by the wiper positioning devices along the surfaces of the print heads. After performing the wiping action, the wipers can subsequently be positioned properly with respect to a second column of print heads for a next wiping action, and so forth until all print heads of the print head assembly are wiped clean. In such a case, the wiper support frame is moved stepwise and the wiping action is performed by the wiper moving devices while the wiper support frame is kept stationary relative to the print head assembly. It will be apparent to the person skilled in the art of maintenance units for inkjet systems that other configurations for moving the wiper are also envisaged.

So far, the maintenance unit can be according to the first or second subaspect of fourth aspect of the invention. An example of a maintenance unit according to the first subaspect of the fourth aspect of the invention will be given with reference to FIG. 10A, and an example of a maintenance unit according to the second subaspect of the invention will be given with reference to FIG. 10B.

FIG. 10A schematically depicts a part of a maintenance unit MU according to an embodiment of the first subaspect of the invention, which maintenance unit can be used in the inkjet system of FIGS. 3 and 9. Shown are a wiper support frame WSF which moveably supports a frame FR. In between the frame FR and the wiper support frame WSF, a wiper moving device WMD is operable to generate a force F1 to position the frame FR relative to the wiper support frame WSF.

Arranged on the frame FR is a wiper W1 to be moved along the surfaces of the print heads. Movement of the wiper W1 is guided by a guide with two parallel leaf springs LF which together form a linear guide allowing the wiper only to move up and down. Connected to the wiper W1 is a permanent magnet PM as part of a force actuator. The permanent magnet is arranged inside a coil CO being another part of the force actuator, so that supplying a current I to the coil by an appropriate energy source, e.g. a current source, will generate a force on the permanent magnet due to the interaction between the respective magnetic fields of the magnet and coil. This force can be used to position the wiper in a direction perpendicular to a surface SU of a print head PH with respect to the surface SU of the print head PH, which print head is shown in dashed lines.

The position of the wiper W1 relative to the surface SU is indirectly measured using a position sensor PS based on the assumption that the distance between frame FR and surface SU is substantially the same each time. The output of the position sensor is fed to a controller CON which based on the output of the position sensor provides driving signals to a current source CS to apply a current I to the force actuator, and to the wiper moving device WMD. In order to provide a predetermined wiping force to the surface SU, the maintenance unit comprises a set point generator SG which provides a set point corresponding to a location of the wiper W1 inside the print head PH as shown by wiper W1'. However, the wiper W1 is not able to reach that location, so that the controller will continuously urge the wiper W1 to the position W1' using the force actuator. The controller comprises a limiter LI which keeps the maximum applicable force applied by the force actuator within a predetermine value, in this embodiment by limiting the maximum current that can be generated by the current source. As a result, substantially the same wiping force is applied to the wiper independent of occurring variations in properties of the wiper.

FIG. 10B schematically depicts a part of a maintenance unit MU according to an embodiment of the second sub-aspect of the fourth aspect of the invention, which maintenance unit can be used in the inkjet system of FIGS. 3 and 9. Shown are a wiper support frame WSF which moveably supports a frame FR. In between the frame FR and the wiper support frame WSF, a wiper moving device WMD is operable to generate a force F1 to position the frame FR relative to the wiper support frame WSF.

Arranged on the frame FR is a wiper W1 to be moved along the surfaces of the print heads. Movement of the wiper W1 is guided by a guide with two parallel leaf springs LF which together form a linear guide allowing the wiper only to move up and down. Connected to the wiper W1 is a permanent magnet PM as part of a force actuator. The permanent magnet is arranged inside a coil CO being another part of the force actuator, so that supplying a current I to the coil by an appropriate energy source, e.g. a current source, will generate a force on the permanent magnet due to the interaction between magnet and coil. This force can be used to press the wiper against the surface of the print heads during a wiping action.

Preferably, the force actuator is configured such that a substantially constant current-force relationship is obtained in the working range of the wiper. This allows an open loop kind of control, wherein controlling the current through the coil properly controls the force applied to the wiper by the force actuator. The current can be measured using a measurement resistance R1 and measuring the voltage V1 over the resistance R1. The measured current can be supplied to a controller CON, which is able to control the current source CS based on said measured current.

In case the leaf springs of the guide do not apply a significant force to the wiper while guiding the wiper in the working range of the wiper, the force applied by the force actuator corresponds to the wiper force with which the wiper will be pressed against the surface of the print heads independent of the stiffness of the wiper, the actual position of the wiper etc. In some embodiment, it may be necessary to overcome a known or determinable constant force, e.g. gravity, but this constant force can easily be compensated for.

In case the forces applied by the guide to the wiper are significant and non-constant or when the current-force relationship is not constant, the mentioned open-loop control may not suffice. Usually, the current-force relationship is dependent on the position of the permanent magnet inside the coil, so that adding a position sensor PS for determining the position of the magnet can be beneficial for accurately determining the force applied to the wiper by the force actuator.

The position sensor PS can alternatively or additionally be used to determine the position of the guide. In case the stiffness of the leaf springs in vertical direction is too high, the disturbance force applied by the guide to the wiper is also dependent on the position of the wiper relative to the guide. Hence, measuring the position allows to determine the disturbance force of the guide which when fed to the controller can be compensated for.

The FIGS. 11-17 relate in particular to the fifth aspect of the invention.

FIG. 11a shows a flow chart of the method according to the invention. In the method a pattern layout L is received by control electronics of an inkjet system. The control electronics comprise a software to convert the pattern layout to an ink pattern. The software includes logic 1 to convert the received pattern layout L into a separate contour layer including at least one contour part and a separate inner region layer including at least an inner region part of the pattern layout. The logic 1 provides output data which is used to control at least one print head of the inkjet system. The logic 1 provides a first 1 and second 2 output data. The first output data 1 comprises contour data for printing a contour as defined in the contour layer. The second output data 2 comprises inner region data for printing an inner region as defined in the inner region layer. A contour of a pattern layout is defined by an outer border region of the pattern layout. An inner region is defined by a region which is enclosed by at least two border regions. A contour forms a border for an inner region. The first and second output data are subsequently processed to print the ink pattern. In a first step the contour data is processed to print the contour. The contour C is printed by deposing contour droplets onto a substrate. In a second following step, the inner region data is processed to print the inner region within a printed contour. The inner region F is printed by depositing fill-in droplets onto the substrate. After printing both the contour C and the inner region F, the final ink pattern P is obtained.

FIG. 11b illustrates a processing of an exemplary pattern layout in a flow chart as shown in FIG. 11a. The pattern layout is a typical integrated circuit (IC) pattern layout and includes a circuit line and a circular end portion. The circular end portion of the IC pattern layout can be used to connect an electrical component to build a printed circuit board (PCB). In the method according to the invention, the IC pattern layout P is separated into a contour layer and an inner region layer. Logic 1 is applied to the IC pattern layout and contour data 1 is generated which is first processed to print the contour C on a substrate. An obtained contour C is depicted in a subsequent box in the flow chart of FIG. 11b. The contour C is an outline of the pattern layout. Logic 1 is further applied to generate inner region data 2. The inner region data 2 is processed to print an inner region F on the substrate. The inner region F may be printed by printing at least one swath of fill-in droplets inside the already printed contour. The inner region F can be defined as the pattern layout in which an outer edge which defines the contour is subtracted. The outer edge may have a width of at least one contour droplets. Preferably, the outer edge has a width of one contour droplet.

The control electronics comprise a contour print algorithm to print the contour C to a substrate. The contour print algorithm converts the contour C to a set of droplet positions.

The contour print algorithm is e.g. a rasterizing algorithm, wherein the contour data is projected onto a raster to obtain a distribution for contour droplets. The raster may have a plurality of raster cells in which the contour algorithm may generate a droplet position for each raster cell which is covered for a certain amount.

Preferably, the contour print algorithm is based on an orientation of at least a part of the contour. The orientation of the at least part of the contour is measured relative to a reference axis. The orientation may be defined by an angle with respect to the reference axis. In a step of the orientation based contour print algorithm, the at least part of the contour is classified in dependence of the defined orientation. The at least part of the contour is classified in a class of a classification system. Each class has its own conversion to obtain a set of positions of the contour droplets. In dependence of the orientation of the at least part of the contour, the conversion of contour the differs. Herewith, an optimal compensation for an interaction mechanism between adjacent droplets can be achieved. The contour droplets are printed by applying the class dependent selected contour print algorithm.

In FIG. 12 a classification system is depicted in a Cartesian system. The Cartesian system has a first quadrant which is delimited by an X-axis and an Y-axis. The classification system has three classes, a first class I, a second class II, and a third class III.

A first class I is defined for a group of contour parts which have an orientation in a direction of the X-axis and in a direction under an angle larger than a predetermined angle $\alpha$. The predetermined angle $\alpha$ is an angle in the first quadrant with respect to the Y-axis. The predetermined angle $\alpha$ may be a parameter which may be a function of ink flow and/or substrate properties.

A second class II is defined for a group of contour parts which has an orientation in a direction under an angle smaller or equal to the predetermined angle $\alpha$.

A third class III is defined for a group of contour parts which has an orientation in a direction of the Y-axis.

In the method according to the invention, the Cartesian system is projected onto a layout of the inkjet system. The inkjet system has a layout which includes a printing direction which corresponds with a travel direction of the substrate. The Y-axis is projected onto the printing direction of the inkjet system.

In the method according to the invention all separated contour parts are classified into one of the three classes. Contour parts having an orientation falling outside the first quadrant and in one of the second, third, or fourth quadrant of the Cartesian system are in a preparing step first mirrored to obtain an orientation falling in the first quadrant. In a subsequent step, the set of droplet positions is determined, wherein the mirroring step is compensated again to obtain a set of droplet positions in the corresponding quadrant.

The FIGS. 13a-13d show several examples of orientations of contours in several directions. The contours may be combined as contour parts to obtain a complete contour as defined by a pattern layout. The figures show an X-axis and an Y-axis of a Cartesian system. An ink pattern is illustrated which has a contour C and an inner region F. The ink pattern is obtained by depositing contour and fill-in droplets in a printing process. The printing direction is in parallel with an Y-axis. The contour C is deposited first and formed by an array of contour droplets. The array of contour droplets form a strip element. The inner region F is formed by filling in a region in between the two opposite contours C by depositing fill-in droplets. The fill-in droplets are deposited in swaths. FIG. 13a-13d show a bold line C' at the contour C which indicates a resulting pattern layout edge which borders the ink pattern after spreading out.

Figure 13A:
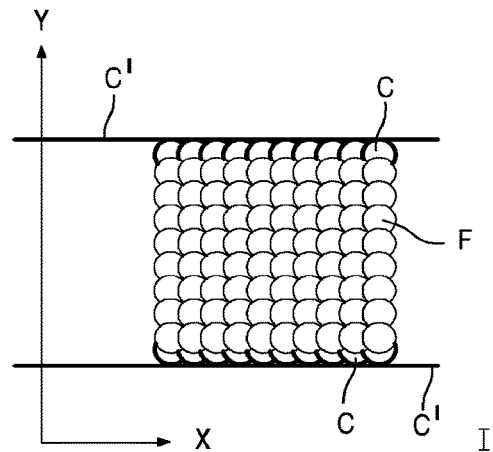

FIG. 13a shows an orientation of a contour in a first class I. The orientation of the contour is in a X-direction. The contour is formed by a deposition of contour droplets. The contour droplets are positioned in a line and have a constant Y-coordinate. The contour droplets form a strip element. The strip element is built with contour droplets of a constant size. The strip element is built with a single array of contour droplets. The strip element has a constant pitch. The mutual distance between two successive contour droplets in the strip element is constant.

Figure 13B:
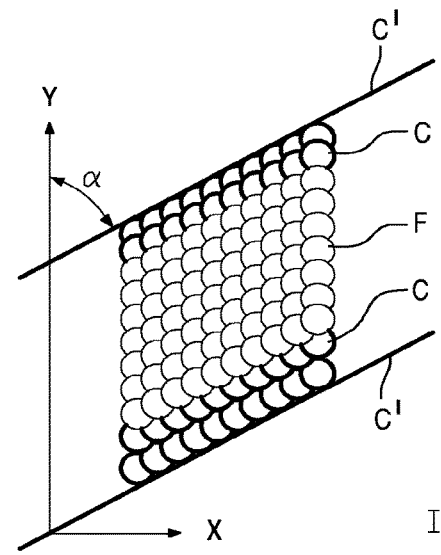

FIG. 13b shows another orientation of a contour in a first class I, wherein the orientation is under an angle with respect to the Y-axis which is larger than or equal to the predefined angle $\alpha$. The contour is formed by a deposition of contour droplets. The contour droplets are positioned in a line. The contour droplets form a strip element. The strip element is built with a double array of contour droplets. The strip element is built with contour droplets of a constant size. The strip element has a constant pitch. The mutual distance between two successive contour droplets in the strip element is constant.

Figure 13C:
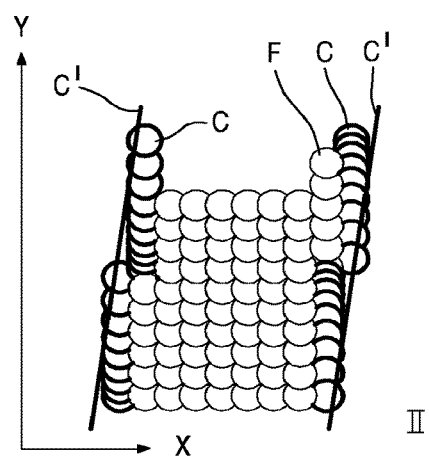

FIG. 13c shows an orientation of a contour in a second class II. The orientation of the contour is in a direction under an angle with respect to the Y-axis which is smaller than the predefined angle $\alpha$ as depicted in FIG. 13b. The contour is formed by a deposition of contour droplets. The contour droplets form a strip element. The strip element is built with a single outer array of contour droplets. The strip element has a varying pitch in between the droplets. The mutual distance between two successive contour droplets in the strip element is linearly increasing in the Y-direction of the contour element. The mutual distance in between a pair of two neighboring droplets is a function of a position of the pair of droplets. The strip element is built with contour droplets of a constant size.

The strip element is built up with a sequence of strip partitions. The strip partitions extend in Y-direction. Each strip partition has a constant X-coordinate. Each strip partition has a fixed length of a fixed amount of droplets to obtain the strip with a linear extension in an inclined orientation. Adjacent strip partitions in X-direction are staggered positioned with a stagger pitch of a size of a droplet. Initially, in comparison with the resulting ink pattern, indicated with the bold line C', the initial outer edge has an edge gap at a cross over from a first swath in Y-direction to a second swath in Y-direction. After a flow out of the droplets, a resulting outer edge is obtained which is indicated by the bold line 'C'.

Figure 13D:
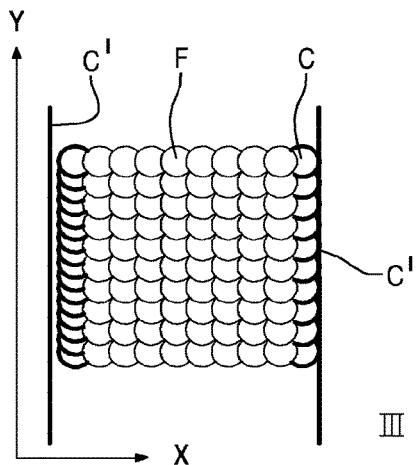

FIG. 13d shows an orientation of a contour in a third class III. The orientation of the contour is in a Y-direction. The contour is formed by a deposition of contour droplets. The contour droplets are positioned in a line and have a constant X-coordinate. The contour droplets form a strip element. The strip element is built with contour droplets of a constant size. The strip element is built with a single array of contour droplets. The strip element has a constant pitch. The mutual distance between two successive contour droplets in the strip element is constant.

FIG. 13d illustrates further an changing ink flow effect when the pitch of the strip element is adjusted. The bold line C' marks a resulting ink pattern outer edge. In the illustration, a smaller pitch in between droplets is applied at the left side in comparison with the right side. At the right side of the illustration the deposited droplets have hardly any ink flow at a predetermined time interval, the outer edge of the contour coincidences with the bold line C'. In contrast, the left side of the illustration shows relatively more ink flow in the time interval which has occurred by applying a small pitch. By applying the small pitch, an initial off set has occurred in which the outer edge of the contour lies away from the final obtained edge of a pattern layout as indicated by the bold line C'.

FIG. 14 shows a flow chart, wherein the contour print algorithm CPA is subdivided into a coverage algorithm CA and an ink flow algorithm IFA. The coverage algorithm CA is applied in a first step. The ink flow algorithm IFA is applied in a second step.

The pattern layout L is an input for the coverage algorithm CA. In the coverage algorithm at least a part of the contour, a contour part, of the pattern layout is converted into a set of coverage elements. The pattern layout is built up by the coverage elements. The coverage algorithm is applied to obtain an optimal coverage of the pattern layout by coverage elements. A set of coverage elements including their position is an output after applying the coverage algorithm to a pattern layout. In particular, the coverage element is a strip element. The strip element as a coverage element includes a length, an orientation and at least one absolute position of a droplet. The set of coverage elements can be printed in a subsequent step to obtain the ink pattern P.

The coverage algorithm may include several coverage parameters for defining a coverage element. A coverage parameter may be a droplet size, a number of droplets per coverage element, a function or value for a mutual distance between two adjacent droplets in a coverage element. The coverage parameters may vary in dependence of circumstances like e.g. ink and substrate material.

The ink flow algorithm converts the coverage elements into a set of absolute positions for the contour droplets to obtain the ink pattern, wherein a factor of ink flow behaviour is included. A coverage element is an input for the ink flow algorithm. A set of absolute positions of droplets is an output of the ink flow algorithm. In particular a bitmap may be generated which contains droplet positions for optimally printing the coverage elements. Control electronics are provided to translate the set of absolute positions of the ink pattern to control signals for the inkjet system, in particular for a print head and substrate positioning stage.

FIG. 15 shows a flow chart of the ink flow algorithm, wherein a set of coverage elements is converted to an ink pattern P.

The ink flow algorithm has ink flow parameters which are determined by using the inkjet system. The ink flow parameters are determined in several steps. In a first step 5.1, at least one test pattern is printed. Preferably, the test pattern is a coverage element or a set of coverage elements. In a second step 5.2, the at least one test pattern is scanned. The inkjet system has a scanning unit for scanning the test pattern. An image is captured of the test pattern by the scanning unit. The scanning unit is an internal scanning unit. The scanning unit is integrated in the inkjet system. In a third step 5.3, a test pattern is extracted. In a fourth step 5.4 at least one relevant parameter like a width is extracted from the test pattern. Herewith, measurement data is collected to establish an ink flow effect. In a fifth step 5.5, the ink flow parameters are determined. The measurement data can be compared with the pattern layout to determine any deficiencies. For instance, the width of a test pattern can be compared with an inputted pattern layout. If a width is too large for a combination of coverage elements, the contour print algorithm may be corrected. Herewith, the contour print algorithm may be self-teaching. Parameters relating to the ink flow effect are inputted in the ink flow algorithm to compensate for deficiencies. The deficiencies can be compensated in a next print. Preferably, the width W is the only dimension that needs to be measured by a test pattern.

FIG. 16a-c show in an exemplary illustration a test pattern comprising of a set of two coverage elements. A resulting width W0 or W1 which is indicated with a bold line and an arrow is obtained by applying a predetermined time interval Δt for applying a subsequent adjacent coverage element. The time interval is a delay time for depositing a subsequent neighboring coverage element. The coverage elements are strip elements which extend in Y-direction and which are disposed at a distance Δx from each other. A first coverage element is printed and after the predetermined time interval Δt a second coverage element is printed at the predetermined pitch Δx adjacent the first coverage element. The contour may be printed first by printing the first coverage element, whereafter the inner region is printed by printing the second coverage element. The first coverage element may be a contour part, the second coverage element may be an inner region part.

FIG. 16a shows a narrowing effect as an ink flow effect. The test pattern comprises two equal coverage elements s1. The combination of two s1 coverage elements results in a narrowing effect by applying a time interval Δt of 5 seconds. The measured width of the resulting ink pattern is W0 which is smaller than the desired width W1.

FIG. 16b shows the same combination of two coverage elements s1 as shown in FIG. 6a, but by applying a time interval Δt of 10 seconds. The width of the resulting ink pattern is now W1. The result of the ink flow effect in dependence of the time interval Δt can be stored in the control electronics of the ink jet system.

FIG. 16c shows an alternative combination of coverage elements to achieve an ink pattern with a width W1. A first coverage element s1 is combined with a second coverage element s2 by applying a time interval Δt of 5 seconds. In comparison with the combination of two coverage elements s1, this combination of s1 and s2 leads in a shorter time to the desired W1. In the first place, in the contour coverage algorithm, coverage elements are selected that best fit the desired contours. Furthermore, to obtain a shorter printing process, it may be preferred to apply the combination as shown in FIG. 16c instead of the combination as shown in FIG. 16b. The inkjet system may be self teaching by measuring test patterns and programmed to select subsequently a combination of coverage elements based on a reduction of a print process.

FIGS. 17a and 17b show a further exemplary illustration of two different combinations of test patterns.

In FIG. 17a a test pattern is printed by a combination of two coverage elements s1 and s0. The first coverage element s1 is formed by positioning six ink droplets in Y-direction at a certain mutual distance. The second coverage element s0 is formed by positioning five ink droplets in Y-direction at a larger mutual distance. A pitch in between the first and second element is 50 μm in X-direction. of A time interval of 10 seconds is applied before printing the second coverage element S0.

In FIG. 17b a test pattern is printed by a combination of two coverage elements s1 and s3. The first coverage element s1 is formed by positioning six ink droplets in Y-direction at a certain mutual distance. The second coverage element s3 is formed by positioning eight ink droplets in Y-direction at a smaller mutual distance. Now, a pitch in between the first and second element is 25 μm in X-direction and a time interval of 5 seconds is applied before printing the second coverage element s3. The combination of s1 and s3 has a narrowing effect as an ink flow effect. In comparison with the combination as shown in FIG. 17a, the combination of coverage elements s1 and s3 lead in a shorter printing time to the same result in width w2. The inkjet system may be programmed to select in this case a combination of s1 and s3 when a short printing time is preferred.

In a variant, the coverage and ink flow algorithm may also be applied to determine a position of the fill-in droplets to form the inner region.

It is remarked that aspects according to the invention and in particular mentioned in the clauses can be advantageous as such and are considered patentable as such. In particular, it may be advantageous to apply a coverage or ink flow algorithm in a printing algorithm before generating a set of droplet positions independent of whether contour droplets are printed prior to fill-in droplets.

Although the invention has been disclosed with reference to particular embodiments, from reading this description those of skilled in the art may appreciate a change or modification that may be possible from a technical point of view but which do not depart from the scope of the invention as described above and defined in the clauses with prefix 974. Modifications may be made to adapt a particular situation or material to the teachings of the invention without departing from the essential scope thereof. It will be understood by those of skilled in the art that various changes may be made and equivalents may be substituted for elements thereof without departing from the scope of the invention. Therefore, it is intended that the invention is not limited to the particular embodiments disclosed in the above detailed description, but that the invention will include all embodiments falling within the scope of the appended clauses with prefix 974.

Thus, the fifth aspect of the invention provides a method for printing a more accurate ink pattern. In particular, the invention provides a method to print an integrated circuit pattern. The method can be carried in a simple manner by applying the presented improvements to applied algorithms to converting a pattern layout to a set of droplet positions.

The FIGS. 3,18-22-x relate in particular to the sixth aspect of the invention.

FIG. 3 and FIG. 18 depict an inkjet system according to an embodiment of the sixth aspect of the invention. FIG. 3 and FIG. 18 depict an inkjet system IS according to an embodiment of the invention for depositing material in a desired ink pattern on a substrate S by jetting liquid droplets of the material towards the substrate. The material is in particular ink. The ink pattern has to be produced according to a pattern layout. The pattern layout is e.g. uploaded to the inkjet system as a bitmap. The inkjet system is preferably a drop-on-demand inkjet system in which a droplet is only jetted when required. This is in contrast to continuous inkjet systems in which droplets are continuously jetted at a predetermined frequency and wherein droplets required to form the pattern are directed towards the substrate and the remaining droplets are captured and thus prevented from reaching the substrate.

The inkjet system of FIG. 18 is an industrial inkjet system, in particular an IC inkjet system, for instance an inkjet system used to deposit resist material as a mask layer on a printed circuit board PCB as an alternative to the more traditional process of providing a mask layer using lithography. Because the mask layer can be deposited directly by the inkjet system, the amount of process steps can be reduced dramatically and thus the time for PCB manufacturing. However, such an application requires a high droplet placement accuracy and a high reliability (every droplet counts).

As depicted in FIG. 18, an orthogonal system including an X, Y and Z-axis can be projected onto the inkjet system. The Y-axis is a longitudinal axis. The Y-axis may be defined as a direction extending in a printing direction. The printing direction of the inkjet system is defined as a direction of movement of a substrate when passing a print head assembly to print a swath onto the substrate. The printing direction corresponds with a travel of the substrate positioning stage. The travel of the substrate positioning stage corresponds with a largest stroke of the substrate with respect to the printing assembly.

The X-axis may be defined as a direction perpendicular to the Y-axis. The X-axis extends in a direction transversal the printing direction. The X-axis is a lateral axis. The X-axis and Y-axis define a substantially horizontal plane in the inkjet system.

The Z-axis may be defined as a direction perpendicular to the X- and Y-axis. The Z-axis extends in upwards direction. The Z-axis is an up-down axis. The Z-axis extends in a substantially vertical direction.

A rotational direction about the X-axis Rx, a pitch motion, may be defined as a rotation of the substrate about the lateral axis.

A rotational direction about the Y-axis Ry, a roll motion, may be defined as a rotation of the substrate about a longitudinal axis. The longitudinal axis extends from a front to a back of the substrate.

A rotational direction about the Z-axis Rz, a yaw motion, may be defined as a rotation of the substrate about the up-down axis.

To provide a high accuracy inkjet system, the inkjet system IS comprises a force frame FF which supports a metrology frame MF from the ground GR. Between the force frame FF and the metrology frame MF a vibration isolation system VIS is provided to support the metrology frame MF from the force frame FF while isolating the metrology frame MF from vibrations in the force frame FF. As a result, a relatively steady and quiet printing environment can be created on the metrology frame which is advantageous for accuracy.

The inkjet system further comprises a print head holder H. Here, the print head holder H is stationary mounted in the inkjet system. The print head holder H is fixedly connected to the metrology frame MF. The print head holder H has a shape of a beam. The print head holder extends in an X-direction. The print head holder holds a print head assembly which comprises at least one print head PH. The print heads PH each comprise one or more, typically dozens of, nozzles from which droplets can be ejected towards the substrate S. The print head assembly defines a printing range in the X-direction in which droplets can be placed during a forward or backward swath, which defines a width of a printing area PA and a printing range in the Y-direction which defines a length of a printing area PA.

Further, the inkjet system comprises a substrate holder SH to hold a substrate S.

The substrate holder SH is moveable relative to the print head PH in a printing direction PD parallel to the Y-direction in order to let a substrate S pass below the print head assembly. In this application a distinction is made between passing the print head assembly while moving from left to right in FIG. 18, i.e. moving the substrate holder in the positive Y-direction, and passing the print head assembly while moving from right to left, i.e. moving the substrate holder in the negative Y-direction. The right to left movement will be referred to as a forwards swath and the left to right movement will be referred to as a backward swath.

In order to be able to cover an entire top surface TS of the substrate S, many configurations of the print head assembly are possible.

In a first configuration, the printing range in the X-direction is at least as large as the largest possible dimension in X-direction of a substrate S that can be held by the substrate holder SH. In that case, a single swath of the substrate holder SH may suffice to cover the entire top surface with droplets.

The print head of the print head assembly may comprise an array of print head nozzles which are equally spaced form each other in X-direction. A pitch between neighbouring nozzles may e.g. be about 100 µm. However, a pattern layout for an ink pattern may include tracks which are spaced at a distance smaller than the pitch in between the neighbouring nozzles. In such a case, the print head holder may move relative to a substrate in a direction transversal, in particular perpendicular, the printing direction, i.e. the X-axis, to allow a deposition of droplets at a region positioned in between the neighbouring nozzles. Hence, in this situation multiple passes of the substrate are necessary to comply to the design requirements of the pattern layout. Preferably, the relative movement of the printhead with respect of the substrate is obtained by moving the substrate in X-direction.

In a second configuration, the printing range in X-direction is smaller than the largest possible dimension in X-direction of a substrate S that can be held by the substrate holder SH. In that case, multiple parallel swaths are necessary to cover the entire top surface TS of the substrate S. To allow multiple parallel swaths, the print head assembly and/or the substrate holder SH is moveable in the X-direction perpendicular to the printing direction PD.

In this embodiment, the print head assembly has a printing range in X-direction at least as large as the largest possible dimension in X-direction of a substrate the substrate holder SH can handle. The print head assembly is mounted stationary with respect to the metrology frame MF.

In the embodiment of FIG. 18, which is further illustrated in FIG. 19, the substrate holder SH is supported by a substrate positioning stage PS. The substrate positioning stage PS is supported by the metrology frame MF. The substrate positioning stage PS is supported by the metrology frame such that it is moveable in the printing direction PD, thereby allowing to position the substrate holder SH and thus the substrate S in the Y-direction. Positioning of the substrate positioning stage is done using a stage positioning device SD. The stage positioning device comprises a stage guidance, a stage position measuring system and a stage actuator.

The stage guidance is a linear guidance. The stage guidance comprises a pair of bar elements to support and guide the substrate positioning stage. The substrate positioning stage is beared to the stage guidance by ball bearings. The stage guidance is connected to the metrology frame MF. Herewith, vibrations from the ground do not disturb a linear guidance of the substrate positioning stage.

The stage position measuring system comprises a linear encoder. The linear encoder includes an elongated ruler which extends in Y-direction which is mounted to the metrology frame and an optical reader which is mounted to the substrate positioning stage. In operation, the substrate positioning stage passes along the ruler to obtain an Y-position of the substrate positioning stage. Preferably, the stage position measuring system comprises two linear encoders. Two linear encoders allow a more precise method for positioning the substrate positioning stage.

The stage actuator comprises a belt and a driving member. The substrate positioning stage is connected to the driving element by the belt. The driving element is mounted to the force frame FF. The driving element may include a gearwheel and a motor. Herewith, driving forces F are applied between the substrate positioning stage PS and the force frame FF. As a result, the driving forces F do not introduce disturbances to the metrology frame MF, but are transmitted to the ground GR via the force frame, which results in a higher obtainable accuracy of the inkjet system.

Control electronics are provided to control the position and speed of the substrate positioning stage. A constant speed of the substrate positioning stage may be preferred, because of a resulting constant frequency of jetted droplets.

Between the substrate positioning stage PS and the substrate holder SH, a holder positioning device HD is provided in order to position the substrate holder SH in at least one degree of freedom. Preferably, at least one degree of freedom is determined by the holder positioning device HD, which at least one degree is a translation in the printing direction PD, the Y-direction, relative to the substrate positioning stage PS. Using this configuration, the stage positioning device SD can be used for coarse positioning the substrate holder SH in the printing direction while the holder positioning device HD can be used for fine positioning of the substrate holder in the printing direction relative to the print head assembly. If required, the holder positioning device HD may also be used for fine positioning of the substrate holder in other directions as well, e.g. the X-direction and/or the Z-direction, and may even fine position the substrate holder in rotational directions such as Rx, Ry and Rz as well.

The holder positioning device HD comprises at least one holder actuator and at least one holder position measurement system. Each holder actuator with the accompanying holder position measurement system may determine a single degree of freedom DOF.

In the embodiment of FIG. 19, the substrate holder SH is connected to the substrate positioning stage PS by the holder positioning device HD, wherein all six degrees of freedom are determined by the holder positioning device HD. The holder positioning device is arranged to position the substrate holder SH with respect to the substrate positioning stage in all six possible degrees of freedom. The holder positioning device comprises six holder actuators.

In particular, the holder actuator is a voice coil actuator. The holder position measurement system may be incorporated in the holder actuator. The voice coil actuator may include an encoder to measure a position, in particular a translation, of a movable voice coil actuator body. The voice coil actuator body may be movable about a stroke of at least 2 mm, in particular at least 4 mm, more in particular at least 6 mm. The holder actuator has a holder actuator base which is connected to the substrate positioning stage and a holder actuator body which is connected to the substrate holder. The holder actuator body is movable with respect to the holder actuator base. In particular, the holder actuator body has a body member which limits only one degree of freedom of available directions of movements. In particular, the body member has an elongated portion. In particular the body member is antenna shaped. The body member allows a movement of five degrees of freedom, but resists a movement, more precisely said a translation, in a direction parallel to the elongated portion.

The holder positioning device HD comprises six separate holder actuators in which each holder actuator limits one degree of freedom in translation. Two paired holder actuators limit together a rotational degree of freedom in movement.

The holder positioning device HD comprises three holder actuators which are arranged in an upwards orientation to limit a translation in upwards, substantially vertical, direction. Each actuator holder has an antenna shaped body member which extends in upwards direction. Further, the holder positioning device HD comprises three holder actuators which are arranged in a substantially horizontal orientation. The holder actuators are spaced apart from each other and are positioned on top of the substrate positioning stage. In particular, the holder actuators are positioned in a substantially horizontal plane. The actuator holders are connected to an underside of the substrate holder SH. The three upwards oriented holder actuators limit three degrees of freedom by limiting a translation in Z-direction, a rotation about the X-axis, and a rotation about the Y-axis. The three sidewards oriented holder actuators limit three degrees of freedom by limiting a translation in X- and Y direction and a rotation about the Z-axis.

As shown in FIG. 19, a cross section about the X-axis of the substrate holder is U-shaped, wherein the U-shape is oriented upside down. The U-shaped substrate holder has a U-base and downwardly extending U-legs. The six holder actuators are arranged in between the U-legs. Three vertically oriented holder actuators are connected to the U-base. Two horizontally oriented holder actuators are connected to a first U-leg and one horizontally oriented holder actuator is connected a second U-leg opposite the first U-leg.

To obtain an accurate printing process, it is a prerequisite that a top surface of a substrate travels during a printing operation at a constant distance from a group of nozzles of print heads. Considered in Z-direction, the group of nozzles are positioned in a common plane which defines a virtual plane. The virtual plane is defined in parallel with the common plane. During a printing operation, the top surface of the substrate has to move in parallel to this virtual plane to maintain the constant distance of the nozzles to the top surface of the substrate.

As shown in FIG. 20 and FIG. 22, the print heads PH are held in the print head holder H, such that the nozzles are positioned in parallel with the virtual plane. The print head holder H has at least three reference marks Z1,Z2,Z3 in Z-direction which define an imaginary plane in parallel with the virtual plane. In particular, the print head holder H may have a flat reference surface which includes the three reference marks, wherein the flat reference surface is in parallel with the virtual plane.

The substrate S is positioned at the substrate holder SH. A travel of the substrate in the virtual plane is obtained by moving the substrate holder SH in parallel with the virtual plane. In operation, the holder positioning device HD is controlled such that the substrate holder SH maintains positioned in parallel with the virtual plane during a travel. This in spite of deviations caused by e.g the substrate positioning stage PS. The substrate positioning stage travels about a long stroke of at least 1 meter, in particular about at least 1.5 meters, in the printing direction, wherein deviations may occur from the ideal path. The deviations are e.g. introduced by non-straightness of the stage guidance. The holder positioning device HD compensates for the deviations introduced by the substrate positioning stage during a travel. The holder positioning device HD is programmed to control the substrate holder SH in parallel with the virtual plane.

The three reference marks Z1, Z2, Z3 which define the flat reference surface being parallel to the virtual plane can be used for homing the substrate holder SH. In a calibrating step, the substrate holder SH may be docked against the reference marks Z1, Z2, Z3. The substrate holder may be docked to the print head holder H at a plurality of Y-positions of the substrate positioning stage. The substrate holder SH may be docked with or without holding a substrate S. After docking the substrate holder to the reference marks of the print head holder, the orientation and position may be defined as a docking position. Each docking position may be stored in a memory of the control electronics CE of the inkjet system as a function of an Y-position of the substrate positioning stage PS.

As shown in FIG. 22, the inkjet system, in particular the print head holder PH may further comprise at least one Z-sensor 'z' for measuring a Z-distance from the print head holder H to a top surface of a substrate S or to a top surface of the substrate holder SH. Preferably, the inkjet system IS comprises two Z-sensors which are directed to a top surface which is relevant to maintain a constant distance in between the virtual plane and a top surface of a substrate S. The relevant surface may be a top surface of a substrate holder SH or of a substrate on top of the substrate holder SH. The at least one Z-sensor is stationary mounted to the metrology frame MF. In particular, the Z-sensor is an optical distance sensor for measuring a distance in between the sensor and a surface of an object. Particularly, the at least one Z-sensor is mounted to the print head holder H. During a printing process, the at least one Z-sensor may be used to verify a distance in Z-direction, a Z-distance, of the substrate S with respect to the virtual plane. A constant distance in Z-direction is desired in between the virtual plane defined by the print head nozzles and a top surface of a substrate S. The at least one Z-sensor may generate a signal to the control electronics CE of the inkjet system if a deviation from a constant Z-distance is detected. A first Z-sensor can be mounted to the print head holder H to verify a first degree of freedom which is a constant Z-distance. A second Z-sensor may be positioned with respect to the first Z-sensor and mounted to the print head holder H to verify in addition a second and third degree of freedom DOF which means a verification of a rotation about an X-axis, Rx and/or a rotation about a Y-axis, Ry. Preferably, the first and second z-sensor are aligned in X-direction to verify a z-distance and a rotational degree of freedom about the Y-axis. The control electronics may in a step during the printing process control the holder positioning device HD in position to compensate for a detected deviation in at least one degree of freedom. Another option is that the control electronics are programmed to interrupt the printing process to carry out a subsequent calibration step. During the step of compensation, a step of printing an ink pattern onto the substrate may be upheld.

FIG. 19 further shows a scanning unit SU for scanning a substrate. The scanning unit is mounted on the metrology frame MF. A top surface of the substrate, which serves as a reference surface, is scanned by the scanning unit. The reference surface of the substrate is provided with at least one fiducial member. In particular, the reference surface of the substrate is provided with two fiducial members. A position of the fiducial members in the X-Y plane is determined by the scanning unit SU. By scanning at least two positions, a rotational deviation of the substrate S with respect to the Z-axis is determined. After determining the rotational deviation, the substrate S is rotated about the Z-axis by controlling the substrate holder SH to compensate for the rotational deviation.

FIG. 21 illustrates another step of the calibration method according to the invention. FIG. 21 shows in a schematic view a substrate holder SH which is guided by the substrate positioning stage PS. A travel of the substrate positioning stage PS introduces deviations from an ideal straight path in X-direction. The substrate holder SH comprises a holder position measuring system. The holder position measuring system comprises at least one sensor directed in X-direction, so called X-sensor and a X-calibration element. The X-calibration element is beam shaped and extends in Y-direction. The X-calibration element is mounted to the metrology frame MF. The calibration element XCE is arranged in parallel with a substrate positioning stage guidance PSg. The calibration element XCE has a flat surface, which serves as a X-reference surface. The X-reference surface of the calibration element has a flatness of about 100 μm. In particular, the holder position measuring system comprises at least two sensors which are directed in X-direction. The at least two X-sensors are configured to measure a distance in between the substrate holder and the X-reference surface of the calibration element. The at least two X-sensors are spaced from each other in Y-direction at a predetermined shift 'S'. The at least two X-sensors are arranged at substantially the same height level at the substrate holder, such that the sensors measure a distance from the substrate holder to the reference surface of the calibration element along a same sensor path P.

In the first place, the measurement of the sensors determine a X-deviation in X-direction of the substrate positioning stage with respect to the calibration element. In the second place, the measurement of the at least two X-sensors at the predetermined shift 'S' can be used to determine the flatness of the reference surface of the calibration element as a function of the Y-position of the substrate positioning stage. A first X-sensor measures a first relative distance X1 at a certain Y-position and a second X-sensor measures a second relative distance X2 at the same Y-position of the substrate positioning stage PS. The measurements of relative distances can be performed about the whole travel distance of the substrate positioning stage to output a set of X1 values and a set of X2 values as a function of an Y-position. The distance 'S' in between the first and second sensor is known which implicates a shift in Y-direction of the measured X1 and X2 values. By comparing two sets of measurement values X1 and X2 at a first and second Y-position along the longitudinal axis which corresponds to the shift at a distant 'S', the flatness of the calibration element can be determined. Subsequently, the flatness of the calibration element can be taken into account during a controlled movement of the substrate positioning stage. The flatness of the calibration element can be compensated together with the X-deviation in a feed forward control by the control electronics. The measured values for deviations in X-direction, so called X-deviations, along a travel of the substrate positioning stage in Y-direction can be stored in a memory of the control electronics. The X-deviations can be stored in a table. The holder positioning device is configured to compensate an X-deviation as a function of a position of the substrate positioning stage. During a printing operation, the stored X-deviations as a function of a position of the substrate positioning stage along the longitudinal axis can be used to move the substrate holder in an opposite X-direction to nullify the X-deviation.

Analogous to the compensation in X-direction for X-deviations, a compensation in Z-direction can be carried out for Z-deviations. A travel of the substrate positioning stage PS introduces deviations from an ideal straight path in Z-direction. The substrate holder SH comprises a holder position measuring system. The holder position measuring system comprises at least one sensor directed in Z-direction, a so called Z-sensor Zs1 and a Z-calibration element. The Z-calibration element is beam shaped and extends in Y-direction. The Z-calibration element ZCE is mounted to the metrology frame MF. The Z-calibration element is arranged in parallel with a substrate positioning stage guidance PSg. The Z-calibration element has a flat surface, which serves as a reference surface. In particular, the same X-calibration element, a XZ-calibration element, which is used to measure X-deviations can also be used to measure Z-deviations. The XZ-calibration element may comprises a first reference surface, a X-reference surface, to measure X-deviations and a second reference surface, Z-reference surface, to measure Z-deviations. The Z-reference surface of the calibration element has a flatness of about 100 μm. In particular, the holder position measuring system comprises at least two Z-sensors Zs1, Zs2 which are directed in Z-direction. The at least two Z-sensors are configured to measure a distance in between the substrate holder and the Z-reference surface of the Z-calibration element. The at least two Z-sensors are spaced from each other in Y-direction at a predetermined shift 'S'. The at least two Z-sensors Zs1, Zs2 are arranged at substantially the same position along the lateral X-axis at the substrate holder, such that the Z-sensors measure a distance from the substrate holder to the reference surface of the calibration element along a same sensor path P.

In the first place, the measurement of the Z-sensors determine a Z-deviation in Z-direction of the substrate positioning stage with respect to the calibration element. In the second place, the measurement of the at least two Z-sensors at the predetermined shift 'S' can be used to determine the flatness of the reference surface of the Z-calibration element as a function of the Y-position of the substrate positioning stage. A first Z-sensor measures a first relative distance Z1 at a certain Y-position and a second Z-sensor measures a second relative distance Z2 at the same Y-position of the substrate positioning stage PS. The measurements of relative distances can be performed about the whole travel distance of the substrate positioning stage to output a set of Z1 values and a set of Z2 values as a function of an Y-position. The distance 'S' in between the first and second Z-sensor is known which implicates a shift in Y-direction of the measured Z1 and Z2 values. By comparing two sets of measurement values Z1 and Z2 at a first and second Y-position along the longitudinal axis which corresponds to the shift at a distant 'S', the flatness of the Z-calibration element can be determined. Subsequently, the flatness of the Z-calibration element can be taken into account during a controlled movement of the substrate positioning stage. The flatness of the calibration element can be compensated together with the Z-deviation in a feed forward control by the control electronics. The measured values for deviations in Z-direction, so called Z-deviations, along a travel of the substrate positioning stage in Y-direction can be stored in a memory of the control electronics. The Z-deviations can be stored in a table. The travel of the substrate positioning device is reproductive. The holder positioning device is configured to compensate an Z-deviation as a function of a position of the substrate positioning stage. During a printing operation, the stored Z-deviations as a function of a position of the substrate positioning stage along the longitudinal axis can be used to move the substrate holder in an opposite Z-direction to nullify the Z-deviation.

In a further embodiment of the inkjet system according to the invention, the substrate holder comprises at least a third sensor, also called a Z3-sensor, for measuring a relative distance in Z-direction in between the substrate holder and the calibration element Z-reference surface. The at least third Z3-sensor is arranged at a predetermined distance in X-direction, a shift, from the at least one other Z-sensor. In particular, the at least three Z-sensors can be used to provide a more accurate positioning of the substrate holder in Z-direction and a more accurate rotational positioning about a longitudinal axis Ry. Although the invention has been disclosed with reference to particular embodiments, from reading this description those of skilled in the art may appreciate a change or modification that may be possible from a technical point of view but which do not depart from the scope of the invention as described above and claimed hereafter. Modifications may be made to adapt a particular situation or material to the teachings of the invention without departing from the essential scope thereof. It will be understood by those of skilled in the art that various changes may be made and equivalents may be substituted for elements thereof without departing from the scope of the invention. Therefore, it is intended that the sixth aspect of the invention is not limited to the particular embodiments disclosed in the above detailed description, but that the invention will include all embodiments falling within the scope of the appended clauses with prefix 975.

The FIGS. 23-25 relate in particular to the seventh aspect of the invention.

FIG. 23a shows in a top view an embodiment of the substrate conveyor 1 according to the seventh aspect of the invention. The substrate conveyor 1 is arranged for moving a substrate in an inkjet system. The substrate conveyor comprises a conveyor body 10 and a conveyor guidance 19. The conveyor body 10 comprises a conveyor support face 15 for supporting a substrate during a movement of the conveyor body 10. The conveyor guidance 19 is arranged for guiding the conveyor body 10. In particular, the conveyor guidance 19 is arranged for a linear or rotational guidance of the conveyor body 10.

The substrate conveyor 1 can be arranged as a printing conveyor to transport a substrate through a printing area of the inkjet system. The substrate can be linearly moved by the printing conveyor along a printhead for depositing an ink onto the substrate. Alternatively, the substrate conveyor 1 can be arranged as a station conveyor for handling a substrate in a station. The station can be a buffer station, a supply station, an exit station, a turnover station etc. The station conveyor can be included in a buffer station for buffering substrates or in a turnover station for turning a substrate upside down.

The conveyor body 10 has a rectangular shape. The conveyor body 10 has four side faces 11,12,13,14, a top face 15 and a bottom face.

The conveyor body 10 has a front side face 11, a back side face 12 and two lateral side faces 13,14. The conveyor body has a longitudinal axis L which extends from the front side face 11 to the back side face 12. A transversal axis can be defined in a direction perpendicular to the longitudinal axis L. A substrate can be transferred in a transfer direction T to or away from the conveyor body 10 by passing the front or back side face 11, 12. A double sided arrow is shown in FIG. 1 to indicate the transfer direction T. The transfer direction T is in parallel with the longitudinal axis L of the conveyor body 10.

The top face 15 is arranged as a conveyor support face. The conveyor support face 15 is a flat surface to support a flat substrate. The conveyor support face 15 is subdivided into at least one engagement zone. A plurality of engagement zones allow an engagement with a variety of substrate sizes. The conveyor face 15 comprises at least one gas opening 151 which is in fluid communication with at least one gas channel for conducting gas to or from the conveyor support face. The at least one gas opening 151 can be used to engage with the substrate on the conveyor support face of the conveyor body. The conveyor support face 15 comprises a plurality of gas openings 151 to keep a substrate in an abutting engagement with the conveyor support face by sucking through the gas openings 151. A plurality of gas openings is positioned in a raster. During a movement of the conveyor body, a substrate can be engaged with the conveyor support face 15 by a sucking force by sucking gas from the gas openings. During a transfer, a substrate can be brought in a floating condition with respect to the conveyor support face by supplying gas through the gas openings.

The conveyor body 10 is supported by a conveyor guidance 19. The conveyor guidance 19 is provided at the bottom face of the conveyor body 10. Here, the conveyor guidance is a linear guidance for a linear movement of the conveyor body. Here, the conveyor guidance defines a conveyor direction of the conveyor body which is in parallel with the longitudinal axis L and with the transfer direction T.

Further, the substrate conveyor 1 comprises a transfer unit 20. The transfer unit 20 comprises at least one gripper 22 which is arranged to engage an edge of a substrate. The gripper is shown in further detail in FIG. 3. The transfer unit 20 comprises two grippers 221, 222. The two grippers grip the substrate at two positions at the edge of the substrate. Advantageously, the two grippers prevent a rotational movement of the substrate during a transfer movement.

The at least one gripper is connected to a gripper holder 21. The gripper holder 21 is arranged for holding the at least one gripper 22. The gripper holder is beam shaped. The gripper holder 21 is elongated. The gripper holder 21 extends over the whole width of the conveyor body 10. At both lateral side faces of the conveyor body 10, the gripper holder 21 is supported by a transfer guidance 23. The transfer guidance 23 is provided for guiding the gripper holder 21. The transfer guidance 23 provides a linear movement to the gripper holder 21 in the transfer direction T. The transfer guidance 23 is mounted to the conveyor body 10. The transfer guidance 23 comprises two transfer rails 231, 232. The two transfer rails 231, 232 extent along a longitudinal axis of the conveyor body 10. The two transfer rails extent along the lateral side faces of the conveyor body 10. A first transfer rail 231 is connected at one lateral side face of the conveyor body 10. The second transfer rail 232 is connected to an opposite lateral side face of the conveyor body 10.

FIG. 24a and FIG. 24b show in a schematic side view a more detailed view of the transfer unit 20. The transfer unit comprises a transfer guidance 23 for guiding a gripper holder 21. The gripper holder 21 comprises a slidable gripper holder part 21a which is slidable in a transfer direction T and a dynamic gripper holder part 21b which is movable in an upwards direction U. The slidable gripper holder part 21a has a bearing house 213 to bear the gripper holder 21 to the transfer guidance 23.

The gripper holder part 21a comprises a first and second holder actuator 211. The first holder actuator (not shown) is provided for moving the gripper holder 21 along the transfer guidance 23. The first holder actuator comprises for example an electrical motor with a belt gear or a rack and pinion drive.

The second holder actuator 211 is provided for moving the dynamic gripper holder part 21b from a lifted position to a sunken position. FIG. 24a shows the transfer unit 20 in the sunken, also called lowered position. FIG. 24b shows the transfer unit 20 of in the lifted position. In the sunken position, the transfer unit is positioned below a height level which is defined by the conveyor support face of the conveyor body. In the lifted position, the gripper 22 of the transfer unit reaches above the height level to be able to grip a substrate end to pass over the conveyor support face. The movement of the gripper holder part 21b from the lifted to the sunken position defines an up-down direction which is indicated with a double sided arrow U. The up-down direction is a substantially vertical direction. The up-down direction is directed substantially perpendicular to the longitudinal axis and perpendicular to the transversal axis. The movement of the gripper holder 21 in the up-down direction has a stroke of at least 3 millimeters, in particular at least 5 millimeters, more in particular at least 8 millimeters.

The second holder actuator 211 includes a voice coil actuator for actuating the dynamic holder part 21b and a gripper holder guidance 212 for guiding the dynamic gripper holder part 21b in the up-down direction. The gripper holder guidance 212 comprises at least one spring leaf for a resilient coupling of the dynamic gripper holder part 21b with the slidable gripper part 21a. In this case, the resilient coupling is provided with two parallel arranged spring leafs at both ends of the gripper holder 21. Advantageously, the resilient coupling by spring leafs may provide a hysteresis free coupling which has a relatively fast dynamic behaviour.

FIG. 25a shows the gripper 22 in further detail. The gripper 22 has a gripper outer contour which is elongated and beam shaped. The elongated outer contour defines a length direction. The gripper 22 is suitable to be positioned in length direction in parallel with the elongated gripper holder 21. As shown in FIG. 15b, the gripper 22 can be positioned in a sunken position with respect to an upper surface of the gripper holder 21. Due to its oblong geometry, the gripper 22 can be nested into the gripper holder 21 to obtain a compact configuration. In particular, the gripper holder 21 holds two grippers 22 as shown in FIG. 25b, wherein the grippers 22 are aligned to each other in length direction.

The gripper 22 has a gripper mouth 223 which extends in a direction transversal the length direction. The gripper mouth has an upper gripper mouth part 223b and a lower gripper mouth part 223a. The lower gripper mouth part 223a is connected to a first gripper subframe 224a. The upper gripper mouth part 223a is connected to a second gripper subframe 224b. The second gripper subframe 224b is movable connected to the first gripper subframe 224a by a subframe guidance 225. The subframe guidance is resilient and comprises two leaf springs which are arranged in parallel. In an assembly of the gripper 22 to the gripper holder 21, the lower gripper mouth part 223a is mounted stationary and the upper gripper mouth part 223a is mounted movable with respect to the lower gripper mouth part 223b. In an assembly of the gripper 22 to the gripper holder 21, the first subframe 224a is mounted to the gripper holder 21.

The gripper 22 comprises a gripper actuator 226 for actuating the gripper mouth. In assembly with the gripper holder 21, the gripper actuator is stationary mounted to the gripper holder by a third gripper subframe 224c. The gripper actuator includes a cylinder, in particular a pneumatic cylinder. The cylinder comprises a piston rod 2261 which is linearly movable from a returned to an extended position and v.v. At least one gripper runner 2262 is connected to the end of the piston rod. The gripper runner 2262 is movable along a runner surface 2242. The second gripper subframe 224b comprises a wedge element 2241. The runner surface 2242 is provided onto the wedge element 2241. The wedge element is fixedly connected to the upper mouth part 223b.

Here, the gripper comprises two parallel arranged wedge elements. Two gripper runners are connected to the piston rod. The upper mouth part 223b can be move towards the lower mouth part by moving the piston rod to the extended position. By moving the piston rod to the extended position, the gripper runner 2262 runs along the running surface 2242. During the movement, the gripper runner 2262 presses onto the runner surface 2242 and hence moves the upper mouth part 223b in a direction towards the lower mouth part 223a. The subframe guidance is resilient to return the upper mouth part 223b away from the lower mouth part when the gripper runner moves back to the returned position.

Although several aspects of the invention have been disclosed with reference to particular embodiments, from reading this description those of skilled in the art may appreciate a change or modification that may be possible from a technical point of view but which do not depart from the scope of the invention as described above. Modifications may be made to adapt a particular situation or material to the teachings of the aspects of the invention without departing from the essential scope thereof. It will be understood by those of skilled in the art that various changes may be made and equivalents may be substituted for elements thereof without departing from the scope of the invention. Therefore, it is intended that the invention is not limited to the particular embodiments disclosed in the above detailed description, but that the invention will include all embodiments falling within the scope of the clauses and claims.

Thus, the first aspect of the invention provides a printing process which comprises an in-line quality inspection to inspect a printed ink pattern on misprints. Advantageously, substrates can be inspected and rejected or approved before a further processing which increases the efficiency of the printing process. The invention provides further improvements to the in-line quality inspection by extracting control features from a raster input image in a preparing step to speed up a final quality inspection. Further, the invention provides an inkjet system to carry out the printing process according to the invention.

The invention claimed is:

1. A substrate conveyor for supporting a substrate during a movement in an inkjet system, wherein the substrate conveyor comprises a conveyor body including a conveyor support face for supporting the substrate, and a conveyor guidance for guiding the conveyor body in a conveyor direction, wherein the substrate conveyor comprises further a substrate transfer unit for transferring the substrate to and fro the conveyor support face, wherein the substrate transfer unit comprises at least one gripper for gripping the substrate;
   a gripper holder for holding the at least one gripper;
   a transfer guidance for guiding the gripper holder;
   a first holder actuator for driving the gripper holder along the transfer guidance in a transfer direction along the substrate conveyor;
   wherein the substrate transfer guidance is fixed to the conveyor body, such that during a movement of the substrate conveyor body, the substrate transfer guidance moves together with the conveyor body.

2. The substrate conveyor according to claim 1, wherein the at least one gripper is movable over the conveyor support face along a gripper path from a first to a second position, wherein the first position is located in a front region of the substrate conveyor body and wherein the second position is located in a back region of the substrate conveyor body.

3. The substrate conveyor according to claim 2, wherein the gripper path includes a downward extending gripper path section for sinking down the at least one gripper with respect to the substrate conveyor support face.

4. The substrate conveyor according to claim 3, wherein the at least one gripper comprises a clamp element for clamping a substrate at an edge region.

5. The substrate conveyor according to claim 2, wherein the at least one gripper comprises a clamp element for clamping a substrate at an edge region.

6. The substrate conveyor according to claim 2, wherein the gripper holder holds at least a pair of a first gripper and a second gripper, wherein the paired first and second gripper are oriented in opposite directions.

7. The substrate conveyor according to claim 1, wherein the at least one gripper comprises a clamp element for clamping a substrate at an edge region.

8. The substrate conveyor according to claim 1, wherein the gripper holder holds at least a pair of a first gripper and a second gripper, wherein the paired first and second gripper are oriented in opposite directions.

9. The substrate conveyor according to claim 1, wherein the conveyor support face comprises a plurality of gas openings for keeping a substrate in abutting engagement with the conveyor support face by sucking.

10. The substrate conveyor according to claim 1, wherein the substrate conveyor is a printing conveyor for conveying a substrate during a printing operation, wherein the printing conveyor comprises
   a substrate positioning stage for moving a substrate in a printing direction with respect to the print head holder during the printing operation;
   a stage positioning device for positioning the substrate positioning stage with respect to the frame; and
   a substrate holder connected to the substrate positioning stage for holding a substrate;
   wherein the substrate holder is movable connected in at least one degree of freedom with respect to the substrate positioning stage, wherein a holder positioning device is provided for positioning the substrate holder with respect to the substrate positioning stage in the at least one degree of freedom, wherein the transfer guidance of the substrate transfer unit is fixed to the substrate holder.

11. The substrate conveyor according to claim 1, wherein the substrate conveyor is a station conveyor of a handling station for handling a substrate in the handling station.

12. An inkjet system for printing an ink pattern on a substrate comprising:
   a substrate conveyor according to claim 1;
   a frame for holding components of the inkjet system;
   a print head holder for holding at least one print head, which printhead holder is connected to the frame;
   wherein the substrate conveyor has a conveyor body which is movable relative to the frame, wherein the substrate transfer unit is connected to the conveyor body, such that during a movement of the conveyor body, the substrate transfer unit moves together with the conveyor body.

13. The inkjet system according to claim 12, further comprising a substrate conveyor as a printing conveyor for transporting a substrate in a printing area during a printing operation.

14. The inkjet system according to claim 12, wherein the inkjet system comprises a handling station for handling a substrate, wherein the handling station comprises a substrate conveyor as a station conveyor for conveying a substrate, wherein the station conveyor comprises a transfer unit which is arranged to transfer a substrate from the station conveyor to the printing conveyor.

15. The inkjet system according to claim 14, wherein the handling station is a supply station for supplying a substrate to the printing conveyor, a buffer station for temporary storing a substrate or a discharge station for discharging a substrate away from the printing conveyor.

16. A method of transferring a substrate from a first substrate conveyor to a second substrate conveyor of an inkjet system comprising the steps of:
   providing a first and second substrate conveyor, wherein at least one of the first and second substrate conveyor comprises a transfer unit, wherein the transfer unit is mounted to the substrate conveyor, wherein the transfer unit comprises a gripper holder including at least one gripper which is movable along a gripper path from a first position at a front region of the substrate conveyor to a second position at a back region of the substrate conveyor;
   providing a substrate on a conveyor support face of the first conveyor;
   positioning the second substrate conveyor adjacent the first substrate conveyor;
   positioning the gripper holder to the respectively first position or second position, such that the at least one gripper is able to grip the substrate at the first conveyor at an edge region;
   gripping the substrate at the first substrate conveyor at the edge region;
   moving the gripper holder to the respectively second or first position while gripping the substrate and moving the substrate from the first substrate conveyor to the second substrate conveyor;
   releasing the substrate when the substrate is positioned at the second substrate conveyor.

17. The method according to claim 16, wherein the substrate is transferred in a floating condition from the first substrate conveyor to the second substrate conveyor, which floating condition is obtained by supplying gas to the substrate conveyor support face underneath a supported substrate.

18. The method according to claim 16, wherein the substrate is all that imposition at the second substrate conveyor by a sucking force at the substrate conveyor support face.

19. The method according to claim 16, wherein a calibration for positioning the second substrate conveyor adjacent the first substrate conveyor is performed by mechanically docking the first and second substrate conveyor to each other, and
   wherein the calibration comprises a step of storing a docking position in which the first substrate conveyor is docked to the second substrates conveyor by control electronics.

20. The method according to claim 16, wherein the first or second substrate conveyor is a printing conveyor, and the at least one gripper is sunken with respect to a conveyor support face of the printing conveyor after transferring a substrate onto the printing conveyor.

* * * * *